(12) United States Patent
Chulay et al.

(10) Patent No.: US 7,419,674 B2
(45) Date of Patent: Sep. 2, 2008

(54) ALPHA VIRUS-BASED CYTOMEGALOVIRUS VACCINES

(75) Inventors: Jeffrey D. Chulay, Chapel Hill, NC (US); Sergey Dryga, Chapel Hill, NC (US); Elizabeth A. Reap, Durham, NC (US); Robert A. Olmsted, Chapel Hill, NC (US); John S. Morris, Cary, NC (US)

(73) Assignee: Alpha Vax, Inc., Research Triangle Park, NC (US)

( * ) Notice: Subject to any disclaimer, the term of this patent is extended or adjusted under 35 U.S.C. 154(b) by 20 days.

(21) Appl. No.: 10/886,773

(22) Filed: Jul. 8, 2004

(65) Prior Publication Data
US 2005/0054107 A1    Mar. 10, 2005

Related U.S. Application Data

(60) Provisional application No. 60/486,501, filed on Jul. 11, 2003.

(51) Int. Cl.
*A61K 39/295* (2006.01)
*A61K 39/245* (2006.01)
*C12N 7/01* (2006.01)
*C12N 15/86* (2006.01)

(52) U.S. Cl. .............. 424/199.1; 424/192.1; 424/230.1; 435/235.1; 435/320.1

(58) Field of Classification Search .............. 435/235.1, 435/320.1, 69.3, 69.1; 424/199.1, 93.2
See application file for complete search history.

(56) References Cited

U.S. PATENT DOCUMENTS

| | | | |
|---|---|---|---|
| 4,650,764 A | 3/1987 | Temin et al. | |
| 4,708,871 A | 11/1987 | Geysen | |
| 5,091,309 A | 2/1992 | Schlesinger et al. | |
| 5,185,440 A | 2/1993 | Davis et al. | |
| 5,217,879 A | 6/1993 | Huang et al. | |
| 5,505,947 A | 4/1996 | Johnston et al. | |
| 5,521,082 A | 5/1996 | Lewis et al. | |
| 5,639,650 A | 6/1997 | Johnston et al. | |
| 5,643,576 A | 7/1997 | Johnston et al. | |
| 5,703,057 A | 12/1997 | Johnston et al. | |
| 5,726,022 A | 3/1998 | Burmer | |
| 5,739,026 A | 4/1998 | Garoff et al. | |
| 5,766,602 A | 6/1998 | Xiong et al. | |
| 5,789,245 A | 8/1998 | Dubensky et al. | |
| 5,792,462 A | 8/1998 | Johnston et al. | |
| 5,811,407 A | 9/1998 | Johnston et al. | |
| 5,814,482 A | 9/1998 | Dubensky et al. | |
| 5,827,658 A | 10/1998 | Liang et al. | |
| 5,831,016 A | 11/1998 | Wang et al. | |
| 5,843,723 A | 12/1998 | Dubensky et al. | |
| 5,853,719 A | 12/1998 | Nair et al. | |
| 5,958,738 A | 9/1999 | Lindermann et al. | |
| 5,989,553 A | 11/1999 | Johnston et al. | |
| 6,008,035 A | 12/1999 | Johnston et al. | |
| 6,015,686 A | 1/2000 | Dubensky et al. | |
| 6,015,694 A | 1/2000 | Dubensky et al. | |
| 6,146,874 A | 11/2000 | Zolotukhin et al. | |
| 6,156,558 A | 12/2000 | Johnston et al. | |
| 6,190,666 B1 | 2/2001 | Garoff et al. | |
| 6,194,191 B1 | 2/2001 | Zhang et al. | |
| 6,197,502 B1 | 3/2001 | Renner et al. | |
| 6,224,879 B1 | 5/2001 | Sjoberg et al. | |
| 6,242,259 B1 | 6/2001 | Polo et al. | |
| 6,261,570 B1 | 7/2001 | Parker et al. | |
| 6,267,967 B1 | 7/2001 | Johnston et al. | |
| 6,306,388 B1 | 10/2001 | Nair et al. | |
| 6,329,201 B1 | 12/2001 | Polo et al. | |
| 6,342,226 B1 * | 1/2002 | Betbeder et al. | 424/196.11 |
| 6,342,372 B1 | 1/2002 | Dubensky et al. | |
| 6,376,236 B1 | 4/2002 | Dubensky et al. | |
| 6,391,632 B1 | 5/2002 | Dubensky et al. | |
| 6,426,196 B1 | 7/2002 | Dubensky et al. | |
| 6,448,389 B1 * | 9/2002 | Gonczol et al. | 536/23.72 |
| 6,485,958 B2 | 11/2002 | Blanch et al. | |
| 6,495,143 B2 | 12/2002 | Lee et al. | |
| 6,521,235 B2 | 2/2003 | Johnston et al. | |
| 6,531,135 B1 | 3/2003 | Johnston et al. | |
| 6,541,010 B1 | 4/2003 | Johnston et al. | |

(Continued)

FOREIGN PATENT DOCUMENTS

| | | |
|---|---|---|
| WO | WO 92/10578 | 6/1992 |
| WO | WO 95/07994 | 3/1995 |
| WO | WO 95/27044 | 10/1995 |
| WO | WO 95/31565 | 11/1995 |
| WO | WO 96/17072 | 6/1996 |
| WO | WO 96/37220 | 11/1996 |
| WO | WO 96/37616 | 11/1996 |
| WO | WO 99/07834 | 2/1999 |
| WO | WO 99/08706 | 2/1999 |
| WO | WO 99/51263 | 10/1999 |

(Continued)

OTHER PUBLICATIONS

Tugizov et al., "Mutated Forms of Human Cytomegalovirus Glycoprotein B Are Impaired in Inducing Syncytium Formation," Virology 209 (1995), pp. 580-591.*

(Continued)

*Primary Examiner*—Mary E Mosher
(74) *Attorney, Agent, or Firm*—Myers Bigel Sibley & Sajovec, P.A.

(57) ABSTRACT

The present invention provides methods and compositions comprising a population of alphavirus replicon particles comprising alphavirus replicon RNAs, wherein a first replicon RNA comprises nucleic acid encoding cytomegalovirus pp65 and IE1 protein or immunogenic fragments thereof, and a second replicon RNA comprises nucleic acid encoding cytomegalovirus gB protein or an immunogenic fragment thereof, and wherein each of the two replicon RNAs is contained within a separate alphavirus replicon particle.

50 Claims, 3 Drawing Sheets

U.S. PATENT DOCUMENTS

| | | | |
|---|---|---|---|
| 6,583,121 | B1 | 6/2003 | Johnston et al. |
| 6,767,699 | B2 | 7/2004 | Polo et al. |
| 6,770,283 | B1 | 8/2004 | Garoff et al. |
| 6,783,939 | B2 | 8/2004 | Olmsted et al. |
| 6,844,188 | B1 | 1/2005 | MacDonald et al. |
| 7,045,335 | B2 | 5/2006 | Smith et al. |
| 7,267,823 | B2 * | 9/2007 | Hart et al. ............... 424/204.1 |
| 2001/0016199 | A1 | 8/2001 | Johnston et al. |
| 2002/0018766 | A1 | 2/2002 | Roberts et al. |
| 2002/0034521 | A1 | 3/2002 | Lee et al. |
| 2002/0102273 | A1 | 8/2002 | Grieve et al. |
| 2002/0141975 | A1 * | 10/2002 | Olmsted et al. ............ 424/93.2 |
| 2002/0156251 | A1 * | 10/2002 | Prieur et al. ............... 536/23.1 |
| 2002/0164582 | A1 | 11/2002 | Hart et al. |
| 2003/0021766 | A1 | 1/2003 | Vadjy et al. |
| 2003/0091591 | A1 | 5/2003 | Xiong et al. |
| 2003/0096397 | A1 | 5/2003 | Schlesinger et al. |
| 2003/0119182 | A1 * | 6/2003 | Smith et al. .............. 435/320.1 |
| 2003/0120060 | A1 | 6/2003 | Gonczol et al. |
| 2003/0148262 | A1 | 8/2003 | Polo et al. |
| 2003/0152590 | A1 | 8/2003 | Hevey et al. |
| 2003/0232036 | A1 | 12/2003 | Johnston et al. |
| 2003/0232324 | A1 | 12/2003 | Polo et al. |
| 2004/0008458 | A1 | 1/2004 | Kase et al. |
| 2004/0009183 | A1 | 1/2004 | Lee et al. |
| 2004/0009945 | A1 | 1/2004 | Lee et al. |
| 2004/0029279 | A1 | 2/2004 | Kovacs et al. |
| 2004/0030117 | A1 | 2/2004 | Johnston et al. |
| 2004/0121466 | A1 | 6/2004 | Johnston et al. |
| 2004/0146859 | A1 | 7/2004 | Hart et al. |
| 2004/0166573 | A1 | 8/2004 | Smith et al. |
| 2004/0208848 | A1 * | 10/2004 | Smith et al. ................ 424/93.2 |
| 2005/0031592 | A1 | 2/2005 | Doolan et al. |
| 2005/0118251 | A1 | 6/2005 | Nagata et al. |

FOREIGN PATENT DOCUMENTS

| | | |
|---|---|---|
| WO | WO 00/39302 | 7/2000 |
| WO | WO 00/39318 A | 7/2000 |
| WO | WO 00/61772 | 10/2000 |
| WO | WO 01/16343 A1 | 3/2001 |
| WO | WO 02/003917 | 1/2002 |
| WO | WO 02/04493 | 1/2002 |
| WO | WO 02/20721 | 3/2002 |
| WO | WO 03/023026 A | 3/2003 |
| WO | WO 03/083065 A2 | 10/2003 |
| WO | WO 2004/055166 | 7/2004 |
| WO | WO 2004/055167 | 7/2004 |
| WO | WO 2004/085660 | 10/2004 |
| WO | WO 2005/007689 | 1/2005 |

OTHER PUBLICATIONS

Vaz-Santiago, "Ex Vivo Stimulation and Expansion of both CD4 and CD8 T Cells from Peripheral Blood Mononuclear Cells of Human Cytomegalovirus-Seropositive Blood Donors by Using a Soluble Recombinant Chimeric Protein, IE1-pp65," Journal of Virology, vol. 75, No. 17 (2001), pp. 7840-7847.*

Caltenco-Serrano et al (Revista Latinoamericana de Microbiologia 43: 177-182, 2001).*

Pugachev et al (Virology 212:587-594, 1995).*

Elkington et al (Journal of virology 77:5226-5240, May 2003).*

Davis et al. "Alphavirus Replicon Particles as Candidate HIV Vaccines" *IUBMB Life* 53: 209-211 (2002).

Baric et al. "Expression and Self-Assembly of Norwalk Virus Capsid Protein from Venezuelan Equine Encephalitis Virus Replicons" *Journal of Virology* 76(6): 3023-3030 (2002).

Eiben et al. "Establishment of an HLA-A*0201 Human Papillomavirus Type 16 Tumor Model to Determine the Efficacy of Vaccination Strategies in HLA-A*0201 Transgenic Mice" *Cancer Research* 62:5792-5799 (2002).

Eralp et al. "Doxorubicin and Paclitaxel Enhance the Antitumor Efficacy of Vaccines Directed Against HER 2/neu in a Murine Mammary Carcinoma Model" *Breast Cancer Research* 6:R275-R283 (2004).

Lee et al. "Candidate Vaccine Against Botulinum Neurotoxin Serotype A Derived from a Venezeulan Equine Encephalitis Virus Vector System" *Infection and Immunity* 69(9): 5709-5715 (2001).

Lee et al. "Immune Protection Against Staphylococcal Enterotoxin-Induced Toxic Shock by Vaccination with a Venezuelan Equine Encephalitis Virus Replicon" *Journal of Infectious Diseases* 185: 1192-1196 (2002).

MacDonald et al. "Role of Dendritic Cell Targeting in Venezuelan Equine Encephalitis Virus Pathogenesis" *Journal of Virology* 74(2): 914-922 (2000).

Nelson et al. "Venezuelan Equine Encephalitis Replicon Immunization Overcomes Intrinsic Tolerance and Elicits Effective Anti-Tumor Immunity to the "self" Tumor Associated Antigen, *neu* in a Rat Mammary Tumor Model" *Breast Cancer Research and Treatment* 63R: 1-15 (2003).

Pushko et al. "Individual and Bivalent Vaccines Based on Alphavirus Replicons Protect Guinea Pigs Against Infection with Lassa and Ebola Viruses" *Journal of Virology* 75(23): 11677-11685 (2001).

Schultz-Cherry et al. "Influenza Virus (A/HK/156/97) Hemagglutinin Expressed by an Alphavirus Replicon System Protects Chicken Against Lethal Infection with Hong Kong-Origin H5N1 Viruses" *Virology* 278: 55-59 (2000).

Wang et al. "Alphavirus Replicon Particles Containing the Gene for HER2/neu Inhibit Breast Cancer Growth and Tumorigenesis" *Breast Cancer Research* 7: R145-R155 (2005).

Velders et al. "Eradication of Established Tumors by Vaccination with Venezuelan Equine Encephalitis Virus Replicon Particles Delivering Human Papillomavirus 16 E7 RNA" *Cancer Research* 61: 7861-7867 (2001).

Wilson et al. "Protection from Ebola Virus Mediated by Cytotoxic T Lymphocytes Specific for the Viral Nucleoprotein" *Journal of Virology* 75(6): 2660-2664 (2001).

Gonczol and Plotkin "Development of a Cytomegalovirus Vaccine: Lessons from Recent Clinical Trials" *Exp. Opin. Biol. Ther.* 1(3):401-412 (2001).

Hariharan et al. "DNA Immunization Against Herpes Simplex Virus: Enhanced Efficacy Using a Sindbis Virus-Based Vector" *Journal of Virology* 72(2):950-958 (1998).

International Search Report issued for PCT/2004/021772; mailed on Dec. 28, 2004.

Lundstrom "Alphavirus Vectors: Applications for DNA Vaccine Production and Gene Expression" *Intervirology* 43:247-257 (2000).

McCue and Anders "Soluble Expression and Complex Formation of Proteins Required for HCMV DNA Replication Using the SFV Expression System" *Protein Expression and Purification* 13:301-312 (1998).

Schlesinger and Dubensky Jr. "Alphavirus Vectors for Gene Expression and Vaccines" *Current Opinion in Biotechnology* 10(5): 434-439 (1999).

Temperton "DNA Vaccines Against Cytomegalovirus: Current Progress" *International Journal of Antimicrobial Agents* 19:169-172 (2002).

Bourne et al. "Preconception Immunization with a Cytomegalovirus (CMV) Glycoprotein Vaccine Improves Pregnancy Outcome in a Guinea Pig Model of Congenital CMV Infection" *The Journal of Infectious Diseases* 183:59-64 (2001).

Carlson et al. "Expression, Purification and Characterization of a Soluble Form of Human Cytomegalovirus Glycoprotein B" *Virology* 239:198-205 (1997).

Chatterjee et al. "Modification of Maternal and Congenital Cytomegalovirus Infection by Anti-Glycoprotein B Antibody Transfer in Guinea Pigs" *The Journal of Infectious Diseases* 183:1547-1553 (2001).

Geysen et al. "*A Priori* Delineation of a Peptide which Mimics a Discontiuous Antigenic Determinant" *Molecular Immunology* 23(7):709-715 (1986).

Geyson et al. "Use of Peptide Synthesis to Probe Viral Antigens for Epitopes to a Resolution of a Single Amino Acid" *Proceedings of the National Academy of Sciences of the United States of America* 81(13):3998-4002 (1984).

Gyulai et al. "Cytotoxic T Lymphocyte (CTL) Responses to Human Cytomegalovirus pp65, IE1-Exon4, gB, pp150, and pp28 in Healthy Individuals: Reevaluation of Prevalence of IE1-Specific CTLs" *J. Infect. Dis.* 181:1537-1546 (2000).

International Search Report corresponding to PCT/US2004/008458, mailed on Oct. 25, 2004.

Knight "Secretion from Bovine Chromaffin Cells Acutely Expressing Exogenous Proteins using a Recombinant Semliki Forest Virus Containing an EGFP Reporter" *Molecular and Cellular Neuroscience* 14(6):486-505 (1999).

Kohl et al. "Transient Gene Expression in Mammalian and Mosquito Cells Using a Recombinant Semliki Forest Virus Expressing T7 RNA Polymerase" *Applied Microbiology and Biotechnology* 53(1):51-56 (1999).

Liljestrom et al. "A New Generation of Animal Cell Expression Vectors Based on the Semliki Forest Virus Replicon" *Bio/Technology* 9:1356-1361 (1991).

Maecker et al. "Use of Overlapping Peptide Mixtures as Antigens for Cytokine Flow Cytometry" *Journal of Immunological Methods* 255:27-40 (2001).

Morello et al. "Suppression of Murine Cytomegalovirus (MCMV) Replication with a DNA Vaccine Encoding MCMV M84 (a Homolog of Human Cytomegalovirus pp65" *Journal of Virology* 74(8):3696-3708 (2000).

Olmsted et al. "Alphavirus Vectors and Virosomes with Modified HIV Genes for Use in Vaccines" U.S. Appl. No. 10/929,234, filed in the U.S. Patent and Trademark Office on Aug. 30, 2004.

Pedersen et al. "Separation, Isolation, and Immunological Studies of the Structural Proteins of Venezuelan Equine Encephalomyelitis Virus" *J. Virology* 14(4):740-744 (1974).

Plotkin et al. "Multicenter Trial of Towne Strain Attenuated Virus Vaccine in Seronegative Renal Transplant Recipients" *Transplantation* 58(11):1176-1178 (1994).

Pugachev et al. "Development of a Rubella Virus Vaccine Expression Vector: Use of a Picornavirus Internal Ribosome Entry Site Increases Stability of Expression" *Journal of Virology* 74(22):10811-10815 (2000).

Pushko et al. "Replicon-Helper Systems from Attenuated Venezuelan Equine Encephalitis Virus: Expression of Heterologous Genes in Vitro and Immunization against Heterologous Pathogens in Vivo" *Virology* 239:389-401 (1997).

Rayner et al. "Alphavirus Vectors and Vaccination" *Reviews in Medical Virology* 12(5):279-296 (2002).

Shi et al. "Construction and Characterization of Subgenomic Replicons of New York Strain of West Nile Virus" *Virology* 296(2):219-233 (2002).

Smith et al. "Improved Alphavirus Replicons and Helper Constructs" U.S. Appl. No. 10/804,331, filed in the U.S. Patent and Trademark Office on Mar. 19, 2004.

Walter et al. "Reconstitution of Cellular Immunity Against Cytomegalovirus in Recipients of Allogeneic Bone Marrow by Transfer of T-Cell Clones from the Donor" *The New England Journal of Medicine* 333(16):1038-1044 (1995).

Wang et al. "Core Protein-Coding Sequence, But Not Core Protein, Modulates the Efficiency of Cap-Independent Translation Directed by the Internal Ribosome Entry Site of Hepatitis C Virus" *Journal of Virology* 74(23):11347-11358 (2000).

Wen et al. "Tricistronic Viral Vectors Co-Expressing Interleukin-12 (IL-12) and CD80 (B7-1) for the Immunotherapy of Cancer: Preclinical Studies in Myeloma" *Cancer Gene Therapy* 8(5):361-370 (2001).

Wilson et al. "Naturally Occurring Dicistronic Cricket Paralysis Virus RNA is Regulated by Two Internal Ribosome Entry Sites" *Molecular and Cellular Biology* 20(14):4990-4999 (2000).

Adler et al. "A Canarypox Vector Expressing Cytomegalovirus (CMV) Glycoprotein B Primes for Antibody Responses to a Live Attenuated CMV Vaccine (Towne)" *The Journal of Infectious Diseases* 180:843-6 (1999).

Armas et al. "DNA Immunization Confers Protection against Murine Cytomegalovirus Infection" *Journal of Virology* 70(11):7921-7928 (1996).

Berensci et al. "A Canarypox Vector-Expressing Cytomegalovirus (CMV) Phosphoprotein 65 Induces Long-Lasting Cytotoxic T Cell Responses in Human CMV-Seronegative Subjects" *The Journal of Infectious Diseases* 183:1171-9 (2001).

Berensci et al. "Murine cytotoxic T cell response specific for human cytomegalovirus glycoprotein B (gB) induced by adenovirus and vaccinia virus recombinants expressing gB" *Journal of General Virology* 74:2507-2512 (1993).

Britt et al. "Formulation of an Immunogenic Human Cytomegalovirus Vaccine: Responses in Mice" *The Journal of Infectious Diseases* 171:18-25 (1995).

Endresz et al. "Induction of human cytomegalovirus (HCMV)-glycoprotein B (gB)-specific neutralizing antibody and phosphoprotein 65 (pp65)-specific cytotoxic T lymphocyte responses by naked DNA immunization" *Vaccine* 17:50-58 (1999).

Frey et al. "Effects of Antigen Dose and Immunization Regimens on Antibody Responses to a Cytomegalovirus Glycoprotein B Subunit Vaccine" *The Journal of Infectious Diseases* 180:1700-3 (1999).

Gonczol et al. "Preclinical evaluation of ALVAC (canarypox)-human cytomegalovirus glycoprotein B vaccine candidate" *Vaccine* 13(12):1080-1085 (1995).

Kern et al. "Cytomegalovirus (CMV) Phosphoprotein 65 Makes a Large Contribution to Shaping the T Cell Repertoire in CMV-Exposed Individuals" *The Journal of Infectious Diseases* 185:1709-16 (2002).

Marshall et al. "An Adenovirus Recombinant that Expresses the Human Cytomegalovirus Major Envelope Glycoprotein and Induces Neutralizing Antibodies" *The Journal of Infectious Diseases* 162:1177-1181 (1990).

Pass et al. "A Subunit Cytomegalovirus Vaccine Based on Recombinant Envelope Glycoprotein B and a New Adjuvant" *The Journal of Infectious Diseases* 180:970-5 (1999).

Pass et al. "Development of Cytomegalovirus Vaccines: Prospects for Prevention of Congenital CMV Infection" *Seminars in Pediatric Infectious Diseases* 13(3):196-204 (2002).

Schleiss et al. "Animal models of congenital cytomegalovirus infection: an overview of progress in the characterization of guinea pig cytomegalovirus (GPCMV)" *Journal of Clinical Virology* 25:S37-S49 (2002).

Speckner et al. "Antigenic domain 1 of human cytomegalovirus glycoprotein B induces a multitude of different antibodies which, when combined, results in incomplete virus neutralization" *Journal of General Virology* 80:2183-2191 (1999).

Balasuriya et al. "Alphavirus Replicon Particles Expressing the Two Major Envelope Proteins of Equine Arteritis Virus Induce High Level Protection Against Challenge with Virulent Virus in Vaccinated Horses" *Vaccine* 20:1609-1617 (2002).

Barouch et al. 2000. Augmentation of Immune Responses to HIV-1 and Simian Immunodeficiency Virus DNA Vaccines by IL-2/Ig Plasmid Administration in Rhesus Monkeys. PNAS 97(8): 4192-4197.

Barry et al. "Expression Library Immunization to Discover and Improve Vaccine Antigens" Immunological Reviews 199:68-83 (2004).

Bell et al. "Effect of Low-NaCl Medium on the Envelope Glycoproteins of Sindbis Virus" Journal of Virology 25(3):764-769 (1978).

Berglund et al. 1993. Semliki Forest Virus Expression System: Production of Conditionally Infectious Recombinant Particles. Bio/Technology 11:916-920.

Bergman et al. "Long-Term Survival of Dogs with Advanced Malignant Melanoma after DNA Vaccination with Xenogeneic Human Tyrosinase: A Phase I Trial" Clin. Cancer Research 9:1284-1290 (2003).

Bernard et al. "Mutations in the E2 Glycoprotein of Venezuelan Equine Encephalitis Virus Confer Heparan Sulfate Interaction, Low Morbidity, and Rapid Clearance from Blood of Mice" Virology 276:93-103 (2000).

Betts et al. 1997. Cross-Clade Human Immunodeficiency Virus (HIV)-Specific Cytotoxic T-Lymphocyte Responses in HIV-Infected Zambians. J. Virol. 71(11):8908-8911.

Bredenbeek et al. 1993. Sindbis Virus Expression Vectors: Packaging of RNA Replicons by Using Defective Helper RNAs. Journal of Virology 67:6439-6446.

Caley et al. 1997. Humoral, Mucosal, and Cellular Immunity in Response to a Human Immunodeficiency Virus Type 1 Immunogen Expressed by a Venezuelan Equine Encephalitis Virus Vaccine Vector. J. Virol. 71(4):3031-3038.

Caley et al. "Venezuelan Equine Encephalitis Virus Vectors Expressing HIV-1 Proteins: Vector Design Strategies for Improved Vaccine Efficacy" Vaccine 17:3124-3135 (1999).

Casimiro et al. "Vaccine-Induced Immune Responses in Rodents and Nonhuman Primates by Use of a Humanized Immunodeficiency Virus Type 1 pol Gene" Journal of Virology 76:185-194 (2002).

Chappell et al. "A 9-nt Segment of a Cellular mRNA can Function as an Internal Ribosome Site (IRES) and when Present in Linked Multiple Copies Greatly Enhances IRES Activity" PNAS 97(4):1536-1541 (2000).

Corsini et al. 1996. Efficiency of Transduction by Recombinant Sindbis Replicon Virus Varies Among Cell Lines, Including Mosquito Cells and Rat Sensory Neurons. BioTechniques 21(3):492-497.

Cutler et al. 1986. Mutants of the Membrane-binding Region of Semliki Forest Virus E2 Protein. I. Cell Surface Transport and Fusogenic Activity. The Journal of Cell Biology 102:889-901.

Davis et al. "A Single Nucleotide Change in the E2 Glycoprotein Gene of Sindbis Virus Affects Penetration Rate in Cell Culture and Virulence in Neonatal Mice" Proc. Natl. Acad. Sci. USA 83:6771-6775 (1986).

Davis et al. 1989. In Vitro Synthesis of Infectious Venezuelan Equine Encephalitis Virus RNA from a cDNA Clone: Analysis of a Viable Deletion Mutant. Virology 171:189-204.

Davis et al. 1990. In Vitro Synthesis of Infectious Venezuelan Equine Encephalitis Virus RNA from a cDNA Clone: Analysis of a Viable Deletion Mutant and Mutations Affecting Virulence. Vaccines 90:109-113.

Davis et al. 1991. Attenuating Mutations in the E2 Glycoprotein Gene of Venezuelan Equine Encephalitis Virus: Construction of Single and Multiple Mutants in a Full-Length cDNA Clone. Virology 183:20-31.

Davis et al. 1993. A Genetically Engineered Live Virus Vaccine for Venezuelan Equine Encephalitis. J. Cell Biochemistry Supplement O No. 17 Part D, Abstract N404.

Davis et al. 1994. A molecular genetic approach to the study of Venezuelan equine encephalitis virus pathogenesis. Archives of Virology 9:99-109.

Davis et al. 1995. Attenuated Mutants of Venezuelan Equine Encephalitis Virus Containing Lethal Mutations in the PE2 Cleavage Signal Combined with a Second-Site Suppressor Mutation in E1. Virology 212:102-110.

Davis et al. 1996. A Viral Vaccine Vector that Expresses Foreign Genes in Lymph Nodes and Protects against Mucosal Challenge. Journal of Virology 70:3781-3787.

Davis et al. 1996. Immunization against influenza with Attenuated Venezuelan Equine Encephalitis Virus Vectors. In: Options for the Control of Influenza III. L. E. Brown and A. W. Hampson, eds. Elsevier, Amsterdam pp. 803-809.

Davis et al. 2000. Vaccination of Macaques against Pathogenic Simian Immunodeficiency Virus with Venezuelan Equine Encephalitis Virus Replicon Particles. J. Virol. 74(1):371-378.

Dubensky et al. 1996. Sindbis Virus DNA-Based Expression Vectors: Utility for in Vitro and in Vivo Gene Transfer . Journal of Virology 70:508-519.

Dubuisson et al. 1993. Sindbis Virus Attachment: Isolation and Characterization of Mutants with Impaired Binding to Vertebrate Cells. Journal of Virology 67:3363-3374.

Favre et al. 1993. Semliki Forest Virus Capsid Protein Expressed by a Baculovirus Recombinant. Archives of Virology 132:307-319.

Feyzi et al. 1997. Structural Requirement of Heparan Sulfate for Interaction with Herpes Simplex Virus Type 1 Virions and Isolated Glycoprotein C. The Journal of Biological Chemistry 272 (40):24850-24857.

Frolov et al. 1996. Alphavirus-based expression vectors: Strategies and applications. Proc. Natl. Acad. Sci. USA 93: 11371-11377.

Garoff et al. 1983. Expression of Semliki Forest Virus Proteins from Cloned Complementary DNA. II. The Membrane-spanning Glycoprotein E2 is Transported to the Cell Surface without its Normal Cytoplasmic Domain. The Journal of Cell Biology 97:652-658.

Geigenmuller-Gnirke et al. "Complementation Between Sindbis Viral RNAs Produces Infectious Particles with a Bipartite Genome" Proceedings of the National Academy of Sciences 88:3253-3257 (1991).

Geisbert et al. "Evaluation in Nonhuman Primates of Vaccines Against Ebola Virus" Emerging Infect. Dis. 8(5):503-507 (2002).

Gingras et al. "Activation of the Translational Supressor 4E-BP1 Following Infection with Encephalomyocarditis Virus and Poliovirus" Proc. Natl. Acad. Sci. USA 93:5578-5583 (1996).

Golzio et al. "Cell Synchronization Effect on Mammalian Cell Permeabilization and Gene Delivery by Electronic Field" Biochim. Biophys. Acta 1563:23-28 (2002).

Gradi et al. "Proteolysis of Human Eukaryotic Translation Initiation Factor eIF4GII, but Not eIF4GI, Coincides ith the Shutoff of Host Protein Synthesis after Poliovirus Infection" Proc. Natl. Acad. Sci. USA 95:11089-11094 (1998).

Grieder et al. 1995. Specific Restrictions in the Progression of Venezuelan Equine Encephalitis Virus-Induced Disease Resulting from Single Amino Acid Changes in the Glycoproteins. Virology 206:994-1006.

Hahn et al. "Infectious Sindbis Virus Transient Expression Vectors for Studying Antigen Processing and Presentation" Proc. Natl. Acad. Sci. USA 89:2679-2683 (1992).

Heidner et al. 1994. Lethality of PE2 Incorporation into Sindbis Virus can be Suppressed by Second-Site Mutations in E3 and E2. Journal of Virology 68:2683-2692.

Heise et al. "An Attenuating Mutation in nsP1 of the Sindbis-Group Virus S.A.AR86 Accelerates Nonstructural Protein Processing and Up-Regulates Viral 26S RNA Synthesis" Journal of Virology 77(2):1149-1156(2003).

Heiser et al. "Autologous Dendritic Cells Transfected with Prostate-Specific Antigen RNA Stimulate CTL Responses Against Metastatic Prostate Tumors" J. Clinical Inv. 109(3):409-417 (2002).

Herweijer et al. 1997. Self-Amplifying Vectors for Gene Delivery. Advanced Drug Delivery Reviews 27:5-16.

Hevey et al. "Marburg Virus Vaccines Based upon Alphavirus Replicons Protect Guinea Pigs and Nonhuman Primates" Virology 251:28-37 (1998).

Hevey et al. 2002. Marburg Virus Vaccines: Comparing Classical and New Approaches. Vaccine 20:586-593.

Hill et al. "RNA-RNA Recombination in Sindbis Virus: Roles of the 3' Conserved Motif, Poly (A) Tail, and Nonviral Sequences of Template RNAs in Polymerase Recognition and Template Switching" Journal of Virology 71:2693-2704 (1997).

Hirsch et al. 1996. Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara. J. Virol. 70(6):3741-3752.

Hodgson et al. 1993. Expression of Venezuelan Equine Encephalitis Virus Proteins by Recombinant Baculoviruses. The American Journal of Tropical Medicine and Hygiene. 49:195-196 (Supplement) (Abstract).

Holcik and Komeluk "Functional Characterization of the X-Linked Inhibitor of Apoptosis (XIAP) Internal Ribosome Entry Site Element: Role of La Autoantigen in XIAP Translation" Molecular and Cellular Biology 20(13):4648-4657 (2000).

Holcik et al. "A New Internal-Ribosome-Entry-Site Motif Potentiates XIAP-Mediated Cytoprotection" Nature Cell Biology 1:190-192(1999).

Holcik et al. "The Internal Ribosome Entry Site-Mediated Translation of Antiapoptotic Protein XIAP is Modulated by the Heterogeneous Nuclear Ribonucleoproteins C1 and C2" Molecular and Cellular Biology 23(1):280-288 (2003).

International Search Report issued for PCT/US03/39723; mailed on Aug. 17, 2004.

International Search Report issued for PCT/US03/39725; mailed on Dec. 3, 2004.

International Search Report of International Application Serial No. PCT/US02/28610 mailed Feb. 11, 2003.

Jalanko "Expression of Semliki Forest Virus Capsid Protein from SV40 Recombinant Virus" FEBS Letters 186:59-64 (1985).

Jang and Wimmer "Cap-Independent Translation of Encephalomyocarditis Virus RNA: Structural Elements of the Internal Ribosomal Entry Site and Involvement of a Cellular 57-kD RNA-Binding Protein" Genes & Development 4:1560-1572 (1990).

Joachims et al. "Cleavage of Poly(A)-Binding Protein by Enterovirus Proteases Concurrent with Inhibition of Translation In Vitro" Journal of Virology 73(1):718-727 (1999).

Johnston and Peters. 1996. Alphaviruses. In: Fields Virology, 3rd ed., Lippincott-Raven Publishers, Philadelphia, Chapt, 28:843-898.

Johnston and Smith. 1988. Selection for Accelerated Penetration in Cell Culture Coselects for Attenuated Mutants of Venezuelan Equine Encephalitis Virus. Virology 162:437-443.

Kinney et al. 1989. The Full-Length Nucleotide Sequences of the Virulent Trinidad Donkey Strain of Venezuelan Equine Encephalitis Virus and its Attenuated Vaccine Derivative, Strain TC-83. Virology 170:19-30.

Kinney et al. 1993. Attenuation of Venezuelan Equine Encephalitis Virus Strain TC-83 Is Encoded by the 5'-Noncoding Region and the E2 Envelope Glycoprotein. Journal of Virology 67:1269-1277.

Klimstra et al. "Adaptation of Sindbis Virus to BHK Cells Selects for Use of Heparan Sulfate as an Attachment Receptor" Journal of Virology 72:7357-7366 (1998).

Koller et al. "A High-Throughput Alphavirus-Based Expression Cloning System for Mammalian Cells" Nature Biotech. 19:851-855 (2001).

Kondor-Koch et al. 1983. Expression of Semliki Forest Virus Proteins from Cloned Complementary DNA. I. The Fusion Activity of the Spike Glycoprotein. J. Cell Biology 97(3):644-651.

Kumamoto et al. "Induction of Tumor-Specific Protective Immunity by in situ Langerhans Cell Vaccine" Nature Biotech. 20:64-69 (2002).

Lee et al. 1997. Efficient Long-Term Coexpression of a Hammerhead Ribozyme Targeted to the U5 Region of HIV-1 LTR by Linkage to the Multidrug-Resistance Gene. Antisense & Nucleic Acid Drug Development 7:511-522.

Leitner et al. "Enhancement of Tumor-Specific Immune Response with Plasmid DNA Replicon Vectors" Cancer Research 60:51-55 (2000).

Lemm et al. 1994. Polypeptide requirements for assembly of functional Sindbis virus replication complexes: a model for the temporal regulation of minus- and plus-strand RNA synthesis. The EMBO Journal 13:2925-2934.

Leone et al. 1985. In Vitro Synthesis of the Gene Coding for the Glycoprotein E1 of Sindbis Virus. Microbiologica 8(2):123-130.

Li et al. "Production of Infectious Recombinant Moloney Murine Leukemia Virus Particles in BHK Cells using Semliki Forest Virus-Derived RNA Expression Vectors" Proc. Natl. Acad. Sci. USA 93:11658-11663 (1996).

Liljestrom et al. "In Vitro Mutagenesis of a Full-Length cDNA Clone of Semliki Forest Virus: the Small 6,000-Molecular-Weight Membrane Protein Modulates Virus Release" Journal of Virology 65:4107-4113 (1991).

Liljeström. 1994. Alphavirus expression systems. Current Opinion in Biotechnology 5:495-500.

Lobigs et al. 1990. Fusion Function of the Semliki Forest Virus Spike is Activated by Proteolytic Cleavage of the Envelope Glycoprotein Precursor p62. Journal of Virology 64:1233-1240.

Lu et al. "Transmission of Replication-Defective Sindbis Helper Vectors Encoding Capsid and Envelope Proteins" Journal of Virological Methods 91(1):59-65 (2001).

Lundström et al. 1985. Secretion of Semliki Forest Virus Membrane Glycoprotein E1 from *Bacillus subtilis* Virus Research 2:69-83.

Martinez-Salas et al. "Functional Interactions in Internal Translation Initiation Directed by Viral and Cellular IRES Elements" Journal of General Virology 82:973-984(2001).

McKnight et al. "Deduced Consensus Sequence of Sindbis Virus Strain AR339: Mutations Contained in Laboratory Strains Which Affect Cell Culture and In Vivo Phenotypes" Journal of Virology 70(3):1981-1989 (1996).

Melancon et al. 1986. Reinitiation of Translocation in the Semliki Forest Virus Structural Polyprotein: Identification of the Signal for the E1 Glycoprotein. The EMBO Journal 5:1551-1560.

Melancon et al. 1987. Processing of the Semliki Forest Virus Structural Polyprotein: Role of the Capsid Protease. Journal of Virology 61:1301-1309.

Morgenstern et al. 1990. Advanced mammalian gene transfer: high titre retroviral vectors with multiple drug slection markers and a complementary helper-free packaging cell line. Nucleic Acids Research 18:3587-3596.

Oker-Blom et al. 1989. Expression of Sindbis Virus 26S cDNA in *Spodoptera frugiperda* (Sf9) Cells, Using a Baculovirus Expression Vector. J. Virology 63:1256-1264.

Olmsted et al. "Characterization of Sindbis Virus Epitopes Important for Penetration in Cell Culture and Pathogenesis in Animals" Virology 148:245-254 (1986).

Orkin et al. 1995. Report and Recommendations of the Panel to Assess the NIH Investment in Research Gene Therapy.

Overwijk et al. "Creating Therapeutic Cancer Vaccines: Notes from the Battlefield" Trends in Immunol. 22(1):5-7 (2001).

Pardoll "Cancer Vaccines" Nature Medicine Vaccine Supplement 4(5):525-531 (1998).

Pardoll "Spinning Molecular Immunology into Successful Immunotherapy" Nature Reviews—Immunology 2:227-238 (2002).

Paredes et al. 1993. Three-dimensional Structure of a Membrane-Containing Virus. Proc. Natl. Acad. Sci. USA 90:9095-9099.

Polo and Johnston. 1990. Attenuating Mutations in Glycoproteins E1 and E2 of Sindbis Virus Produce a Highly Attenuated Strain When Combined in Vitro. Journal of Virology 64:4438-4444.

Polo et al. "Stable Alphavirus Packaging Cell Lines for Sindbis Virus and Semliki Forest Virus-Derived Vectors" Proc. Natl. Acad. Sci. 96:4598-4603 (1999).

Presley et al. 1991. Proteolytic Processing of the Sindbis Virus Membrane Protein Precursor PE2 is Nonessential for Growth in Vertebrate Cells but is Required for Efficient Growth in Invertebrate Cells, Journal of Virology 65:1905-1909.

Ragupathi et al. "The Case for Polyvalent Cancer Vaccines that Induce Antibodies" Expert Rev. Vaccines 1(2):193-206 (2002).

Rice et al. 1985. Expression of Sindbis Virus Structural Proteins via Recombinant Vaccinia Virus: Synthesis, Processing, and Incorporation into Mature Sindbis Virions. J. Virology 56:227-239.

Riedel. 1985. Different Membrane Anchors Allow the Semliki Forest Virus Spike Subunit E2 to Reach the Cell Surface. Journal of Virology 54:224-228.

Roberts and Belsham "Complementaion of Defective Picornavirus Internal Ribosome Entry Site(IRES) Elements by the Coexpression of Fragments of the IRES" Virology 227:53-62 (1997).

Russell et al. 1989. Sindbis Virus Mutations Which Coordinately Affect Glycoprotein Processing, Penetration, and Virulence in Mice, Journal of Virology 63:1619-1629.

Sadanaga et al. "Dendritic Cell Vaccination with MAGE Peptide is a Novel Therapeutic Approach for Gastrointestinal Carcinomas" Clin Cancer Research 7:2277-2284 (2001).

Salminen et al. 1992. Membrane Fusion Process of Semliki Forest Virus II: Cleavage dependent Reorganization of the Spike Protein Complex Controls Virus Entry. The Journal of Cell Biology 116: 349-357.

Schlesinger and Schlesinger. 1996. Togaviridae: The Viruses and Their Replication. In: Fields Virology, 3rd edition. (Fields et al., eds.) Lipincott-Raven Publishers, Philadelphia.

Schlesinger. 1993. Alphaviruses—vectors for the expression of heterologous genes. TiBTech 11:18-22.

Schoepp and Johnston. 1993. Directed Mutagenesis of a Sindbis Virus Pathogenesis Site. Virology 193:149-159.

Simpson et al. 1996. Complete Nucleotide Sequence and Full-Length cDNA Clone of S.A.AR86, a South African Alphavirus Related to Sindbis. Virology 222:464-469.

Sjöberg, et al. 1994. A Significantly Improved Semliki Forest Virus Expression System Based on Translation Enhancer Segments from the Viral Capsid Gene. Bio/Technology 12:1127-1131.

Slepushkin et al. "Large Scale Purification of a Lentviral Vector Size Exclusion Chromatography or Mustang Q Ion Exchange Capsule" Bioprocessing Journal pp. 89-94 (Sep.-Oct. 2003).

Smerdou and Liljestrom. 1999. Two-Helper RNA System for Production of Recombinant Semliki Forest Virus Particles. Journal of Virology 73(2):1092-1098.

Strauss and Strauss. 1990. Alphavirus Proteinases. Seminars In Virology 1:347-356.

Strauss et al. 1994. The Alphaviruses: Gene Expression, Replication, and Evolution. Microbiological Reviews 58:491-562.

Suomalainen et al. 1992. Spike Protein-Nucleocapsid Interactions Drive the Budding of Alphaviruses. Journal of Virology 66(8):4737-4747.

Sykes and Johnston. 1999. Genetic Live Vaccines Mimic the Antigenicity but Not Pathogenicity of Live Viruses. DNA and Cell Biology. 18(7):521-531.

Technical Bulletin No. 166: RiboMAX Large Scale RNA Production Systems—SP6 and T7; Promega Corporation p. 1-11; Revised Sep. 2001; http://www.promega.com/tbs/tb166.pdf on Nov. 4, 2004.

Thompson and Sarnow "Enterovirus 71 Contains a Type I IRES Element that Functions When Eukaryotic Initiation Factor eIF4G is Cleaved" Virology 315:259-266 (2003).

Ubol et al. 1994. Neurovirulent Strains of Alphavirus Induce Apoptosis in bcl-2-expresing Cells: Role of a Single Amino Acid Change in the E2 Glycoprotein. Proc. National Academy Sciences 91:5202-5206.

Van der Velden et al. "Defective Point Mutants of the Encephalomyocarditis Virus Internal Ribosome Entry Site can be Complemented in Trans" Virology 214:82-90 (1995).

Verma et al. 1997. Gene Therapy—Promises, Problems and Prospects. Nature 389:239-242.

Waite et al. "Inhibition of Sindbis Virus Production by Media of Low Ionic Strength: Intracellular Events and Requirements for Reversal" Journal of Virology 5:60-71 (1970).

Ward et al. "Immunotherapeutic Potential of Whole Tumor Cells" Cancer Immunol. Immunother. 51:351-357 (2002).

Weiss and Schlesinger. 1991. Recombination between Sindbis Virus RNAs. Journal of Virology 65: 4017-4025.

Wen et al. 1986. Expression of Genes Encoding Vesicular Stomatitis and Sindbis Virus Glycoproteins in Yeast Leads to Formation of Disulfide-Linked Oligomers. Virology 153:150-154.

Williamson et al. "Characterization and Selection of HIV-1 Subtype C Isolates for Use in Vaccine Development" AIDS Research and Human Retroviruses 19(2):133-144 (2003).

Williamson et al. "Designing HIV-1 Subtype C Vaccines for South Africa" South African Journal of Science 96:318-324 (2000).

Wilson et al. "Vaccine Potential of Ebola Virus VP24, VP30, VP35 and VP40 Proteins" Virology 286:384-390 (2001).

Xiong et al. 1989. Sindbis Virus: An Efficient, Broad Host Range Vector for Gene Expression in Animal Cells. Science 243:1188-1191.

Yamanaka et al. "Enhancement of Antitumor Immune Response in Glioma Models in Mice by Genetically Modified Dendritic Cells Pulsed with Semliki Forest Virus-Mediated Complementary DNA" J. Neurosurgery 94:474-481 (2001).

Yamanaka et al. "Marked Enhancement of Antitumor Immune Responses in Mouse Brain Tumor Models by Genetically Modified Dendritic Cells Producing Semliki Forest Virus-Mediated Interleukin-12" J. Neurosurgery 97:611-618 (2002).

Yang and Sarnow "Location of the Internal Ribosome Entry Site in the 5' Non-Coding Region of the Immunoglobulin Heavy-Chain Binding Protein (BiP) mRNA: Evidence for Specific RNA-Protein Interactions" Nucleic Acids Research 25(14):2800-2807 (1997).

Ying et al. "Cancer Therapy Using a Self-Replicating RNA Vaccine" Nature Medicine 5(7):823-827 (1999).

Zhao et al. 1992. Role of Cell Surface Spikes in Alphavirus Budding. Journal of Virology 66:7089-7095.

Gidwitz et al. "Differences in virion stability among Sindbis virus pathogenesis mutants" Virus Research 10:225-240 (1988).

Johnston et al. "Studies of Alphavirus Virulence Using Full-Length Clones of Sindbis and Venezuelan Equine Encephalitis Viruses" M.A. Brinton et al. (eds), New Aspects of Positive Strand RNA Viruses, pp. 334-339, ASM Press (1990).

Kaufman et al. "Improved vectors for stable expression of foreign genes in mammalian cells by use of the untranslated leader sequence from EMC virus" Nucleic Acids Research 19(16):4485-4490 (1991).

Khromykh. "Replicon-based vectors of positive strand RNA viruses" Current Opinion in Molecular Therapeutics 2(5):555-569 (2000).

Lemm et al. "Assembly of Functional Sindbis Virus RNA Replication Complexes: Requirement for Coexpression of P123 and P34" Journal of Virology 67(4):1905-1915 (1993).

Olmsted et al. "Sindbis Virus Mutants Selected for Rapid Growth in Cell Culture Display Attenuated Virulence in Animals" Science 225(4660):424-427 (1984).

Polo et al. "A Model for In Vitro Development of Live, Recombinant Alphavirus Vaccines" Vaccines 90: Modern Approaches to New Vaccines Including Prevention of AIDS, pp. 105-108, Brown et al. (eds), Cold Spring Harbor Laboratory, 1990.

Polo et al. "Mutational Analysis of Virulence Locus in the E2 Glycoprotein Gene of Sindbis Virus" Journal of Virology 65(11):6358-6361 (1991).

* cited by examiner

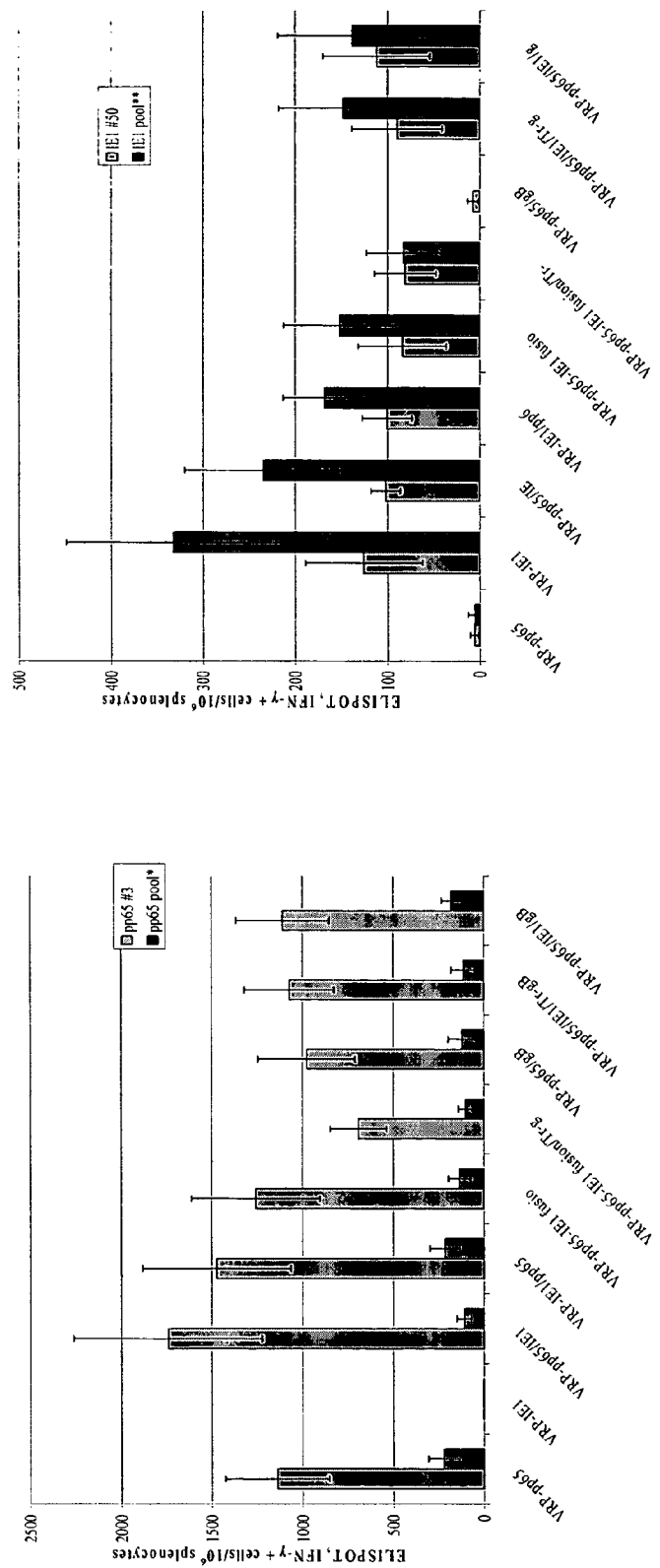
Figs. 3A-B

ALPHA VIRUS-BASED CYTOMEGALOVIRUS VACCINES

RELATED APPLICATIONS

The present application claims the benefit, under 35 U.S.C. § 119(e), of U.S. provisional application Ser. No. 60/486,501, filed Jul. 11, 2003, the entire contents of which are incorporated by reference herein.

BACKGROUND OF THE INVENTION

Human cytomegalovirus (HCMV) is a herpesvirus that causes widespread infection found across all geographic locations and socio-economic groups, with up to 85% of adults infected by age 40 in the United States. For most healthy people who acquire the virus after birth there are no long-term consequences. However, the risk of HCMV infection is significant for several high-risk groups including: (i) unborn children, (ii) adults who work with children, and (iii) immuno-compromised persons. The prevalence of these risk groups underlies the importance of the development of a safe and efficacious vaccine.

HCMV is typically secreted via a number of bodily fluids, e.g., saliva, urine and semen. Thus, transmission of the virus between people can occur through either sexual or non-sexual contact. An individual can contract HCMV through blood or organ transplants, and a mother can transmit it to her unborn fetus.

The virus demonstrates a life-long latency, but is most commonly non-symptomatic in healthy individuals. It sometimes can cause an illness with symptoms similar to those associated with mononucleosis. However, it can cause severe illness in immunocompromised individuals, e.g., transplant recipients or those with acquired immunodeficiency syndrome (AIDS), in addition to the severe, debilitating effects on unborn children whose immune systems have not yet matured.

In the case of transplants, bone marrow transplant recipients show a relatively high incidence of HCMV-induced pneumonia, with consequent high mortality among these patients. In solid organ transplant patients, disease triggered by HCMV can include a HCMV syndrome (consisting of fever and leucopenia), hepatitis, colitis and pneumonia. HCMV-induced disease in these transplant recipients is caused by the immunosuppressive effects of the drugs required for transplant acceptance and the induction of graft vs. host disease (GVHD). The GVHD effect is most severe in those instances where the organ/marrow donor is HCMV seropositive and the recipient is HCMV seronegative.

For AIDS patients, HCMV is the most common opportunistic infection, in large part due to the fact that greater than 90% of HIV-infected individuals are co-infected with HCMV. In these patients, the infection most commonly manifests as retinitis, and usually occurs when the CD4+ cell counts are less than 50/µl. Prior to the adoption of highly active antiretroviral (HAART) protocols, 20-44% of AIDS patients developed HCMV disease. While the use of HAART has also resulted in the reduction of HCMV disease, the unavailability of HAART for many AIDS patients, as well as the inability of many patients to tolerate HAART for extended periods of time, make the possibility of HCMV disease a continuing concern.

Congenital HCMV, a result of mother-to-fetus transmission, occurs at an overall rate of approximately 1%, but rates are much higher and symptomatic disease is more common when the mother has a primary infection. Women can be infected via sexual contact, since shedding of the virus from the cervix and in semen is common. Infected infants can remain viremic for up to five years after birth, becoming an important source for infection in day care settings.

Congenital HCMV can have horrific manifestations in infants. A fulminant cytomegalic inclusion disease can develop, characterized by jaundice, petechial rash, hepatosplenomegaly, microcephaly, and chorioretinitis. There is often progressive hearing loss and mental retardation, which can be severe. The estimated costs to society in terms of care for victims of congenital HCMV are approximately four billion dollars.

Thus, there remains a clear need for a safe and effective vaccine to combat HCMV infection, both prophylactically (for example, in adolescents or women of child-bearing potential to prevent congenital infection or in HCMV-uninfected transplant candidates) and therapeutically (for example, in HCMV-infected transplant patients prior to and after transplantation of an organ or bone marrow).

BRIEF DESCRIPTION OF THE DRAWINGS

FIGS. 3A-B show the results of an IFN-γ ELISPOT assay following immunization of mice with CMV-VRP vaccines. FIG. 3A shows the results obtained by using peptide pp65 #3 and a pp65 peptide pool to evaluate cellular immune responses. FIG. 3B shows the results obtained by using peptide IE1 #50 and an IE1 peptide pool to evaluate cellular immune responses.

SUMMARY OF THE INVENTION

Figure 1:
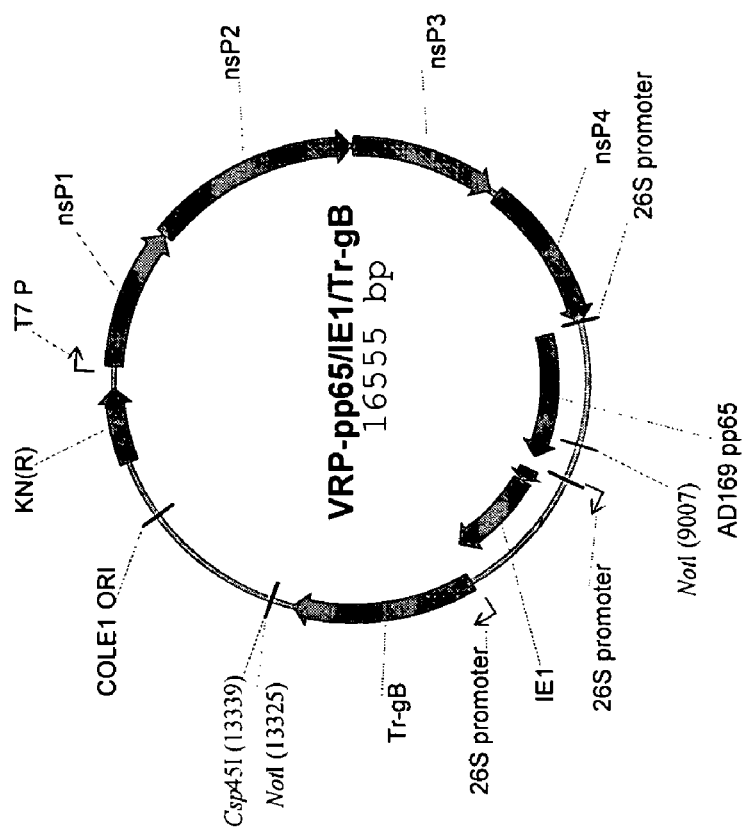
FIG. 1 is a diagram of the replicon vector VRP-pp65/IE1/Tr-gB.

The present invention provides a population of alphavirus replicon particles wherein said particles comprise alphavirus replicon RNAs, wherein a first replicon RNA comprises nucleic acid encoding cytomegalovirus pp65 and IE1 proteins or immunogenic fragments thereof, and a second replicon RNA comprises nucleic acid encoding cytomegalovirus gB protein or an immunogenic fragment thereof, and wherein each of the first and second replicon RNAs is contained within a separate alphavirus replicon particle.

Further provided herein is a population of alphavirus replicon particles wherein said particles comprise a replicon RNA which comprises a regulatory cassette that directs transcription and translation of a nucleic acid encoding cytomegalovirus pp65 and IE1 proteins, or immunogenic fragments thereof.

In additional embodiments, the present invention provides a population of alphavirus replicon particles wherein the particles comprise an alphavirus replicon RNA comprising nucleic acid encoding a CMV polypeptide selected from the group consisting of pp65, IE1, and gB, immunogenic fragments thereof or any combination thereof.

Also provided herein is a population of alphavirus replicon particles, wherein the particles comprise an alphavirus replicon RNA comprising nucleic acid encoding cytomegalovirus pp65 and gB proteins, or immunogenic fragments thereof.

The present invention also provides a population of alphavirus replicon particles comprising an alphavirus replicon RNA, wherein the replicon RNA of each particle comprises a first nucleic acid encoding cytomegalovirus pp65 protein or an immunogenic fragment thereof and a second nucleic acid encoding cytomegalovirus IE1 protein or an immunogenic fragment thereof, and wherein the expression of the first and second nucleic acid is controlled by separate regulatory cassettes.

Also provided herein are methods of inducing an immune response to CMV in a subject, comprising administering to the subject an effective amount of the populations of this invention.

Further provided is a method for inducing an immune response to CMV in a subject, comprising: a) priming the subject's immune system by administering to the subject an effective amount of a first immunizing component selected from the group consisting of: alphavirus replicon particles encoding CMV immunogens, CMV immunogens, nucleic acid molecules encoding CMV immunogens, a non-alphavirus viral vector encoding CMV immunogens, and any combination thereof; and b) boosting the subject's priming response by administering to the subject an effective amount of a second immunizing component selected from the group consisting of: alphavirus replicon particles encoding CMV immunogens, CMV immunogens, nucleic acid molecules encoding CMV immunogens, a non-alphavirus viral vector encoding CMV immunogens, and any combination thereof, wherein the first immunizing component is different from the second immunizing component and wherein at least the first immunizing component or the second immunizing component is an alphavirus replicon particle encoding CMV immunogens.

DETAILED DESCRIPTION OF THE INVENTION

As used herein, "a," "an," or "the" can mean one or more than one. For example, "a cell" can mean one cell or a plurality of cells.

"Alphavirus" means a genus of viruses, all of which are members of the Togaviridae family. Known alphaviruses include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African arbovirus 86 (S.A.AR86) Semliki Forest virus, Middleburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus. The alphaviral genome is a single-stranded, messenger-sense RNA, modified at the 5'-end with a methylated cap and at the 3'-end with a variable-length poly (A) tract. Structural subunits containing a single viral protein, capsid, associate with the RNA genome in an icosahedral nucleocapsid. In the virion, the capsid is surrounded by a lipid envelope covered with a regular array of transmembrane protein spikes, each of which consists of a heterodimeric complex of two glycoproteins, E1 and E2. See Pedersen et al., *J. Virol* 14:40 (1974). The Sindbis and Semliki Forest viruses are considered the prototypical alphaviruses and have been studied extensively. See Schlesinger, *The Togaviridae and Flaviviridae*, Plenum Publishing Corp., New York (1986). The preferred alphaviruses used in the constructs and methods of the claimed invention are VEE, S.AAR86, Sindbis (e.g., TR339, see U.S. Pat. No. 6,008,035), and Semliki Forest Virus.

Within each named alphavirus, strains and/or subtypes are known. For example, several strains of the Venezuelan Equine Encephalitis virus (VEE) are known. Within the known strains of VEE, subtypes have been recognized. For example, the Trinidad Donkey strain is in subtype IA/B, and related subtypes include IC and IE. Virulent VEE strains have been isolated during mosquito-borne epizootic encephalomyelitis in equids in tropical and sub-tropical areas of the New World. The Trinidad Donkey strain is one of the virulent, epizootic strains, and it was passaged serially in tissue culture to create a live, attenuated strain (Berge et al. *Amer. J Hyg.* 73:209-218 (1961)) known as TC-83. This strain, containing multiple attenuating mutations (see below, and Kinney et al. 1989 *Virology* 170:19-30 (1989); with correction noted in Kinney et al. *J Virol* 67(3):1269-1277 (1993)) elicits VEE-specific neutralizing antibodies in most humans and equines and has been used successfully as a vaccine in both species (e.g., Pittman et al. *Vaccine* 14(4):337-343 (1996)). Thus, the TC-83 strain of VEE can also serve as the genetic background for an alphavirus replicon vector system as described herein.

The terms "alphavirus RNA replicon," "alphavirus replicon RNA," "alphavirus replicon vector" and "alphavirus RNA vector replicon" are used interchangeably to refer to an RNA molecule expressing nonstructural protein genes such that it can direct its own replication (amplification) and comprises, at a minimum, the 5' and 3' alphavirus replication recognition sequences, coding sequences for alphavirus nonstructural proteins, and a polyadenosine tract. It may additionally contain a regulatory cassette and a heterologous nucleic acid of interest that is expressed from the regulatory cassette. It may also be engineered to express one but not all alphavirus structural proteins.

Specific embodiments of the alphavirus RNA replicons utilized in the claimed invention may contain one or more "attenuating mutations," an attenuating mutation being a nucleotide deletion, addition, or substitution of one or more nucleotide(s), or a mutation that comprises rearrangement or chimeric construction which results in a loss of virulence in a live virus containing the mutation as compared to the appropriate wild-type alphavirus. Several examples of attenuating mutations have been previously described in U.S. Pat. Nos. 5,639,650, 5,792,462 and 6,156,558. Specific attenuating mutations for the VEE E1 glycoprotein can include an attenuating mutation at any one of E1 amino acid positions 81, 272 and/or 253. Alphavirus particles made from the VEE-3042 mutant contain an isoleucine substitution at E1-81, and virus particles made from the VEE-3040 mutant contain an attenuating mutation at E1-253. Specific attenuating mutations for the VEE E2 glycoprotein can include an attenuating mutation at any one of E2 amino acid positions 76, 120, and/or 209. Alphavirus particles made from the VEE-3014 mutant contain attenuating mutations at both E1-272 and at E2-209 (see U.S. Pat. No.5,792,492). A specific attenuating mutation for the VEE E3 glycoprotein includes an attenuating mutation consisting of a deletion of E3 amino acids 56-59. Virus particles made from the VEE-3526 mutant, now being developed as a vaccine strain, contain this deletion in E3 (aa56-59) as well as a second attenuating mutation at E1-253.

Specific attenuating mutations for the S.A.AR86 E2 glycoprotein include an attenuating mutation at any one of E2 amino acid positions 304, 314, 372, and/or 376 (see U.S. Pat. No. 5,639,650). Alternatively, the attenuating mutation can be a substitution, deletion and/or insertion of an amino acid in the E2 glycoprotein, for example, at any one or more of the following amino acid positions in any combination: 158, 159, 160, 161 and/or 162 (see Polo et al., PCT Publication No. WO 00/61772, the entire contents of which are incorporated by reference herein).

Attenuating mutations can also be present in the alphavirus non-structural proteins, nsp1-nsp4. Exemplary attenuating mutations in the non-structural proteins for S.A.AR86 include, but are not limited to, codons which specify an attenuating amino acid at any one or more of the following: nsp1 amino acid position 538, nsp2 amino acid position 96, nsp2 amino acid position 372, nsp2 amino acid position 529; nsp2 amino acid position 571; nsp2 amino acid position 682; nsp2 amino acid position 804, nsp3 amino acid position 22, and in combination, codons at nsp2 amino acid positions 529, 571, 682 and 804 and at nsp3 amino acid position. Other illustrative attenuating mutations for S.A.AR86 include those described in PCT Application No. PCT/US01/27644.

Another type of attenuating mutation of this invention can be one or more attenuating mutations in the non-translated regions of the alphavirus genome which cause a loss in virulence in a live virus containing such mutations (e.g., see Niesters and Strauss "Defined mutations in the 5' non-translated sequence of Sindbis virus RNA" *J Virol* 64: 4162-4168 (1990)). One example of such a mutation is at nucleotide 3 of the VEE genomic RNA, i.e., the third nucleotide following the 5' methylated cap (see, e.g., U.S. Pat. No. 5,643,576, describing a G→C mutation at nt 3; and White et al. "Role of alpha/beta interferon in Venezuelan Equine Encephalitis virus pathogenesis: effect of an attenuating mutation in the 5' untranslated region" *J Virol* 75:2706-2718 (2000)). The mutation can be a G→A, U or C, but the G→A mutation is preferred for some embodiments.

The term "alphavirus structural protein/protein(s)" refers to one or a combination of the structural proteins encoded by an alphavirus. These are produced by the virus as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, PE2, E3-E2, 6k-E2, or E3-6k-E2. As discussed above for the replicon, specific embodiments of the alphavirus structural proteins utilized in the claimed invention may contain one or more attenuating mutations, an attenuating mutation being a nucleotide deletion, addition, and/or substitution of one or more nucleotide(s), or a mutation that comprises rearrangement or chimeric construction which results in a loss of virulence in a live virus containing the mutation as compared to the appropriate wild-type alphavirus.

The terms "alphavirus replicon particles (ARPs)," "virus replicon particles," and "recombinant alphavirus particles," used interchangeably herein, mean a virion-like structural complex incorporating an alphavirus replicon RNA that expresses one or more heterologous RNA sequences. Typically, the virion-like structural complex includes one or more alphavirus structural proteins embedded in a lipid envelope enclosing a nucleocapsid that in turn encloses the RNA. The lipid envelope is typically derived from the plasma membrane of the cell in which the particles are produced. Preferably, the alphavirus replicon RNA is surrounded by a nucleocapsid structure comprised of the alphavirus capsid protein, and the alphavirus glycoproteins are embedded in the cell-derived lipid envelope. ARPs are infectious but propagation-defective, i.e., the replicon RNA cannot propagate beyond the host cell into which the particles initially infect, in the absence of the helper nucleic acid(s) encoding the alphavirus structural proteins. The structural proteins and replicon RNA of the ARPs may be derived from the same or different alphaviruses. In one embodiment, the replicon RNA and the structural proteins are both derived from VEE, and such particles are sometimes referred to herein as "VRP" or "VRPs". In another embodiment, the replicon RNA is derived from VEE and the structural proteins are derived from Sindbis virus (see, e.g., Dubensky et al., U.S. Pat. No. 6,376,236).

The term "helper(s)" refers to one or more nucleic acid molecules capable of being expressed to produce one or more alphavirus structural proteins. The helpers can be RNA or DNA molecules. In one embodiment, the helper is a single DNA molecule comprising a promoter capable of directing the expression of nucleic acid encoding all the structural proteins of the alphavirus. In another embodiment, the helper comprises two RNA molecules that together express nucleic acid encoding all the alphavirus structural proteins. These two RNA molecules can be produced in vitro, or they can be generated from a single DNA helper that resolves itself into two separate molecules in vivo. In the case of the DNA helper constructs that do not employ alphaviral recognition signals for replication and transcription, the theoretical frequency of recombination is lower than the bipartite RNA helper systems that employ such signals.

The terms "helper cell" and "packaging cell" are used interchangeably herein and refer to the cell in which alphavirus replicon particles are produced. The helper cell comprises a set of helpers that encode one or more alphavirus structural proteins. As disclosed herein, the helpers may be RNA or DNA. The cell can be any cell that is alphavirus-permissive, i.e., cells that are capable of producing alphavirus particles upon introduction of a viral RNA transcript. Alphavirus-permissive cells include, but are not limited to, Vero, baby hamster kidney (BHK), 293, 293T, chicken embryo fibroblast (CEF), and Chinese hamster ovary (CHO) cells. In certain embodiments of the claimed invention, the helper or packaging cell may additionally include a heterologous RNA-dependent RNA polymerase and/or a sequence-specific protease.

The term "immunogenic fragment" means a fragment (e.g., a peptide) of a CMV protein that can stimulate either humoral or cellular immune responses in the host.

To stimulate the humoral arm of the immune system, i.e., the production of antigen-specific antibodies, an immunogenic fragment can include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between five amino acids and the full-length sequence, provided that the fragment in question retains immunogenic activity, as measured by any art-known assay, such as the ones described herein.

Regions of a given polypeptide that include an epitope can be identified using any number of epitope mapping techniques, well known in the art. (See, e.g., *Epitope Mapping Protocols in Methods in Molecular Biology*, Vol. 66, Glenn E. Morris, Ed., 1996, Humana Press, Totowa, N.J.) For example, linear epitopes can be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci.* USA 81:3998-4002; Geysen et al. (1986) *Molec. Immunol.* 23:709-715, all incorporated herein by reference in their entireties.

Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci* USA (1 981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids, and these are not typically predicted by the above-described methods for identifying humoral epitopes. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenic fragments can also be identified based on their ability to stimulate lymphocyte proliferation in response to stimulation by various fragments from the antigen of interest.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence or stimulates a cellular immune response. There is no critical upper limit to the length of the fragment, which can comprise nearly the full-length of the protein sequence, or even a fusion protein comprising two or more epitopes from a single or multiple CMV proteins. An epitope for use in the subject invention is not limited to a polypeptide having-the exact sequence of the portion of the parent protein from which it is derived. Indeed, there are many known strains or isolates of CMV and the virus retains the ability to continue to adapt, and there are several variable domains in the virus that exhibit relatively high degrees of variability between isolates. Thus the term "epitope" encompasses sequences identical to the native sequence, as well as modifications to the native sequence, such as deletions, additions and substitutions (generally, but not always, conservative in nature).

The term "regulatory cassette" means a nucleic acid sequence encoding one or more elements necessary to direct transcription and/or translation of a nucleic acid encoding one or more polypeptides. In one embodiment, the regulatory cassette comprises only an alphavirus subgenomic promoter to direct transcription of a cytoplasmically located RNA that is then capped, and the capped end of the RNA directs translation of the subgenomic RNA. In another embodiment, the regulatory cassette comprises an internal ribosome entry site, or IRES, which directs translation of a downstream coding region. In another embodiment, the regulatory cassette comprises an alphavirus subgenomic promoter and an IRES, and it is engineered to allow the subgenomic promoter to direct transcription (and thus amplification) of the RNA sequence downstream from the promoter and to allow the IRES to direct translation of the subgenomic RNA.

"IRES" means an internal ribosome entry site. IRES sequences have been found in numerous transcripts from viruses that infect vertebrate and invertebrate cells as well as in transcripts from vertebrate and invertebrate genes. Examples of IRES elements suitable for use in this invention include: viral IRES elements from Picornaviruses e.g., poliovirus (PV), encephalomyocarditis virus (EMCV), foot-and-mouth disease virus (FMDV), from Flaviviruses e.g. hepatitis C virus (HCV), from Pestiviruses e.g., classical swine fever virus (CSFV), from Retroviruses e.g., murine leukemia virus (MLV), from Lentiviruses e.g., simian immunodeficiency virus (SIV), or cellular mRNA IRES elements such as those from translation initiation factors e.g., eIF4G or DAP5, from Transcription factors e.g., c-Myc (Yang and Samow, *Nucleic Acids Research* 25:2800-2807 1997) or NF-κB-repressing factor (NRF), from growth factors e.g., vascular endothelial growth factor (VEGF), fibroblast growth factor (FGF-2), platelet-derived growth factor B (PDGF B), from homeotic genes e.g., *Antennapedia*, from survival proteins e.g. X-Linked inhibitor of apoptosis (XIAP) or Apaf-1, or chaperones e.g. the immunoglobulin heavy-chain binding protein BiP (reviewed in Martinez-Salas et al., *Journal of General Virology* 82:973-984 (2001)).

Preferred IRES sequences that can be utilized in these embodiments are derived from: encephalomyocarditis virus (EMCV, ATCC accession #NC001479), cricket paralysis virus (accession #AF218039), Drosophila C virus ATCC accession #AF014388, *Plautia stali* intestine virus (ATCC accession #AB00653 1), *Rhopalosiphum padi* virus (ATCC accession #AF022937), Himetobi P virus (ATCC accession #AB017037), acute bee paralysis virus (ATCC accession #AF150629), Black queen cell virus (ATCC accession #AF183905), Triatoma virus (ATCC accession #AF178440), *Acyrthosiphonpisum* virus (ATCC accession #AF024514), infectious flacherie virus (ATCC accession #AB000906), and Sacbrood virus (ATCC accession #AF092924). In addition to the naturally occurring IRES elements listed above, synthetic IRES sequences, designed to mimic the function of naturally occurring IRES sequences, can also be used. When more than one IRES is used in a replicon construct, the IRES elements may be the same or different.

"Boost" or "Booster" means a second immunization, after an initial (or "priming") immunization that enhances the immune response of the host. In one embodiment, the invention specifically provides a composition which produces an anamnestic response against a herpesvirus, e.g., CMV infection, in a sensitized subject, e.g., a horse, cow, or human, comprising an anamnestic response-inducing amount of a herpesvirus, e.g., CMV, immunizing component. As used herein, the term "anamnestic response" means a secondary (booster) immune response in a sensitized subject. By "sensitized subject" is meant a subject that has previously been in contact with herpesvirus, e.g., CMV, antigens either by natural exposure to the virus or by vaccination (primary immunization) with herpesvirus immunizing components, e.g., CMV-expressing alphavirus replicon particles.

At 230 kilobasepairs of double-stranded DNA, the cytomegalovirus genome is the largest β-herpesvirus known to infect humans. It has over 200 open reading frames responsible for encoding at least 165 genes; these are arranged in two segments, referred to as unique long ($U_L$) and unique short ($U_S$), which are separated by inverted repetitive nucleotide sequences. Thus, the choice of potential antigens to be used in a vaccine is quite large.

Some suggestions regarding vaccine approaches can be obtained from responses of healthy, seropositive individuals. In these individuals, 92% have CTLs present that target the pp65 antigen, 76% have CTLs to the IE1 antigen, 33% to the gB antigen, and 30% to the pp150 antigen (Gyulaj et al. 2000 *J. Infectious Diseases* 181:1537). In contrast, when this cell-mediated immunity is suppressed, the manifestations of HCMV disease are most severe. In addition, the reproductive number (number of cells infected by virus released from one infected cell) is reduced 2 to 7 times in HCMV-experienced hosts. Replication of HCMV in HCMV-experienced immuno-compromised hosts is delayed compared to HCMV-naïve hosts (doubling time 0.38 days and 1.12 days, respectively). As a corollary, cellular responses to pp65 and IE1 have also been demonstrated to protect from CMV infection in animal models using the homologs of the HCMV genes encoding pp65 and IE1 (see Morello et al. *J. Virol.* 2000 Vol 74:3696). Finally, adoptive transfer of pp65-specific CTLs to bone-marrow transplant recipients protects them from CMV disease (Greenberg, P., Keystone Symposium April 2001; see also Walter et al., *N Engl J Med* 1995, 333:1038).

Antibodies to glycoprotein B (gB) are also present in HCMV infected individuals; these antibodies are neutralizing and have been implicated in protection of newborns from primary infection in animal models (Bourne et al. 2001 *J. Infectious Diseases* 183:59; Chatterjee et al. 2001 *J. Infectious Diseases* 183: 1547). Thus, it is expected that a preferred vaccine for humans provides both cellular and humoral immunity in order to be efficacious. Live, attenuated vaccines using the Towne strain of HCMV have been used in transplant patients to reduce the severity of transplant-induced CMV in those seronegative recipients who received a seropositive kidney (Plotkin 1994 *Transplantation* 58:1176). However, because of concerns regarding the safety of live, attenuated vaccines derived from a virus that causes a chronic, persistent infection that can be transmitted to the fetus, and that can be reactivated during periods of immunosuppression, alternative approaches are preferred.

The alphavirus replicon vector system provides the opportunity to induce robust humoral and cellular immunity in humans. The replicon vector system is based on the replication machinery of an alphavirus, consisting of a replicon RNA vector and one or more helper nucleic acids (reviewed in Rayner et al. (2002) *Rev. Med. Virol.* 12:279-96; see also U.S. Pat. Nos. 5,792,462; 6,156,558; Pushko et al. (1997) *Virology* 239:389-401; U.S. patent Publication No. 20020141975; PCT Publication No. WO 03/023026; the entire contents of which are incorporated herein by reference). The replicon RNA contains sequences required for replication and packaging of the RNA into a virus-like particle. It expresses the nonstructural proteins required for genome replication and transcription of subgenomic RNA (if such constructs are utilized), but lacks the structural protein genes necessary for formation of viral particles. The replicon is engineered so that a regulatory cassette can direct the expression of a nucleic acid of interest, in this invention, one ore more nucleic acids encoding CMV polypeptides or immunogenic fragments thereof. One or more helper nucleic acids encode the alphavirus capsid and glycoproteins. When the replicon RNA vector and the one or more helper nucleic acids are introduced into an alphavirus-permissive cell, the replicon RNA is packaged into virus-like particles, which are harvested and purified to produce an immunogen, i.e., a vaccine composition.

In one embodiment, a replicon based on the Venezuelan Equine Encephalitis (VEE) virus is used as the vector for the CMV polypeptides. Nucleic acids encoding CMV proteins gB (e.g., from Towne strain), IE1 and pp65 (e.g., from AD169 strain) can be cloned into the alphavirus vector, e.g., the VEE vector, individually or in various combinations. Such combinations can encompass nucleic acid sequences encoding fusion proteins, e.g., IE1 and pp65 (or immunogenic fragments thereof) or they can encompass multiple regulatory cassettes within a single replicon, wherein each cassette drives either a single coding sequence or a nucleic acid sequence encoding a fusion protein of two or more CMV polypeptides, or immunogenic fragments thereof.

In one embodiment, each desired immunogen (i.e., a CMV polypeptide or an immunogenic fragment thereof) can be encoded by nucleic acid expressed in a separate alphavirus replicon particle, and mixtures of two or more ARPs, each comprising nucleic acid encoding a single CMV immunogen, can be prepared and administered to a subject. This invention therefore encompasses compositions comprising populations of one, two or three (or more) different ARPs. For example, in the case of three different ARPs, each ARP encodes a single CMV polypeptide, e.g., IE1, pp65, and gB (or immunogenic fragments thereof) and each ARP does not encode the other CMV polypeptides. In the case of two different ARPs, one ARP can express two CMV polypeptides, e.g., IE1 and pp65, either as fusion proteins or under the control of separate regulatory cassettes, as described above, and the second ARP can express one CMV polypeptide that is different, e.g., gB. Alternatively, a first ARP can express IE1 and a second ARP can express pp65. In another embodiment of a composition comprising two different ARPs, a first ARP can express pp65 and the second ARP can express gB. In an embodiment employing a single ARP, the replicon vector can include one regulatory cassette directing the expression of a nucleic acid encoding a fusion protein comprising at least pp65 and IE1, and in a specific embodiment, further comprising nucleic acid encoding gB. In another embodiment of the single ARP, one regulatory cassette can direct the expression of nucleic acid encoding gB, a second regulatory cassette can direct the expression of nucleic acid encoding IE1, and a third regulatory cassette can direct the expression of nucleic acid encoding pp65. The regulatory cassette (RC)-encoding nucleic acid components can be in any order, e.g., RC-gB/RC-IE1/RC-pp65, and/or RC-pp65/RC-IE1/RC-gB. In another embodiment of the single ARP, a first regulatory cassette can direct the expression of a nucleic acid encoding a pp65-IE1 fusion protein, and a second RC can direct the expression of nucleic acid encoding gB. In all of the embodiments described herein, the use of the terms "pp65," "IE1 ," and "gB" are meant to encompass the full-length polypeptides, immunogenic fragments, and/or epitopes thereof. Nucleic acid sequences can be cloned from known CMV virus strains, e.g., Towne and AD169, and/or they can be synthetic sequences representing consensus sequences of the CMV sequences or epitopes from one or more CMV polypeptides, or chimeric sequences including fragments or epitopes from different CMV strains.

Thus, in certain embodiments, the present invention provides a population of alphavirus replicon particles wherein said particles comprise alphavirus replicon RNAs, wherein a first replicon RNA comprises nucleic acid encoding cytomegalovirus pp65 and IE1 proteins or immunogenic fragments thereof, and a second replicon RNA comprises nucleic acid encoding cytomegalovirus gB protein or an immunogenic fragment thereof, and wherein each of the first and second replicon RNAs is contained within a separate alphavirus replicon particle. In some embodiments, the first replicon RNA can direct transcription and translation of the nucleic acid encoding cytomegalovirus pp65 and IE1 proteins or immunogenic fragments thereof from two separate regulatory cassettes, whereby a first regulatory cassette directs transcription and translation of the CMV pp65-encoding nucleic acid and a second regulatory cassette directs replication and translation of the CMV IE1-encoding nucleic acid. In certain embodiments, the replicon RNAs of the particles of this population can further encode a CMV gB protein, and/or immunogenic fragment thereof and production of the CMV gB protein can be under the control of a separate, third regulatory cassette.

Further provided herein is a population of alphavirus replicon particles wherein the particles comprise a replicon RNA that comprises a regulatory cassette that directs transcription and translation of a nucleic acid encoding cytomegalovirus pp65 and IE1 proteins, or immunogenic fragments thereof.

Additionally provided herein is a population of alphavirus replicon particles wherein the particles comprise an alphavirus replicon RNA comprising nucleic acid encoding a CMV polypeptide selected from the group consisting of pp65, IE1, and gB, immunogenic fragments thereof or any combination thereof.

In further embodiments, the present invention provides a population of alphavirus replicon particles, wherein the particles comprise an alphavirus replicon RNA comprising nucleic acid encoding-cytomegalovirus pp65 and gB proteins, or immunogenic fragments thereof. In some embodiments, this population can comprise alphavirus replicon RNA wherein the expression of the nucleic acid encoding cytomegalovirus pp65 and the expression of the nucleic acid encoding gB protein is controlled by separate regulatory cassettes.

A population of alphavirus replicon particles is also provided herein, comprising an alphavirus replicon RNA, wherein the replicon RNA of each particle comprises a first nucleic acid encoding cytomegalovirus pp65 protein or an immunogenic fragment thereof and a second nucleic acid encoding cytomegalovirus IE1 protein or an immunogenic fragment thereof, and wherein the expression of the first and second nucleic acid is controlled by separate regulatory cassettes.

In embodiments of this invention wherein the replicon RNAs direct expression of nucleic acid encoding CMV proteins and/or immunogenic fragments thereof of this invention from separate regulatory cassettes (e.g., one, two or three regulatory cassettes present on the same replicon RNA or on separate replicon RNAs of separate particles in a population), the regulatory cassettes can all be the same, the regulatory cassettes all be different and/or the regulatory cassettes can be present in any combination (e.g., two are the same and one is different).

In some embodiments, the regulatory cassette of this invention can be an alphavirus subgenomic promoter. In other embodiments, the regulatory cassette of this invention can comprise (i) an alphavirus subgenomic promoter to direct transcription, and (ii) an IRES element to direct translation.

In those embodiments of this invention wherein nucleic acid encoding CMV pp65 protein and nucleic acid encoding CMV IE1 protein are present on the same replicon, the nucleic acid can be present as a coding sequence that produces a fusion protein of pp65 and IE1. A nonlimiting example of a nucleic acid encoding a pp65/IE1 fusion protein is provided as SEQ ID NO:3 and a nonlimiting example of an amino acid sequence of a pp65/IE1 fusion protein is provided herein as SEQ ID NO:4. Other nucleic acids encoding the pp65/IE1 fusion protein of this invention would be readily determined by one of ordinary skill in the art and would vary based on the degeneracy of the DNA code. Other amino acid sequences having the functional characteristics of the pp65/IE1 fusion protein of this invention would be readily determined by one of ordinary skill in the art and would vary based on, for example conservative amino acid substitutions, as well as deletions and/or additions having a neutral or nominal effect on the functional characteristics of the fusion protein.

In those embodiments of this invention wherein the replicon RNA comprises nucleic acid encoding CMV gB protein or an immunogenic fragment thereof, the transmembrane domain of the gB protein or an immunogenic fragment thereof can be present or it can be deleted. A nonlimiting example of a nucleic acid encoding a CMV gB protein that has been truncated to delete the transmembrane domain is provided herein as SEQ ID NO:1. A nonlimiting example of an amino acid sequence of a truncated CMV gB protein is provided herein as SEQ ID NO:2. Other nucleic acids encoding the gB protein of this invention would be readily determined by one of ordinary skill in the art and would vary based on the degeneracy of the DNA code. Other amino acid sequences having the functional characteristics of the gB protein of this invention would be readily determined by one of ordinary skill in the art and would vary based on, for example conservative amino acid substitutions, as well as deletions and/or additions having a neutral or nominal effect on the functional characteristics of the gB protein.

Immunogenic fragments of the CMV proteins of this invention would be readily identified by one of ordinary skill in the art according to standard methods for identifying regions of immunogenicity in an amino acid sequence. Nonlimiting examples of immunogenic fragments of this invention are provided in the Sequence Listing included herewith and identified as SEQ ID NOs:5-262. These immunogenic fragments can be employed in any combination and in any ratio relative to one another in the compositions and methods of this invention. For example, "pools" of peptides can be created according to protocols standard in the art (see, e.g., Maecker et al. "Use of overlapping peptide mixtures as antigens for cytokine flow cytometry" *Journal of Immunological Methods* 255:27-40 (2001)) and used to evaluate the immune response in subjects infected with HCMV or immunized with HCMV vaccines to identify immunogenic fragments.

The CMV-expressing ARPs of this invention are formulated for use as pharmaceutical formulations, vaccines or immunogenic compositions, either for prophylaxis and/or treatment. These pharmaceutical formulations comprise a composition of this invention (e.g., infectious, propagation-defective ARPs) in combination with a pharmaceutically acceptable carrier.

Thus, in certain embodiments, the present invention provides a composition comprising an alphavirus particle of this invention in a pharmaceutically acceptable carrier. The compositions described herein can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of this invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation. The pharmaceutical compositions are prepared by any of the well-known techniques of pharmacy including, but not limited to, admixing the components, optionally including one or more accessory ingredients. Exemplary pharmaceutically acceptable carriers include, but are not limited to, sterile pyrogen-free water and sterile pyrogen-free physiological saline solution. Such carriers can further include protein (e.g., serum albumin) and sugar (sucrose, sorbitol, glucose, etc.)

The pharmaceutical compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration. The compositions herein may also be administered via a skin scarification method, or transdermally via a patch or liquid. The compositions may be delivered subdermally in the form of a biodegradable material that releases the compositions over a period of time. The most suitable route in any given case will depend, as is well known in the art, on such factors as the species, age, gender and overall condition of the subject, the nature and severity of the condition being treated and/or on the nature of the particular composition (i.e., dosage, formulation) that is being administered.

The ARPs can also be present in a formulation of this invention in an immunogenic amount. An "immunogenic amount" is an amount of the infectious alphavirus replicon particles which is sufficient to evoke an immune response in the subject to which the pharmaceutical formulation is administered. An amount of from about $10^4$ to about $10^{10}$, preferably $10^5$ to $10^9$, and in particular $10^6$ to $10^8$ infectious units (IU., as measured by indirect immunofluorescence assay), or ARPs, per dose can be administered to a subject, depending upon the age and species of the subject being treated.

Subjects to which effective and/or immunogenic amounts of the compositions of the present invention are administered include human and animal (e.g., mouse, monkey, guinea pig) subjects.

The vaccine compositions of this invention further comprise combinations of CMV polypeptide expressing ARPs with other CMV polypeptide expressing systems to provide the broadest (i.e., all aspects of the immune response, including those features described hereinabove) cellular and humoral responses possible. In certain embodiments, this can include the use of heterologous prime-boost strategies, in which the ARP compositions are used in combination with one or more of the following: recombinantly produced, purified CMV polypeptides (or immunogenic fragments thereof), naked nucleic acids encoding one or more CMV polypeptides, immunogenic fragments or epitopes, such nucleic acids formulated with lipid-containing moieties, non-alphavirus vectors (e.g., pox vectors, adenoviral vectors, herpes vectors, vesicular stomatitis virus vectors, paramyxoviral vectors, parvovirus vectors, papovavirus vectors, adeno-associated virus vectors and retroviral vectors) expressing one or more CMV immunogens, and other alphavirus vectors expressing one or more CMV immunogens. The viral vectors can be virus-like particles or nucleic acids. The alphavirus vectors can be replicon-containing particles, DNA-based replicon-containing vectors (sometimes referred to as an "ELVIS" system, see, for example, U.S. Pat. No. 5,814,482) and/or naked RNA vectors.

Thus, the present invention further provides a method of inducing an immune response to CMV in a subject, comprising administering to the subject an effective amount of the populations, particles and/or compositions of this invention. Also provided herein is a method of preventing or treating a CMV infection in a subject, comprising administering to the subject an effective amount of a population, particle and/or composition of this invention.

As used herein, an "effective amount" refers to an amount of a compound or composition that is sufficient to produce a desired effect, which can be a therapeutic, prophylactic and/or beneficial effect.

Also as used herein, the terms "treat," "treating" and "treatment" include any type of mechanism, action or activity that results in a change in the medical status of a subject, including an improvement in the condition of the subject (e.g., change or improvement in one or more symptoms and/or clinical parameters), delay in the progression of the condition, prevention or delay of the onset of a disease or illness, etc.

In some embodiments, the present invention provides a method for inducing an immune response to CMV in a subject, comprising: a) priming the subject's immune system by administering to the subject an effective amount of a first immunizing component, which can be, but is not limited to, alphavirus replicon particles encoding CMV immunogens, CMV immunogens, nucleic acid molecules encoding CMV immunogens, a non-alphavirus viral vector encoding CMV immunogens, and any combination thereof, and b) boosting the subject's priming response by administering to the subject an effective amount of a second immunizing component, which can be, but is not limited to, alphavirus replicon particles encoding CMV immunogens, CMV immunogens, nucleic acid molecules encoding CMV immunogens, a non-alphavirus viral vector encoding CMV immunogens, and any combination thereof, wherein the first immunizing component can be different from the second immunizing component and wherein at least the first immunizing component or the second immunizing component is an alphavirus replicon particle encoding CMV immunogens.

In the methods of this invention, the first immunizing component can be a first alphavirus replicon particle and the second immunizing component can be a second alphavirus replicon particle, with the proviso that the first and second alphavirus particles are derived from different alphaviruses.

In other embodiments of the methods of this invention, the first immunizing component can comprise-alphavirus replicon particles encoding cytomegalovirus pp65, IE1 and gB proteins or immunogenic fragments thereof, and the second immunizing component can comprise one or more CMV proteins and/or immunogenic fragments thereof.

In the methods of this invention, the immunizing components can be administered once or more than once (i.e., multiple times). For example, a first immunizing component of this invention and/or a second immunizing component of this invention can be administered one, two, three, four, five, six, seven, eight, nine or ten times at any time interval (e.g., hours, days, weeks, months, years, etc.) and in any of the amounts described herein, which can be the same amount each time or different amounts at different times of administration in any combination. In other embodiments, the administration of the first and second immunizing components can be combined or arranged in any order (e.g., the first and second immunizing components can be administered in an alternating sequence or in any other order).

In some embodiments of the present invention, the first and/or second immunizing component can be administered with an adjuvant. As used herein, "adjuvant" describes a substance, which can be any immunomodulating substance capable of being combined with the polypeptide or nucleic acid vaccine to enhance, improve or otherwise modulate an immune response in a subject without deleterious effect on the subject.

An adjuvant of this invention can be, but is not limited to, for example, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include oil-in-water, saponin, an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153 (the entire contents of which are incorporated herein by reference), or a less reactogenic composition where the QS21 is quenched with cholesterol as disclosed in PCT publication number WO 96/33739 (the entire contents of which are incorporated herein by reference). A particularly potent adjuvant formulation involving QS21 3D-MPL & tocopherol in an oil in water emulsion is described in PCT publication number WO 95/17210 (the entire contents of which are incorporated herein by reference). In addition, the nucleic acid of this invention can include a nucleotide sequence that provides an immunostimulatory signal and/or an adjuvant function, such as CpG sequences. Such CpG sequences, or motifs, are well known in the art.

An adjuvant of this invention, such as, for example, an immunostimulatory cytokine, can be administered before, concurrent with, and/or within a few hours, several hours, and/or 1, 2, 3, 4, 5, 6, 7, 8, 9, and/or 10 days before or after the administration of a composition of this invention to a subject.

Furthermore, any combination of adjuvants, such as immunostimulatory cytokines, can be co-administered to the subject before, after or concurrent with the administration of a composition of this invention. For example, combinations of immunostimulatory cytokines, can consist of two or more immunostimulatory cytokines of this invention, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response directed produced in response to administration of a composition of this invention to a subject with and without the adjuvant or combination of adjuvants, using standard procedures, as described herein and as known in the art.

In various embodiments of this invention comprising a non-alphavirus viral vector, the non-alphavirus viral vector can be, but is not limited to, a retroviral vector, an adenoviral vector, a poxvirus vector, a Vesicular Stomatitis Virus (VSV) vector or a picornavirus vector, as well as any other non-alphavirus viral vector now known or later identified.

The alphavirus particles employed in the methods of this invention can be particles derived from any alphavirus, such as, for example, Venezuelan Equine Encephalitis virus, S.A.AR86 virus, Semliki Forest virus, Sindbis virus, Ross River virus and any combination thereof. The alphavirus particles of this invention can also comprise elements (e.g., structural proteins/replicon RNA) from two or more different alphaviruses to produce chimeric alphavirus particles (e.g., a particle comprising a Sindbis virus replicon RNA and VEE structural proteins). The production and testing of such chimeric particles is known in the art.

EXAMPLES

Example 1

Cloning of CMV Genes into VEE Replicon (FIG. 1)

Standard molecular biology techniques were used in the cloning of all constructs and their analysis. The VEE replicon vector (Rayner et al.) was modified to introduce additional restriction sites for run-off transcription and ease of cloning. CMV genes coding for pp65 (UL83, strain AD169 (American Type Culture Collection No. VR-538), Immediate Early gene 1 (IE1, UL123, strain AD169), full-length glycoprotein B (gB, UL55, strain Towne (American Type Culture Collection No. VR-977) or C-terminus truncated gB (amino acids 1-692, excludes predicted transmembrane domain) were cloned under the control of a subgenomic ("SG") 26S promoter to generate replicons with single or multiple CMV genes. In addition, a pp65-IE1 fusion construct was made, which was cloned into this modified VEE vector in a similar fashion. Table 1 identifies the various constructs that were made and tested. In some embodiments, a Csp45 1 restriction site was introduced into the replicon to linearize the vector, as a NotI site was identified in the pp65 coding sequence and NotI was used to linearize this vector for other uses, based on a NotI restriction site in the replicon sequence. In other embodiments, the pp65 coding sequence is modified to remove the NotI restriction site.

Example 2

Production of VEE Replicon Particles Expressing CMV Genes

Packaged VEE Replicon Particles (VRP) were obtained after electroporation of CHO or Vero cells with in vitro-transcribed replicon and helper RNAs. Cells were maintained in EMEM (Vero) or F12-K (CHO) supplemented with 10% FBS in an atmosphere of 5% $CO_2$ at 37° C. For electroporation, cells were trypsinized and washed with phosphate buffered saline (PBS). Electroporation was performed using GenePulser Electroporator (Bio-Rad; Hercules, Calif.) and 0.4 cm cuvettes. After electroporation, the cells were resuspended in growth medium, seeded into tissue culture flasks containing growth medium, and incubated over night. Growth medium containing released VRP was collected, filtered, and tested to confirm the absence of replication competent virus. VRP were then purified by affinity chromatography on HiTrap® heparin HP columns (Amersham, Piscataway, NJ), which are highly cross-linked agarose (6%), activated with N-hydroxysuccinimide and containing porcine heparin as the ligand. The VRP were formulated with 1% Human Serum Albumin and 5% sucrose in phosphate buffered saline.

Example 3

Protein Expression from CMV-Expressing VRPs

Expression of nucleic acids to produce CMV proteins was analyzed by SDS-PAGE followed by silver stain (Invitrogen Inc., Carlsbad, Calif.) or western blot analysis with gene-specific monoclonal (Rumbaugh-Goodwin Institute) or goat polyclonal antibodies. Goat polyclonal antibodies were generated by immunization with purified CMV proteins.

Cells were infected with specified VRP at a multiplicity of infection (moi) of 10 IU/cell and incubated for 18-22 hr. Cell lysates in 0.5% SDS, 0.5% NP-40, 50 mM Tris-HCl, pH 7.5, 0.1 M NaCl, 1 mM EDTA were normalized by protein content and 1 µg per lane of total protein was resolved on 4-12% gradient SDS-PAGE (Invitrogen Inc., Carlsbad, Calif.). Proteins were visualized by silver staining as recommended by manufacturer (Invitrogen Inc., Carlsbad, Calif.). Silver staining revealed prominent bands of the molecular weight expected for the CMV gene products.

Cells lysates prepared as described were analyzed by western blot with monoclonal or goat polyclonal monospecific antibodies specific for gB protein in reducing or non-reducing conditions. Western blot analysis revealed prominent bands of the molecular weight expected for the CMV gene products.

Example 4

Immunogenicity of VEE Replicon Particles Expressing CMV Genes

Groups of 6-week-old female BALB/c mice (Charles River Laboratories, Raleigh, N.C.) were injected subcutaneously in both rear footpads with a total of $10^6$ IU of VRP at weeks 0, 3, and 8. Serum samples were collected by retro-orbital bleed at day-1 (pre-bleed) and weeks 4 and 9. Spleens were harvested at week 15.

Some groups of 12 female BALB/c mice were primed and boosted with gB-VRP or truncated gB-VRP on Days 1 and 22. For the third inoculation given on Day 51, animals in these groups were split in half. Six of the animals in each group (Groups 3A and 4A) received a third VRP inoculation (the same VRP they received for the prime and boost) and the remaining six animals (Groups 3B and 4B) received truncated gB protein adjuvanted with RIBI adjuvant (Corixa Corporation, Seattle, Wash.) and bacterial endotoxin prepared in saline as their third inoculation. The VRPs were given at an inoculation dose of $1\times10^6$ IU in the subcutaneous rear footpads. For the gB protein inoculations, 50 µg of protein in adjuvant was administered by intraperitoneal injection.

A. Induction of Humoral Immunity

A CMV neutralization assay was used to evaluate the humoral immune response to CMV gB. CMV neutralization titer was determined by incubating serial dilutions of heat-inactivated sera with a known concentration of CMV (Towne strain) in the presence of 5% guinea pig complement (Cedar-Lane Laboratories, Homby, Ontario, Canada). Reduction of CMV infection was determined using a viral neutralization assay, as is standardly known in the art. Neutralization titer ($NT_{50}$) was defined as 50% reduction in $OD_{570}$ compared to CMV-only control.

Figure 2:
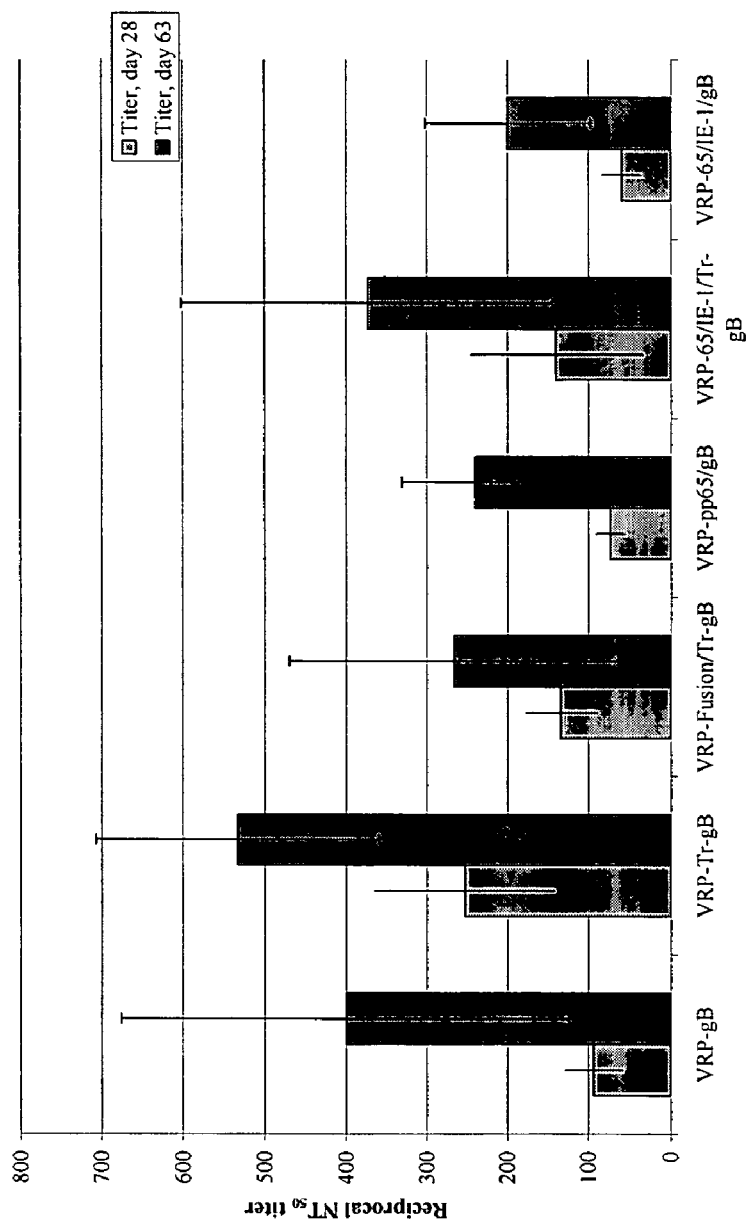
FIG. 2 shows the results of a CMV neutralization assay following immunization of mice with various CMV-VRP vaccines.

Immunization of mice with VRP expressing nucleic acid encoding glycoprotein B (full-length or truncated) resulted in induction of virus-neutralizing antibodies (FIG. 2). Neutralizing antibody titers were significantly increased after the second boost. Higher neutralizing antibody titers were seen in Groups 3B and 4B with the addition of protein and adjuvant compared to the groups (Groups 3A and 4A) that got a third dose of VRP instead of protein and adjuvant (See FIG. 2, Day 63).

B. Induction of Cellular Immunity

An IFN-γ ELISPOT assay was used to evaluate the cellular immune response to pp65 and IE1. Splenic lymphocytes were prepared using Lympholyte M density gradient centrifugation after lysis of red blood cells. 96-well ELISPOT IP plates (Millipore, Bedford, Mass.) were coated with 1 µg anti-mouse IFN-γ mAb/well (MabTech, Mariemont, Ohio) and blocked with 10% FCS in RPMI-1640 (including supplements). $10^6$ lymphocytes/well were plated alone or after mixing with Con A (4 µg/ml) or peptide (10 µg/ml). In all cases, each peptide was tested against known positive and negative lymphocytes and each lymphocyte preparation was tested against known positive and negative peptides. For detection, 0.1 µg of biotinylated anti-mouse IFN-γ (MabTech) was added to each well, followed by incubation with Avidin-Peroxidase Complex (Vector Laboratories, Burlingame, Calif.), and color development with AEC substrate. Spots were quantified by Zellnet, Inc. (New York, N.Y.) using a Zeiss ELISPOT reader.

Cellular immune response of mice to CMV-expressing VRPs was measured by ELISPOT assay as described above. All constructs induced a robust immune response to pp65 and IE1 proteins (FIG. 3).

Example 5

Vaccine "Challenge" in Solid Organ Transplant Recipients

A vaccine of the invention can be tested in "challenge" studies in humans undergoing solid organ transplant surgeries. CMV-seronegative patients on the organ/marrow waiting list are immunized, and then they undergo transplant surgery two weeks to several years after immunization. The "challenge" comes from the transplant itself, since most transplanted organs in the United States (>60%) come from seropositive donors, and the CMV virus is transmitted via the organ. In addition, these CMV seronegative recipients of CMV seropositive organs are given booster doses of vaccine after the transplant surgery to maintain a sufficient level of immunity to prevent CMV disease. Booster doses are initially given at intervals of every one month to every six months. Patients are monitored and evaluated for at least one year, at monthly or quarterly intervals, and/or after the treatment for signs or symptoms of CMV disease.

Example 6

Vaccination of Bone Marrow Transplant Recipients

A vaccine of this invention can be administered to bone marrow transplant recipients to reduce or eliminate the transmission of HCMV via the donor bone marrow. The risk of disease from such HCMV transmission is particularly high in those seronegative recipients who receive a seropositive bone marrow. In one vaccination protocol, the bone marrow donor is vaccinated with a vaccine of the invention on one or more than one occasion, e.g., at six and two weeks before making the donation; the BMT recipient is vaccinated at intervals (e.g., every one to six months) starting about four weeks to about six months after receiving the transplanted bone marrow. The appearance of CMV viremia is monitored in the transplant recipient.

Example 7

Vaccine "Challenge" in Pregnant Women

A vaccine of the invention can be further tested in women of child-bearing potential who test seronegative for HCMV. Immunization protocols will typically include a priming immunization followed by one or two "booster" immunizations. These women are monitored for pregnancy outcomes, including the rates of CMV infection, symptomatic disease, and delayed sequelae in newborns.

Although the present process has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents and publications in their entireties are hereby incorporated by reference into this application in order to more fully describe the state of the art to which this invention pertains.

TABLE 1

Organization of CMV genes in CMV-VRP vaccine candidates.

| # | Designation | SG promoter #1 | SG promoter #2 | SG promoter #3 |
|---|---|---|---|---|
| 1 | VRP-pp65 | pp65 | | |
| 2 | VRP-IE1 | IE1 | | |
| 3 | VRP-gB | gB | | |
| 4 | VRP-Tr-gB | Tr-gB | | |
| 5 | VRP-pp65/IE1 | pp65 | IE1 | |
| 9 | VRP-pp65/gB | pp65 | gB | |
| 6 | VRP-IE1/pp65 | IE1 | pp65 | |
| 11 | VRP-pp65/IE1/gB | pp65 | IE1 | gB |
| 10 | VRP-pp65/IE1/Tr-gB | pp65 | IE1 | Tr-gB |
| 7 | VRP-pp65-IE1 fusion | pp65-IE1 fusion | | |
| 8 | VRP-pp65-IE1 fusion/Tr-gB | pp65-IE1 fusion | Tr-gB | |

What is claimed is:

1. A population of alphavirus replicon particles wherein said particles comprise alphavirus replicon RNAs, wherein a first replicon RNA comprises nucleic acid encoding a fusion protein of cytomegalovirus pp65 and IE1 proteins or epitopes thereof, and a second replicon RNA comprises nucleic acid encoding cytomegalovirus gB protein or an epitope thereof, and wherein each of the first and second replicon RNAs is contained within a separate alphavirus replicon particle.

2. A population of alphavirus replicon particles wherein said particles comprise a replicon RNA which comprises a regulatory cassette that directs transcription and translation of a nucleic acid encoding a fusion protein of cytomegalovirus pp65 and IE1 proteins, or epitopes thereof.

3. The population of claim 2, wherein the regulatory cassette is an alphavirus subgenomic promoter.

4. The population of claim 1 wherein the nucleic acid encoding cytomegalovirus gB protein or an epitope thereof encodes a CMV gB protein or epitope thereof wherein the transmembrane domain has been deleted.

5. A composition comprising the population of claim 1 in a pharmaceutically acceptable carrier.

6. A method of inducing an immune response to CMV in a subject, comprising administering to the subject an effective amount of the population of claim 1.

7. The method of claim 6, wherein the population is administered multiple times.

8. A method for inducing an immune response to CMV in a human subject, comprising:
   a) priming the subject's immune system by administering to the subject an effective amount of a first immunizing component selected from the group consisting of:
      a population of alphavirus replicon particles encoding CMV immunogens,
      CMV immunogens,
      nucleic acid molecules encoding CMV immunogens,
      a non-alphavirus viral vector encoding CMV immunogens, and
      any combination thereof; and
   b) boosting the subject's priming response by administering to the subject an effective amount of a second immunizing component selected from the group consisting of:
      a population of alphavirus replicon particles encoding CMV immunogens,
      CMV immunogens,
      nucleic acid molecules encoding CMV immunogens,
      a non-alphavirus viral vector encoding CMV immunogens, and
      any combination thereof,
   wherein the first immunizing component is different from the second immunizing component and wherein the first immunizing component is the population of claim 1.

9. The method of claim 8, wherein the second immunizing component is a population of alphavirus replicon particles, with the proviso that the alphavirus replicon particles of the first immunizing component and the alphavirus particles of the second immunizing component are derived from different alphaviruses.

10. The method of claim 8, further comprising administering the first and/or second immunizing component multiple times.

11. The method of claim 8, wherein the second immunizing component comprises CMV immunogens comprising one or more CMV proteins and/or epitopes thereof.

12. The method of claim 8, wherein the CMV gB protein of the first immunizing component is a truncated gB protein.

13. The method of claim 8, wherein the first and/or second immunizing component is administered with an adjuvant.

14. The method of claim 13, wherein the adjuvant is selected from the group consisting of aluminum salts, oil-in-water, saponin, cytokines, oligonucleotides encoding immunostimulatory signals and any combination thereof.

15. The method of claim 8, wherein the second immunizing component is a non-alphavirus viral vector selected from the group consisting of a retroviral vector, an adenoviral vector, a poxvirus vector, a Vesicular Stomatitis Virus (VSV) vector and a picornavirus vector.

16. The method of claim 8, wherein the second immunizing component comprises an alphavirus replicon particle selected from the group consisting of a particle derived from Venezuelan Equine Encephalitis virus, S.A.AR86 virus, Semliki Forest virus, Sindbis virus, Ross River virus and any combination thereof.

17. The method of claim 16, wherein the alphavirus replicon particle comprises elements from two or more alphaviruses.

18. A composition comprising the population of claim 2 in a pharmaceutically acceptable carrier.

19. A method of inducing an immune response to CMV in a subject, comprising administering to the subject an effective amount of the population of claim 2.

20. The method of claim 19, wherein the population is administered multiple times.

21. A method for inducing an immune response to CMV in a human subject, comprising:
a) priming the subject's immune system by administering to the subject an effective amount of a first immunizing component selected from the group consisting of:
a population of alphavirus replicon particles encoding CMV immunogens,
CMV immunogens,
nucleic acid molecules encoding CMV immunogens,
a non-alphavirus viral vector encoding CMV immunogens, and
any combination thereof; and
b) boosting the subject's priming response by administering to the subject an effective amount of a second immunizing component selected from the group consisting of:
a population of alphavirus replicon particles encoding CMV immunogens,
CMV immunogens,
nucleic acid molecules encoding CMV immunogens,
a non-alphavirus viral vector encoding CMV immunogens, and
any combination thereof,
wherein the first immunizing component is different from the second immunizing component and wherein the second immunizing component is the population of claim 1.

22. The method of claim 21, wherein the first immunizing component is a population of alphavirus replicon particles, with the proviso that the alphavirus replicon particles of the first immunizing component and the alphavirus particles of the second immunizing component are derived from different alphaviruses.

23. The method of claim 21, further comprising administering the first and/or second immunizing component multiple times.

24. The method of claim 21, wherein the first immunizing component comprises CMV immunogens comprising one or more CMV proteins and/or epitopes thereof.

25. The method of claim 21, wherein the CMV gB protein of the second immunizing component is a truncated gB protein.

26. The method of claim 21, wherein the first and/or second immunizing component is administered with an adjuvant.

27. The method of claim 26, wherein the adjuvant is selected from the group consisting of aluminum salts, oil-in-water, saponin, cytokines, oligonucleotides encoding immunostimulatory signals and any combination thereof.

28. The method of claim 21, wherein the first immunizing component is a non-alphavirus viral vector selected from the group consisting of a retroviral vector, an adenoviral vector, a poxvirus vector, a Vesicular Stomatitis Virus (VSV) vector and a picornavirus vector.

29. The method of claim 21, wherein the first immunizing component comprises an alphavirus replicon particle selected from the group consisting of a particle derived from Venezuelan Equine Encephalitis virus, S.A.AR86 virus, Semliki Forest virus, Sindbis virus, Ross River virus and any combination thereof.

30. The method of claim 29, wherein the alphavirus replicon particle comprises elements from two or more alphaviruses.

31. A method for inducing an immune response to CMV in a human subject, comprising:
a) priming the subject's immune system by administering to the subject an effective amount of a first immunizing component selected from the group consisting of:
a population of alphavirus replicon particles encoding CMV immunogens,
CMV immunogens,
nucleic acid molecules encoding CMV immunogens,
a non-alphavirus viral vector encoding CMV immunogens, and
any combination thereof; and
b) boosting the subject's priming response by administering to the subject an effective amount of a second immunizing component selected from the group consisting of:
a population of alphavirus replicon particles encoding CMV immunogens,
CMV immunogens,
nucleic acid molecules encoding CMV immunogens,
a non-alphavirus viral vector encoding CMV immunogens, and
any combination thereof,
wherein the first immunizing component is different from the second immunizing component and wherein the first immunizing component is the population of claim 2.

32. The method of claim 31, wherein the second immunizing component is a population of alphavirus replicon particles, with the proviso that the alphavirus replicon particles of the first immunizing component and the alphavirus particles of the second immunizing component are derived from different alphaviruses.

33. The method of claim 31, further comprising administering the first and/or second immunizing component multiple times.

34. The method of claim 31, wherein the second immunizing component comprises CMV immunogens comprising one or more CMV proteins and/or epitopes thereof.

35. The method of claim 31, wherein the CMV gB protein of the first immunizing component is a truncated gB protein.

36. The method of claim 31, wherein the first and/or second immunizing component is administered with an adjuvant.

37. The method of claim 36, wherein the adjuvant is selected from the group consisting of aluminum salts, oil-in-water, saponin, cytokines, oligonucleotides encoding immunostimulatory signals and any combination thereof.

38. The method of claim 31, wherein the second immunizing component is a non-alphavirus viral vector selected from the group consisting of a retroviral vector, an adenoviral vector, a poxvirus vector, a Vesicular Stomatitis Virus (VSV) vector and a picornavirus vector.

39. The method of claim 31, wherein the second immunizing component comprises an alphavirus replicon particle selected from the group consisting of a particle derived from Venezuelan Equine Encephalitis virus, S.A.AR86 virus, Semliki Forest virus, Sindbis virus, Ross River virus and any combination thereof.

40. The method of claim 39, wherein the alphavirus replicon particle comprises elements from two or more alphaviruses.

41. A method for inducing an immune response to CMV in a human subject, comprising:
  a) priming the subject's immune system by administering to the subject an effective amount of a first immunizing component selected from the group consisting of:
    a population of alphavirus replicon particles encoding CMV immunogens,
    CMV immunogens,
    nucleic acid molecules encoding CMV immunogens,
    a non-alphavirus viral vector encoding CMV immunogens, and
    any combination thereof; and
  b) boosting the subject's priming response by administering to the subject an effective amount of a second immunizing component selected from the group consisting of:
    a population of alphavirus replicon particles encoding CMV immunogens,
    CMV immunogens,
    nucleic acid molecules encoding CMV immunogens,
    a non-alphavirus viral vector encoding CMV immunogens, and
    any combination thereof,
  wherein the first immunizing component is different from the second immunizing component and wherein the second immunizing component is the population of claim 2.

42. The method of claim 41, wherein the first immunizing component is a population of alphavirus replicon particles, with the proviso that the alphavirus replicon particles of the first immunizing component and the alphavirus particles of the second immunizing component are derived from different alphaviruses.

43. The method of claim 41, further comprising administering the first and/or second immunizing component multiple times.

44. The method of claim 41, wherein the first immunizing component comprises CMV immunogens comprising one or more CMV proteins and/or epitopes thereof.

45. The method of claim 41, wherein the CMV gB protein of the second immunizing component is a truncated gB protein.

46. The method of claim 41, wherein the first and/or second immunizing component is administered with an adjuvant.

47. The method of claim 46, wherein the adjuvant is selected from the group consisting of aluminum salts, oil-in-water, saponin, cytokines, oligonucleotides encoding immunostimulatory signals and any combination thereof.

48. The method of claim 41, wherein the first immunizing component is a non-alphavirus viral vector selected from the group consisting of a retroviral vector, an adenoviral vector, a poxvirus vector, a Vesicular Stomatitis Virus (VSV) vector and a picornavirus vector.

49. The method of claim 41, wherein the first immunizing component comprises an alphavirus replicon particle selected from the group consisting of a particle derived from Venezuelan Equine Encephalitis virus, S.A.AR86 virus, Semliki Forest virus, Sindbis virus, Ross River virus and any combination thereof.

50. The method of claim 49, wherein the alphavirus replicon particle comprises elements from two or more alphaviruses.

* * * * *

UNITED STATES PATENT AND TRADEMARK OFFICE
CERTIFICATE OF CORRECTION

PATENT NO. : 7,419,674 B2  Page 1 of 1
APPLICATION NO. : 10/886773
DATED : September 2, 2009
INVENTOR(S) : Chulay et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 20 days Delete the phrase "by 20 days" and insert -- by 72 days --

Signed and Sealed this

First Day of June, 2010

David J. Kappos
*Director of the United States Patent and Trademark Office*

SEQUENCE LISTING

<160> NUMBER OF SEQ ID NOS: 262

<210> SEQ ID NO 1
<211> LENGTH: 2079
<212> TYPE: DNA
<213> ORGANISM: Human cytomegalovirus
<220> FEATURE:
<221> NAME/KEY: CDS
<222> LOCATION: (1)..(2076)
<223> OTHER INFORMATION: Truncated gB

<400> SEQUENCE: 1

```
atg gaa tcc agg atc tgg tgc ctg gta gtc tgc gtt aac ttg tgt atc      48
Met Glu Ser Arg Ile Trp Cys Leu Val Val Cys Val Asn Leu Cys Ile
1               5                   10                  15 gtc tgt ctg ggt gct gcg gtt tcc tca tct tct act cgt gga act tct      96
Val Cys Leu Gly Ala Ala Val Ser Ser Ser Ser Thr Arg Gly Thr Ser
            20                  25                  30 gct act cac agt cac cat tcc tct cat acg acg tct gct gct cat tct     144
Ala Thr His Ser His His Ser Ser His Thr Thr Ser Ala Ala His Ser
        35                  40                  45 cga tcc ggt tca gtc tct caa cgc gta act tct tcc caa acg gtc agc     192
Arg Ser Gly Ser Val Ser Gln Arg Val Thr Ser Ser Gln Thr Val Ser
    50                  55                  60 cat ggt gtt aac gag acc atc tac aac act acc ctc aag tac gga gat     240
His Gly Val Asn Glu Thr Ile Tyr Asn Thr Thr Leu Lys Tyr Gly Asp
65                  70                  75                  80 gtg gtg ggg gtc aac acc acc aag tac ccc tat cgc gtg tgt tct atg     288
Val Val Gly Val Asn Thr Thr Lys Tyr Pro Tyr Arg Val Cys Ser Met
                85                  90                  95 gca cag ggt acg gat ctt att cgc ttt gaa cgt aat atc gtc tgc acc     336
Ala Gln Gly Thr Asp Leu Ile Arg Phe Glu Arg Asn Ile Val Cys Thr
            100                 105                 110 tcg atg aag ccc atc aat gaa gac ctg gac gag ggc atc atg gtg gtc     384
Ser Met Lys Pro Ile Asn Glu Asp Leu Asp Glu Gly Ile Met Val Val
        115                 120                 125 tac aaa cgc aac atc gtc gcg cac acc ttt aag gta cga gtc tac cag     432
Tyr Lys Arg Asn Ile Val Ala His Thr Phe Lys Val Arg Val Tyr Gln
    130                 135                 140 aag gtt ttg acg ttt cgt cgt agc tac gct tac gtc cac acc act tat     480
Lys Val Leu Thr Phe Arg Arg Ser Tyr Ala Tyr Val His Thr Thr Tyr
145                 150                 155                 160
```

```
ctg ctg ggc agc aac acg gaa tac gtg gcg cct cct atg tgg gag att      528
Leu Leu Gly Ser Asn Thr Glu Tyr Val Ala Pro Pro Met Trp Glu Ile
            165                 170                 175 cat cat atc aac agt cac agt cag tgc tac agt tcc tac agc cgc gtt      576
His His Ile Asn Ser His Ser Gln Cys Tyr Ser Ser Tyr Ser Arg Val
            180                 185                 190 ata gca ggc acg gtt ttc gtg gct tat cat agg gac agc tat gaa aac      624
Ile Ala Gly Thr Val Phe Val Ala Tyr His Arg Asp Ser Tyr Glu Asn
            195                 200                 205 aaa acc atg caa tta atg ccc gac gat tat tcc aac acc cac agt acc      672
Lys Thr Met Gln Leu Met Pro Asp Asp Tyr Ser Asn Thr His Ser Thr
    210                 215                 220 cgt tac gtg acg gtc aag gat caa tgg cac agc cgc ggc agc acc tgg      720
Arg Tyr Val Thr Val Lys Asp Gln Trp His Ser Arg Gly Ser Thr Trp
225                 230                 235                 240 ctc tat cgt gag acc tgt aat ctg aat tgt atg gtg acc atc act act      768
Leu Tyr Arg Glu Thr Cys Asn Leu Asn Cys Met Val Thr Ile Thr Thr
                245                 250                 255 gcg cgc tcc aag tat ccc tat cat ttt ttc gca act tcc acg ggt gat      816
Ala Arg Ser Lys Tyr Pro Tyr His Phe Phe Ala Thr Ser Thr Gly Asp
            260                 265                 270 gtg gtt gac att tct cct ttc tac aac gga act aat cgc aat gcc agc      864
Val Val Asp Ile Ser Pro Phe Tyr Asn Gly Thr Asn Arg Asn Ala Ser
    275                 280                 285 tat ttt gga gaa aac gcc gac aag ttt ttc att ttt ccg aac tac act      912
Tyr Phe Gly Glu Asn Ala Asp Lys Phe Phe Ile Phe Pro Asn Tyr Thr
290                 295                 300 atc gtc tcc gac ttt gga aga ccg aat tct gcg tta gag acc cac agg      960
Ile Val Ser Asp Phe Gly Arg Pro Asn Ser Ala Leu Glu Thr His Arg
305                 310                 315                 320 ttg gtg gct ttt ctt gaa cgt gcg gac tca gtg atc tcc tgg gat ata     1008
Leu Val Ala Phe Leu Glu Arg Ala Asp Ser Val Ile Ser Trp Asp Ile
                325                 330                 335 cag gac gag aag aat gtt act tgt caa ctc act ttc tgg gaa gcc tcg     1056
Gln Asp Glu Lys Asn Val Thr Cys Gln Leu Thr Phe Trp Glu Ala Ser
            340                 345                 350 gaa cgc acc att cgt tcc gaa gcc gag gac tcg tat cac ttt tct tct     1104
Glu Arg Thr Ile Arg Ser Glu Ala Glu Asp Ser Tyr His Phe Ser Ser
    355                 360                 365 gcc aaa atg acc gcc act ttc tta tct aag aag caa gag gtg aac atg     1152
Ala Lys Met Thr Ala Thr Phe Leu Ser Lys Lys Gln Glu Val Asn Met
370                 375                 380 tcc gac tct gcg ctg gac tgt gta cgt gat gag gcc ata aat aag tta     1200
Ser Asp Ser Ala Leu Asp Cys Val Arg Asp Glu Ala Ile Asn Lys Leu
385                 390                 395                 400 cag cag att ttc aat act tca tac aat caa aca tat gaa aaa tat gga     1248
Gln Gln Ile Phe Asn Thr Ser Tyr Asn Gln Thr Tyr Glu Lys Tyr Gly
                405                 410                 415 aac gtg tcc gtc ttt gaa acc act ggt ggt ttg gtg gtg ttc tgg caa     1296
Asn Val Ser Val Phe Glu Thr Thr Gly Gly Leu Val Val Phe Trp Gln
            420                 425                 430 ggt atc aag caa aaa tct ctg gtg gaa ctc gaa cgt ttg gcc aac cgc     1344
Gly Ile Lys Gln Lys Ser Leu Val Glu Leu Glu Arg Leu Ala Asn Arg
    435                 440                 445 tcc agt ctg aat ctt act cat aat aga acc aaa aga agt aca gat ggc     1392
Ser Ser Leu Asn Leu Thr His Asn Arg Thr Lys Arg Ser Thr Asp Gly
450                 455                 460 aac aat gca act cat tta tcc aac atg gag tcg gtg cac aat ctg gtc     1440
Asn Asn Ala Thr His Leu Ser Asn Met Glu Ser Val His Asn Leu Val
465                 470                 475                 480
```

```
tac gcc cag ctg cag ttc acc tat gac acg ttg cgc ggt tac atc aac    1488
Tyr Ala Gln Leu Gln Phe Thr Tyr Asp Thr Leu Arg Gly Tyr Ile Asn
                485                 490                 495 cgg gcg ctg gcg caa atc gca gaa gcc tgg tgt gtg gat caa cgg cgc    1536
Arg Ala Leu Ala Gln Ile Ala Glu Ala Trp Cys Val Asp Gln Arg Arg
            500                 505                 510 acc cta gag gtc ttc aag gaa ctt agc aag atc aac ccg tca gct att    1584
Thr Leu Glu Val Phe Lys Glu Leu Ser Lys Ile Asn Pro Ser Ala Ile
        515                 520                 525 ctc tcg gcc atc tac aac aaa ccg att gcc gcg cgt ttc atg ggc gat    1632
Leu Ser Ala Ile Tyr Asn Lys Pro Ile Ala Ala Arg Phe Met Gly Asp
    530                 535                 540 gtc ctg ggt ctg gcc agc tgc gtg acc att aac caa acc agc gtc aag    1680
Val Leu Gly Leu Ala Ser Cys Val Thr Ile Asn Gln Thr Ser Val Lys
545                 550                 555                 560 gtg ctg cgt gat atg aat gtg aag gaa tcg cca gga cgc tgc tac tca    1728
Val Leu Arg Asp Met Asn Val Lys Glu Ser Pro Gly Arg Cys Tyr Ser
                565                 570                 575 cga cca gtg gtc atc ttt aat ttc gcc aac agc tcg tac gtg cag tac    1776
Arg Pro Val Val Ile Phe Asn Phe Ala Asn Ser Ser Tyr Val Gln Tyr
            580                 585                 590 ggt caa ctg ggc gag gat aac gaa atc ctg ttg ggc aac cac cgc act    1824
Gly Gln Leu Gly Glu Asp Asn Glu Ile Leu Leu Gly Asn His Arg Thr
        595                 600                 605 gag gaa tgt cag ctt ccc agc ctc aag atc ttc atc gcc ggc aac tcg    1872
Glu Glu Cys Gln Leu Pro Ser Leu Lys Ile Phe Ile Ala Gly Asn Ser
    610                 615                 620 gcc tac gag tac gtg gac tac ctc ttc aaa cgc atg att gac ctc agc    1920
Ala Tyr Glu Tyr Val Asp Tyr Leu Phe Lys Arg Met Ile Asp Leu Ser
625                 630                 635                 640 agc atc tcc acc gtc gac agc atg atc gcc cta gac atc gac ccg ctg    1968
Ser Ile Ser Thr Val Asp Ser Met Ile Ala Leu Asp Ile Asp Pro Leu
                645                 650                 655 gaa aac acc gac ttc agg gta ctg gaa ctt tac tcg cag aaa gaa ttg    2016
Glu Asn Thr Asp Phe Arg Val Leu Glu Leu Tyr Ser Gln Lys Glu Leu
            660                 665                 670 cgt tcc agc aac gtt ttt gat ctc gag gag atc atg cgc gag ttc aat    2064
Arg Ser Ser Asn Val Phe Asp Leu Glu Glu Ile Met Arg Glu Phe Asn
        675                 680                 685 tcg tat aag cag tga                                                 2079
Ser Tyr Lys Gln
    690

<210> SEQ ID NO 2
<211> LENGTH: 692
<212> TYPE: PRT
<213> ORGANISM: Human cytomegalovirus

<400> SEQUENCE: 2

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80
```

```
Val Val Gly Val Asn Thr Thr Lys Tyr Pro Tyr Arg Val Cys Ser Met
             85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
        130                 135                 140

Lys Val Leu Thr Phe Arg Arg Ser Tyr Ala Tyr Val His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
            195                 200                 205

Lys Thr Met Gln Leu Met Pro Asp Asp Tyr Ser Asn Thr His Ser Thr
        210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
            275                 280                 285

Tyr Phe Gly Glu Asn Ala Asp Lys Phe Phe Ile Phe Pro Asn Tyr Thr
        290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
            355                 360                 365

Ala Lys Met Thr Ala Thr Phe Leu Ser Lys Lys Gln Glu Val Asn Met
        370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
        450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495
```

```
Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln
        690

<210> SEQ ID NO 3
<211> LENGTH: 3156
<212> TYPE: DNA
<213> ORGANISM: Artificial
<220> FEATURE:
<223> OTHER INFORMATION: hCMV pp65-IE1 fusion
<220> FEATURE:
<221> NAME/KEY: CDS
<222> LOCATION: (1)..(3153)

<400> SEQUENCE: 3 atg gag tcg cgc ggt cgc cgt tgt ccc gaa atg ata tcc gta ctg ggt        48
Met Glu Ser Arg Gly Arg Arg Cys Pro Glu Met Ile Ser Val Leu Gly
1               5                   10                  15 ccc att tcg ggg cac gtg ctg aaa gcc gtg ttt agt cgc ggc gat acg        96
Pro Ile Ser Gly His Val Leu Lys Ala Val Phe Ser Arg Gly Asp Thr
            20                  25                  30 ccg gtg ctg ccg cac gag acg cga ctc ctg cag acg ggt atc cac gta       144
Pro Val Leu Pro His Glu Thr Arg Leu Leu Gln Thr Gly Ile His Val
        35                  40                  45 cgc gtg agc cag ccc tcg ctg atc ttg gta tcg cag tac acg ccc gac       192
Arg Val Ser Gln Pro Ser Leu Ile Leu Val Ser Gln Tyr Thr Pro Asp
    50                  55                  60 tcg acg cca tgc cac cgc ggc gac aat cag ctg cag gtg cag cac acg       240
Ser Thr Pro Cys His Arg Gly Asp Asn Gln Leu Gln Val Gln His Thr
65                  70                  75                  80 tac ttt acg ggc agc gag gtg gag aac gtg tcg gtc aac gtg cac aac       288
Tyr Phe Thr Gly Ser Glu Val Glu Asn Val Ser Val Asn Val His Asn
                85                  90                  95 ccc acg ggc cga agc atc tgc ccc agc cag gag ccc atg tcg atc tat       336
Pro Thr Gly Arg Ser Ile Cys Pro Ser Gln Glu Pro Met Ser Ile Tyr
            100                 105                 110
```

```
                                                           -continued gtg tac gcg ctg ccg ctc aag atg ctg aac atc ccc agc atc aac gtg      384
Val Tyr Ala Leu Pro Leu Lys Met Leu Asn Ile Pro Ser Ile Asn Val
        115                 120                 125 cac cac tac ccg tcg gcg gcc gag cgc aaa cac cga cac ctg ccc gta      432
His His Tyr Pro Ser Ala Ala Glu Arg Lys His Arg His Leu Pro Val
        130                 135                 140 gct gac gct gtg att cac gcg tcg ggc aag cag atg tgg cag gcg cgt      480
Ala Asp Ala Val Ile His Ala Ser Gly Lys Gln Met Trp Gln Ala Arg
145                 150                 155                 160 ctc acg gtc tcg gga ctg gcc tgg acg cgt cag cag aac cag tgg aaa      528
Leu Thr Val Ser Gly Leu Ala Trp Thr Arg Gln Gln Asn Gln Trp Lys
                165                 170                 175 gag ccc gac gtc tac tac acg tca gcg ttc gtg ttt ccc acc aag gac      576
Glu Pro Asp Val Tyr Tyr Thr Ser Ala Phe Val Phe Pro Thr Lys Asp
            180                 185                 190 gtg gca ctg cgg cac gtg gtg tgc gcg cac gag ctg gtt tgc tcc atg      624
Val Ala Leu Arg His Val Val Cys Ala His Glu Leu Val Cys Ser Met
        195                 200                 205 gag aac acg cgc gca acc aag atg cag gtg ata ggt gac cag tac gtc      672
Glu Asn Thr Arg Ala Thr Lys Met Gln Val Ile Gly Asp Gln Tyr Val
210                 215                 220 aag gtg tac ctg gag tcc ttc tgc gag gac gtg ccc tcc ggc aag ctc      720
Lys Val Tyr Leu Glu Ser Phe Cys Glu Asp Val Pro Ser Gly Lys Leu
225                 230                 235                 240 ttt atg cac gtc acg ctg ggc tct gac gtg gaa gag gac ctg acg atg      768
Phe Met His Val Thr Leu Gly Ser Asp Val Glu Glu Asp Leu Thr Met
                245                 250                 255 acc cgc aac ccg caa ccc ttc atg cgc ccc cac gag cgc aac ggc ttt      816
Thr Arg Asn Pro Gln Pro Phe Met Arg Pro His Glu Arg Asn Gly Phe
            260                 265                 270 acg gtg ttg tgt ccc aaa aat atg ata atc aaa ccg ggc aag atc tcg      864
Thr Val Leu Cys Pro Lys Asn Met Ile Ile Lys Pro Gly Lys Ile Ser
        275                 280                 285 cac atc atg ctg gat gtg gct ttt acc tca cac gag cat ttt ggg ctg      912
His Ile Met Leu Asp Val Ala Phe Thr Ser His Glu His Phe Gly Leu
        290                 295                 300 ctg tgt ccc aag agc atc ccg ggc ctg agc atc tca ggt aac ctg ttg      960
Leu Cys Pro Lys Ser Ile Pro Gly Leu Ser Ile Ser Gly Asn Leu Leu
305                 310                 315                 320 atg aac ggg cag cag atc ttc ctg gag gta caa gcc ata cgc gag acc     1008
Met Asn Gly Gln Gln Ile Phe Leu Glu Val Gln Ala Ile Arg Glu Thr
                325                 330                 335 gtg gaa ctg cgt cag tac gat ccc gtg gct gcg ctc ttc ttt ttc gat     1056
Val Glu Leu Arg Gln Tyr Asp Pro Val Ala Ala Leu Phe Phe Phe Asp
            340                 345                 350 atc gac ttg ctg ctg cag cgc ggg cct cag tac agc gag cac ccc acc     1104
Ile Asp Leu Leu Leu Gln Arg Gly Pro Gln Tyr Ser Glu His Pro Thr
        355                 360                 365 ttc acc agc cag tat cgc atc cag ggc aag ctt gag tac cga cac acc     1152
Phe Thr Ser Gln Tyr Arg Ile Gln Gly Lys Leu Glu Tyr Arg His Thr
        370                 375                 380 tgg gac cgg cac gac gag ggt gcc gcc cag ggc gac gac gac gtc tgg     1200
Trp Asp Arg His Asp Glu Gly Ala Ala Gln Gly Asp Asp Asp Val Trp
385                 390                 395                 400 acc agc gga tcg gac tcc gac gaa gaa ctc gta acc acc gag cgc aag     1248
Thr Ser Gly Ser Asp Ser Asp Glu Glu Leu Val Thr Thr Glu Arg Lys
                405                 410                 415 acg ccc cgc gtc acc ggc ggc ggc gcc atg gcg ggc gcc tcc act tcc     1296
Thr Pro Arg Val Thr Gly Gly Gly Ala Met Ala Gly Ala Ser Thr Ser
```

```
                    420             425             430
gcg ggc cgc aaa cgc aaa tca gca tcc tcg gcg acg gcg tgc acg tcg    1344
Ala Gly Arg Lys Arg Lys Ser Ala Ser Ser Ala Thr Ala Cys Thr Ser
            435             440             445 ggc gtt atg aca cgc ggc cgc ctt aag gcc gag tcc acc gtc gcg ccc    1392
Gly Val Met Thr Arg Gly Arg Leu Lys Ala Glu Ser Thr Val Ala Pro
        450             455             460 gaa gag gac acc gac gag gat tcc gac aac gaa atc cac aat ccg gcc    1440
Glu Glu Asp Thr Asp Glu Asp Ser Asp Asn Glu Ile His Asn Pro Ala
465             470             475             480 gtg ttc acc tgg ccg ccc tgg cag gcc ggc atc ctg gcc cgc aac ctg    1488
Val Phe Thr Trp Pro Pro Trp Gln Ala Gly Ile Leu Ala Arg Asn Leu
            485             490             495 gtg ccc atg gtg gct acg gtt cag ggt cag aat ctg aag tac cag gaa    1536
Val Pro Met Val Ala Thr Val Gln Gly Gln Asn Leu Lys Tyr Gln Glu
        500             505             510 ttc ttc tgg gac gcc aac gac atc tac cgc atc ttc gcc gaa ttg gaa    1584
Phe Phe Trp Asp Ala Asn Asp Ile Tyr Arg Ile Phe Ala Glu Leu Glu
            515             520             525 ggc gta tgg cag ccc gct gcg caa ccc aaa cgt cgc cgc cac cgg caa    1632
Gly Val Trp Gln Pro Ala Ala Gln Pro Lys Arg Arg Arg His Arg Gln
        530             535             540 gac gcc ttg ccc ggg cca tgc atc gcc tcg acg ccc aaa aag cac cga    1680
Asp Ala Leu Pro Gly Pro Cys Ile Ala Ser Thr Pro Lys Lys His Arg
545             550             555             560 ggt gag tcc tct gcc aag aga aag atg gac cct gat aat cct gac gag    1728
Gly Glu Ser Ser Ala Lys Arg Lys Met Asp Pro Asp Asn Pro Asp Glu
            565             570             575 ggc cct tcc tcc aag gtg cca cgg ccc gag aca ccc gtg acc aag gcc    1776
Gly Pro Ser Ser Lys Val Pro Arg Pro Glu Thr Pro Val Thr Lys Ala
        580             585             590 acg acg ttc ctg cag act atg ttg agg aag gag gtt aac agt cag ctg    1824
Thr Thr Phe Leu Gln Thr Met Leu Arg Lys Glu Val Asn Ser Gln Leu
            595             600             605 agt ctg gga gac ccg ctg ttt cca gag ttg gcc gaa gaa tcc ctc aaa    1872
Ser Leu Gly Asp Pro Leu Phe Pro Glu Leu Ala Glu Glu Ser Leu Lys
610             615             620 act ttt gaa caa gtg acc gag gat tgc aac gag aac ccc gag aaa gat    1920
Thr Phe Glu Gln Val Thr Glu Asp Cys Asn Glu Asn Pro Glu Lys Asp
625             630             635             640 gtc ctg gca gaa ctc gtc aaa cag att aag gtt cga gtg gac atg gtg    1968
Val Leu Ala Glu Leu Val Lys Gln Ile Lys Val Arg Val Asp Met Val
            645             650             655 cgg cat aga atc aag gag cac atg ctg aaa aaa tat acc cag acg gaa    2016
Arg His Arg Ile Lys Glu His Met Leu Lys Lys Tyr Thr Gln Thr Glu
        660             665             670 gag aaa ttc act ggc gcc ttt aat atg atg gga gga tgt ttg cag aat    2064
Glu Lys Phe Thr Gly Ala Phe Asn Met Met Gly Gly Cys Leu Gln Asn
            675             680             685 gcc tta gat atc tta gat aag gtt cat gag cct ttc gag gag atg aag    2112
Ala Leu Asp Ile Leu Asp Lys Val His Glu Pro Phe Glu Glu Met Lys
        690             695             700 tgt att ggg cta act atg cag agc atg tat gag aac tac att gta cct    2160
Cys Ile Gly Leu Thr Met Gln Ser Met Tyr Glu Asn Tyr Ile Val Pro
705             710             715             720 gag gat aag cgg gag atg tgg atg gct tgt att aag gag ctg cat gat    2208
Glu Asp Lys Arg Glu Met Trp Met Ala Cys Ile Lys Glu Leu His Asp
            725             730             735 gtg agc aag ggc gcc gct aac aag ttg ggg ggt gca ctg cag gct aag    2256
```

-continued

```
                Val Ser Lys Gly Ala Ala Asn Lys Leu Gly Gly Ala Leu Gln Ala Lys
                            740                 745                 750 gcc cgt gct aaa aag gat gaa ctt agg aga aag atg atg tat atg tgc         2304
Ala Arg Ala Lys Lys Asp Glu Leu Arg Arg Lys Met Met Tyr Met Cys
            755                 760                 765 tac agg aat ata gag ttc ttt acc aag aac tca gcc ttc cct aag acc         2352
Tyr Arg Asn Ile Glu Phe Phe Thr Lys Asn Ser Ala Phe Pro Lys Thr
            770                 775                 780 acc aat ggc tgc agt cag gcc atg gcg gca ctg cag aac ttg cct cag         2400
Thr Asn Gly Cys Ser Gln Ala Met Ala Ala Leu Gln Asn Leu Pro Gln
785                 790                 795                 800 tgc tcc cct gat gag att atg gct tat gcc cag aaa ata ttt aag att         2448
Cys Ser Pro Asp Glu Ile Met Ala Tyr Ala Gln Lys Ile Phe Lys Ile
                805                 810                 815 ttg gat gag gag aga gac aag gtg ctc acg cac att gat cac ata ttt         2496
Leu Asp Glu Glu Arg Asp Lys Val Leu Thr His Ile Asp His Ile Phe
                820                 825                 830 atg gat atc ctc act aca tgt gtg gaa aca atg tgt aat gag tac aag         2544
Met Asp Ile Leu Thr Thr Cys Val Glu Thr Met Cys Asn Glu Tyr Lys
            835                 840                 845 gtc act agt gac gct tgt atg atg acc atg tac ggg ggc atc tct ctc         2592
Val Thr Ser Asp Ala Cys Met Met Thr Met Tyr Gly Gly Ile Ser Leu
850                 855                 860 tta agt gag ttc tgt cgg gtg ctg tgc tgc tat gtc tta gag gag act         2640
Leu Ser Glu Phe Cys Arg Val Leu Cys Cys Tyr Val Leu Glu Glu Thr
865                 870                 875                 880 agt gtg atg ctg gcc aag cgg cct ctg ata acc aag cct gag gtt atc         2688
Ser Val Met Leu Ala Lys Arg Pro Leu Ile Thr Lys Pro Glu Val Ile
                885                 890                 895 agt gta atg aag cgc cgc att gag gag atc tgc atg aag gtc ttt gcc         2736
Ser Val Met Lys Arg Arg Ile Glu Glu Ile Cys Met Lys Val Phe Ala
            900                 905                 910 cag tac att ctg ggg gcc gat cct ctg aga gtc tgc tct cct agt gtg         2784
Gln Tyr Ile Leu Gly Ala Asp Pro Leu Arg Val Cys Ser Pro Ser Val
            915                 920                 925 gat gac cta cgg gcc gtc gcc gag gag tca gat gag gaa gag gct att         2832
Asp Asp Leu Arg Ala Val Ala Glu Glu Ser Asp Glu Glu Glu Ala Ile
        930                 935                 940 gta gcc tac act ttg gcc acc gct ggt gtc agc tcc tct gat tct ctg         2880
Val Ala Tyr Thr Leu Ala Thr Ala Gly Val Ser Ser Ser Asp Ser Leu
945                 950                 955                 960 gtg tca ccc cca gag tcc cct gta ccc gcg act atc cct ctg tcc tca         2928
Val Ser Pro Pro Glu Ser Pro Val Pro Ala Thr Ile Pro Leu Ser Ser
                965                 970                 975 gta att gtg gct gag aac agt gat cag gaa gaa agt gag cag agt gat         2976
Val Ile Val Ala Glu Asn Ser Asp Gln Glu Glu Ser Glu Gln Ser Asp
            980                 985                 990 gag gaa gag gag gag ggt gct cag  gag gag cgg gag gac  act gtg tct       3024
Glu Glu Glu Glu Glu Gly Ala Gln  Glu Glu Arg Glu Asp  Thr Val Ser
            995                  1000                 1005 gtc aag tct gag cca gtg tct  gag ata gag gaa gtt  gcc cca gag           3069
Val Lys Ser Glu Pro Val Ser  Glu Ile Glu Glu Val  Ala Pro Glu
        1010                 1015                 1020 gaa gag gag gat ggt gct gag  gaa ccc acc gcc tct  gga ggc aag           3114
Glu Glu Glu Asp Gly Ala Glu  Glu Pro Thr Ala Ser  Gly Gly Lys
    1025                 1030                 1035 agc acc cac cct atg gtg act  aga agc aag gct gac  cag taa               3156
Ser Thr His Pro Met Val Thr  Arg Ser Lys Ala Asp  Gln
    1040                 1045                 1050
```

<210> SEQ ID NO 4
<211> LENGTH: 1051
<212> TYPE: PRT
<213> ORGANISM: Artificial
<220> FEATURE:
<223> OTHER INFORMATION: hCMV pp65-IE1 fusion

<400> SEQUENCE: 4

```
Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365
```

-continued

```
Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                    405                 410                 415

Thr Pro Arg Val Thr Gly Gly Ala Met Ala Gly Ala Ser Thr Ser
                420                 425                 430

Ala Gly Arg Lys Arg Lys Ser Ala Ser Ser Ala Thr Ala Cys Thr Ser
        435                 440                 445

Gly Val Met Thr Arg Gly Arg Leu Lys Ala Glu Ser Thr Val Ala Pro
    450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
                500                 505                 510

Phe Phe Trp Asp Ala Asn Asp Ile Tyr Arg Ile Phe Ala Glu Leu Glu
            515                 520                 525

Gly Val Trp Gln Pro Ala Ala Gln Pro Lys Arg Arg Arg His Arg Gln
    530                 535                 540

Asp Ala Leu Pro Gly Pro Cys Ile Ala Ser Thr Pro Lys Lys His Arg
545                 550                 555                 560

Gly Glu Ser Ser Ala Lys Arg Lys Met Asp Pro Asn Pro Asp Glu
                565                 570                 575

Gly Pro Ser Ser Lys Val Pro Arg Pro Glu Thr Pro Val Thr Lys Ala
            580                 585                 590

Thr Thr Phe Leu Gln Thr Met Leu Arg Lys Glu Val Asn Ser Gln Leu
            595                 600                 605

Ser Leu Gly Asp Pro Leu Phe Pro Glu Leu Ala Glu Glu Ser Leu Lys
    610                 615                 620

Thr Phe Glu Gln Val Thr Glu Asp Cys Asn Glu Asn Pro Glu Lys Asp
625                 630                 635                 640

Val Leu Ala Glu Leu Val Lys Gln Ile Lys Val Arg Val Asp Met Val
                645                 650                 655

Arg His Arg Ile Lys Glu His Met Leu Lys Lys Tyr Thr Gln Thr Glu
                660                 665                 670

Glu Lys Phe Thr Gly Ala Phe Asn Met Met Gly Gly Cys Leu Gln Asn
        675                 680                 685

Ala Leu Asp Ile Leu Asp Lys Val His Glu Pro Phe Glu Glu Met Lys
    690                 695                 700

Cys Ile Gly Leu Thr Met Gln Ser Met Tyr Glu Asn Tyr Ile Val Pro
705                 710                 715                 720

Glu Asp Lys Arg Glu Met Trp Met Ala Cys Ile Lys Glu Leu His Asp
                725                 730                 735

Val Ser Lys Gly Ala Ala Asn Lys Leu Gly Gly Ala Leu Gln Ala Lys
            740                 745                 750

Ala Arg Ala Lys Lys Asp Glu Leu Arg Arg Lys Met Met Tyr Met Cys
        755                 760                 765

Tyr Arg Asn Ile Glu Phe Phe Thr Lys Asn Ser Ala Phe Pro Lys Thr
    770                 775                 780

Thr Asn Gly Cys Ser Gln Ala Met Ala Ala Leu Gln Asn Leu Pro Gln
```

```
                    785                 790                 795                 800

Cys Ser Pro Asp Glu Ile Met Ala Tyr Ala Gln Lys Ile Phe Lys Ile
                            805                 810                 815

Leu Asp Glu Glu Arg Asp Lys Val Leu Thr His Ile Asp His Ile Phe
                        820                 825                 830

Met Asp Ile Leu Thr Thr Cys Val Glu Thr Met Cys Asn Glu Tyr Lys
                        835                 840                 845

Val Thr Ser Asp Ala Cys Met Met Thr Met Tyr Gly Gly Ile Ser Leu
                    850                 855                 860

Leu Ser Glu Phe Cys Arg Val Leu Cys Cys Tyr Val Leu Glu Glu Thr
            865                 870                 875                 880

Ser Val Met Leu Ala Lys Arg Pro Leu Ile Thr Lys Pro Glu Val Ile
                            885                 890                 895

Ser Val Met Lys Arg Arg Ile Glu Glu Ile Cys Met Lys Val Phe Ala
                            900                 905                 910

Gln Tyr Ile Leu Gly Ala Asp Pro Leu Arg Val Cys Ser Pro Ser Val
                            915                 920                 925

Asp Asp Leu Arg Ala Val Ala Glu Glu Ser Asp Glu Glu Ala Ile
                        930                 935                 940

Val Ala Tyr Thr Leu Ala Thr Ala Gly Val Ser Ser Asp Ser Leu
            945                 950                 955                 960

Val Ser Pro Pro Glu Ser Pro Val Pro Ala Thr Ile Pro Leu Ser Ser
                            965                 970                 975

Val Ile Val Ala Glu Asn Ser Asp Gln Glu Glu Ser Gln Ser Asp
                        980                 985                 990

Glu Glu Glu Glu Glu Gly Ala Gln Glu Glu Arg Glu Asp Thr Val Ser
                        995                 1000                1005

Val Lys Ser Glu Pro Val Ser Glu Ile Glu Glu Val Ala Pro Glu
                        1010                1015                1020

Glu Glu Asp Gly Ala Glu Glu Pro Thr Ala Ser Gly Gly Lys
                        1025                1030                1035

Ser Thr His Pro Met Val Thr Arg Ser Lys Ala Asp Gln
                        1040                1045                1050

<210> SEQ ID NO 5
<211> LENGTH: 15
<212> TYPE: PRT
<213> ORGANISM: Human cytomegalovirus

<400> SEQUENCE: 5

Met Glu Ser Arg Gly Arg Arg Cys Pro Glu Met Ile Ser Val Leu
1               5                   10                  15

<210> SEQ ID NO 6
<211> LENGTH: 15
<212> TYPE: PRT
<213> ORGANISM: Human cytomegalovirus

<400> SEQUENCE: 6

Gly Arg Arg Cys Pro Glu Met Ile Ser Val Leu Gly Pro Ile Ser
1               5                   10                  15

<210> SEQ ID NO 7
<211> LENGTH: 15
<212> TYPE: PRT
<213> ORGANISM: Human cytomegalovirus

<400> SEQUENCE: 7
```

-continued

```
Pro Glu Met Ile Ser Val Leu Gly Pro Ile Ser Gly His Val Leu
1               5                   10                  15

<210> SEQ ID NO 8
<211> LENGTH: 15
<212> TYPE: PRT
<213> ORGANISM: Human cytomegalovirus

<400> SEQUENCE: 8

Ser Val Leu Gly Pro Ile Ser Gly His Val Leu Lys Ala Val Phe
1               5                   10                  15

<210> SEQ ID NO 9
<211> LENGTH: 15
<212> TYPE: PRT
<213> ORGANISM: Human cytomegalovirus

<400> SEQUENCE: 9

Pro Ile Ser Gly His Val Leu Lys Ala Val Phe Ser Arg Gly Asp
1               5                   10                  15

<210> SEQ ID NO 10
<211> LENGTH: 15
<212> TYPE: PRT
<213> ORGANISM: Human cytomegalovirus

<400> SEQUENCE: 10

His Val Leu Lys Ala Val Phe Ser Arg Gly Asp Thr Pro Val Leu
1               5                   10                  15

<210> SEQ ID NO 11
<211> LENGTH: 15
<212> TYPE: PRT
<213> ORGANISM: Human cytomegalovirus

<400> SEQUENCE: 11

Ala Val Phe Ser Arg Gly Asp Thr Pro Val Leu Pro His Glu Thr
1               5                   10                  15

<210> SEQ ID NO 12
<211> LENGTH: 15
<212> TYPE: PRT
<213> ORGANISM: Human cytomegalovirus

<400> SEQUENCE: 12

Arg Gly Asp Thr Pro Val Leu Pro His Glu Thr Arg Leu Leu Gln
1               5                   10                  15

<210> SEQ ID NO 13
<211> LENGTH: 15
<212> TYPE: PRT
<213> ORGANISM: Human cytomegalovirus

<400> SEQUENCE: 13

Pro Val Leu Pro His Glu Thr Arg Leu Leu Gln Thr Gly Ile His
1               5                   10                  15

<210> SEQ ID NO 14
<211> LENGTH: 15
<212> TYPE: PRT
<213> ORGANISM: Human cytomegalovirus

<400> SEQUENCE: 14

His Glu Thr Arg Leu Leu Gln Thr Gly Ile His Val Arg Val Ser
```

```
1               5                   10                  15
```

<210> SEQ ID NO 15
<211> LENGTH: 15
<212> TYPE: PRT
<213> ORGANISM: Human cytomegalovirus

<400> SEQUENCE: 15

```
Leu Leu Gln Thr Gly Ile His Val Arg Val Ser Gln Pro Ser Leu
1               5                   10                  15
```

<210> SEQ ID NO 16
<211> LENGTH: 15
<212> TYPE: PRT
<213> ORGANISM: Human cytomegalovirus

<400> SEQUENCE: 16

```
Gly Ile His Val Arg Val Ser Gln Pro Ser Leu Ile Leu Val Ser
1               5                   10                  15
```

<210> SEQ ID NO 17
<211> LENGTH: 15
<212> TYPE: PRT
<213> ORGANISM: Human cytomegalovirus

<400> SEQUENCE: 17

```
Arg Val Ser Gln Pro Ser Leu Ile Leu Val Ser Gln Tyr Thr Pro
1               5                   10                  15
```

<210> SEQ ID NO 18
<211> LENGTH: 15
<212> TYPE: PRT
<213> ORGANISM: Human cytomegalovirus

<400> SEQUENCE: 18

```
Pro Ser Leu Ile Leu Val Ser Gln Tyr Thr Pro Asp Ser Thr Pro
1               5                   10                  15
```

<210> SEQ ID NO 19
<211> LENGTH: 15
<212> TYPE: PRT
<213> ORGANISM: Human cytomegalovirus

<400> SEQUENCE: 19

```
Leu Val Ser Gln Tyr Thr Pro Asp Ser Thr Pro Cys His Arg Gly
1               5                   10                  15
```

<210> SEQ ID NO 20
<211> LENGTH: 15
<212> TYPE: PRT
<213> ORGANISM: Human cytomegalovirus

<400> SEQUENCE: 20

```
Tyr Thr Pro Asp Ser Thr Pro Cys His Arg Gly Asp Asn Gln Leu
1               5                   10                  15
```

<210> SEQ ID NO 21
<211> LENGTH: 15
<212> TYPE: PRT
<213> ORGANISM: Human cytomegalovirus

<400> SEQUENCE: 21

```
Ser Thr Pro Cys His Arg Gly Asp Asn Gln Leu Gln Val Gln His
1               5                   10                  15
```

```
<210> SEQ ID NO 22
<211> LENGTH: 15
<212> TYPE: PRT
<213> ORGANISM: Human cytomegalovirus

<400> SEQUENCE: 22

His Arg Gly Asp Asn Gln Leu Gln Val Gln His Thr Tyr Phe Thr
1               5                   10                  15

<210> SEQ ID NO 23
<211> LENGTH: 15
<212> TYPE: PRT
<213> ORGANISM: Human cytomegalovirus

<400> SEQUENCE: 23

Asn Gln Leu Gln Val Gln His Thr Tyr Phe Thr Gly Ser Glu Val
1               5                   10                  15

<210> SEQ ID NO 24
<211> LENGTH: 15
<212> TYPE: PRT
<213> ORGANISM: Human cytomegalovirus

<400> SEQUENCE: 24

Val Gln His Thr Tyr Phe Thr Gly Ser Glu Val Glu Asn Val Ser
1               5                   10                  15

<210> SEQ ID NO 25
<211> LENGTH: 15
<212> TYPE: PRT
<213> ORGANISM: Human cytomegalovirus

<400> SEQUENCE: 25

Tyr Phe Thr Gly Ser Glu Val Glu Asn Val Ser Val Asn Val His
1               5                   10                  15

<210> SEQ ID NO 26
<211> LENGTH: 15
<212> TYPE: PRT
<213> ORGANISM: Human cytomegalovirus

<400> SEQUENCE: 26

Ser Glu Val Glu Asn Val Ser Val Asn Val His Asn Pro Thr Gly
1               5                   10                  15

<210> SEQ ID NO 27
<211> LENGTH: 15
<212> TYPE: PRT
<213> ORGANISM: Human cytomegalovirus

<400> SEQUENCE: 27

Asn Val Ser Val Asn Val His Asn Pro Thr Gly Arg Ser Ile Cys
1               5                   10                  15

<210> SEQ ID NO 28
<211> LENGTH: 15
<212> TYPE: PRT
<213> ORGANISM: Human cytomegalovirus

<400> SEQUENCE: 28

Asn Val His Asn Pro Thr Gly Arg Ser Ile Cys Pro Ser Gln Glu
1               5                   10                  15

<210> SEQ ID NO 29
```

```
<211> LENGTH: 15
<212> TYPE: PRT
<213> ORGANISM: Human cytomegalovirus

<400> SEQUENCE: 29

Pro Thr Gly Arg Ser Ile Cys Pro Ser Gln Glu Pro Met Ser Ile
1               5                  10                  15

<210> SEQ ID NO 30
<211> LENGTH: 15
<212> TYPE: PRT
<213> ORGANISM: Human cytomegalovirus

<400> SEQUENCE: 30

Ser Ile Cys Pro Ser Gln Glu Pro Met Ser Ile Tyr Val Tyr Ala
1               5                  10                  15

<210> SEQ ID NO 31
<211> LENGTH: 15
<212> TYPE: PRT
<213> ORGANISM: Human cytomegalovirus

<400> SEQUENCE: 31

Ser Gln Glu Pro Met Ser Ile Tyr Val Tyr Ala Leu Pro Leu Lys
1               5                  10                  15

<210> SEQ ID NO 32
<211> LENGTH: 15
<212> TYPE: PRT
<213> ORGANISM: Human cytomegalovirus

<400> SEQUENCE: 32

Met Ser Ile Tyr Val Tyr Ala Leu Pro Leu Lys Met Leu Asn Ile
1               5                  10                  15

<210> SEQ ID NO 33
<211> LENGTH: 15
<212> TYPE: PRT
<213> ORGANISM: Human cytomegalovirus

<400> SEQUENCE: 33

Val Tyr Ala Leu Pro Leu Lys Met Leu Asn Ile Pro Ser Ile Asn
1               5                  10                  15

<210> SEQ ID NO 34
<211> LENGTH: 15
<212> TYPE: PRT
<213> ORGANISM: Human cytomegalovirus

<400> SEQUENCE: 34

Pro Leu Lys Met Leu Asn Ile Pro Ser Ile Asn Val His His Tyr
1               5                  10                  15

<210> SEQ ID NO 35
<211> LENGTH: 15
<212> TYPE: PRT
<213> ORGANISM: Human cytomegalovirus

<400> SEQUENCE: 35

Leu Asn Ile Pro Ser Ile Asn Val His His Tyr Pro Ser Ala Ala
1               5                  10                  15

<210> SEQ ID NO 36
<211> LENGTH: 15
<212> TYPE: PRT
```

<213> ORGANISM: Human cytomegalovirus

<400> SEQUENCE: 36

Ser Ile Asn Val His His Tyr Pro Ser Ala Ala Glu Arg Lys His
1               5                   10                  15

<210> SEQ ID NO 37
<211> LENGTH: 15
<212> TYPE: PRT
<213> ORGANISM: Human cytomegalovirus

<400> SEQUENCE: 37

His His Tyr Pro Ser Ala Ala Glu Arg Lys His Arg His Leu Pro
1               5                   10                  15

<210> SEQ ID NO 38
<211> LENGTH: 15
<212> TYPE: PRT
<213> ORGANISM: Human cytomegalovirus

<400> SEQUENCE: 38

Ser Ala Ala Glu Arg Lys His Arg His Leu Pro Val Ala Asp Ala
1               5                   10                  15

<210> SEQ ID NO 39
<211> LENGTH: 15
<212> TYPE: PRT
<213> ORGANISM: Human cytomegalovirus

<400> SEQUENCE: 39

Arg Lys His Arg His Leu Pro Val Ala Asp Ala Val Ile His Ala
1               5                   10                  15

<210> SEQ ID NO 40
<211> LENGTH: 15
<212> TYPE: PRT
<213> ORGANISM: Human cytomegalovirus

<400> SEQUENCE: 40

His Leu Pro Val Ala Asp Ala Val Ile His Ala Ser Gly Lys Gln
1               5                   10                  15

<210> SEQ ID NO 41
<211> LENGTH: 15
<212> TYPE: PRT
<213> ORGANISM: Human cytomegalovirus

<400> SEQUENCE: 41

Ala Asp Ala Val Ile His Ala Ser Gly Lys Gln Met Trp Gln Ala
1               5                   10                  15

<210> SEQ ID NO 42
<211> LENGTH: 15
<212> TYPE: PRT
<213> ORGANISM: Human cytomegalovirus

<400> SEQUENCE: 42

Ile His Ala Ser Gly Lys Gln Met Trp Gln Ala Arg Leu Thr Val
1               5                   10                  15

<210> SEQ ID NO 43
<211> LENGTH: 15
<212> TYPE: PRT
<213> ORGANISM: Human cytomegalovirus -continued

```
<400> SEQUENCE: 43

Gly Lys Gln Met Trp Gln Ala Arg Leu Thr Val Ser Gly Leu Ala
1               5                   10                  15

<210> SEQ ID NO 44
<211> LENGTH: 15
<212> TYPE: PRT
<213> ORGANISM: Human cytomegalovirus

<400> SEQUENCE: 44

Trp Gln Ala Arg Leu Thr Val Ser Gly Leu Ala Trp Thr Arg Gln
1               5                   10                  15

<210> SEQ ID NO 45
<211> LENGTH: 15
<212> TYPE: PRT
<213> ORGANISM: Human cytomegalovirus

<400> SEQUENCE: 45

Leu Thr Val Ser Gly Leu Ala Trp Thr Arg Gln Gln Asn Gln Trp
1               5                   10                  15

<210> SEQ ID NO 46
<211> LENGTH: 15
<212> TYPE: PRT
<213> ORGANISM: Human cytomegalovirus

<400> SEQUENCE: 46

Gly Leu Ala Trp Thr Arg Gln Gln Asn Gln Trp Lys Glu Pro Asp
1               5                   10                  15

<210> SEQ ID NO 47
<211> LENGTH: 15
<212> TYPE: PRT
<213> ORGANISM: Human cytomegalovirus

<400> SEQUENCE: 47

Thr Arg Gln Gln Asn Gln Trp Lys Glu Pro Asp Val Tyr Tyr Thr
1               5                   10                  15

<210> SEQ ID NO 48
<211> LENGTH: 15
<212> TYPE: PRT
<213> ORGANISM: Human cytomegalovirus

<400> SEQUENCE: 48

Asn Gln Trp Lys Glu Pro Asp Val Tyr Tyr Thr Ser Ala Phe Val
1               5                   10                  15

<210> SEQ ID NO 49
<211> LENGTH: 15
<212> TYPE: PRT
<213> ORGANISM: Human cytomegalovirus

<400> SEQUENCE: 49

Glu Pro Asp Val Tyr Tyr Thr Ser Ala Phe Val Phe Pro Thr Lys
1               5                   10                  15

<210> SEQ ID NO 50
<211> LENGTH: 15
<212> TYPE: PRT
<213> ORGANISM: Human cytomegalovirus

<400> SEQUENCE: 50
```

Tyr Tyr Thr Ser Ala Phe Val Phe Pro Thr Lys Asp Val Ala Leu
1               5                   10                  15

<210> SEQ ID NO 51
<211> LENGTH: 15
<212> TYPE: PRT
<213> ORGANISM: Human cytomegalovirus

<400> SEQUENCE: 51

Ala Phe Val Phe Pro Thr Lys Asp Val Ala Leu Arg His Val Val
1               5                   10                  15

<210> SEQ ID NO 52
<211> LENGTH: 15
<212> TYPE: PRT
<213> ORGANISM: Human cytomegalovirus

<400> SEQUENCE: 52

Pro Thr Lys Asp Val Ala Leu Arg His Val Val Cys Ala His Glu
1               5                   10                  15

<210> SEQ ID NO 53
<211> LENGTH: 15
<212> TYPE: PRT
<213> ORGANISM: Human cytomegalovirus

<400> SEQUENCE: 53

Val Ala Leu Arg His Val Val Cys Ala His Glu Leu Val Cys Ser
1               5                   10                  15

<210> SEQ ID NO 54
<211> LENGTH: 15
<212> TYPE: PRT
<213> ORGANISM: Human cytomegalovirus

<400> SEQUENCE: 54

His Val Val Cys Ala His Glu Leu Val Cys Ser Met Glu Asn Thr
1               5                   10                  15

<210> SEQ ID NO 55
<211> LENGTH: 15
<212> TYPE: PRT
<213> ORGANISM: Human cytomegalovirus

<400> SEQUENCE: 55

Ala His Glu Leu Val Cys Ser Met Glu Asn Thr Arg Ala Thr Lys
1               5                   10                  15

<210> SEQ ID NO 56
<211> LENGTH: 15
<212> TYPE: PRT
<213> ORGANISM: Human cytomegalovirus

<400> SEQUENCE: 56

Val Cys Ser Met Glu Asn Thr Arg Ala Thr Lys Met Gln Val Ile
1               5                   10                  15

<210> SEQ ID NO 57
<211> LENGTH: 15
<212> TYPE: PRT
<213> ORGANISM: Human cytomegalovirus

<400> SEQUENCE: 57

Glu Asn Thr Arg Ala Thr Lys Met Gln Val Ile Gly Asp Gln Tyr
1               5                   10                  15

<210> SEQ ID NO 58
<211> LENGTH: 15
<212> TYPE: PRT
<213> ORGANISM: Human cytomegalovirus

<400> SEQUENCE: 58

Ala Thr Lys Met Gln Val Ile Gly Asp Gln Tyr Val Lys Val Tyr
1               5                   10                  15

<210> SEQ ID NO 59
<211> LENGTH: 15
<212> TYPE: PRT
<213> ORGANISM: Human cytomegalovirus

<400> SEQUENCE: 59

Gln Val Ile Gly Asp Gln Tyr Val Lys Val Tyr Leu Glu Ser Phe
1               5                   10                  15

<210> SEQ ID NO 60
<211> LENGTH: 15
<212> TYPE: PRT
<213> ORGANISM: Human cytomegalovirus

<400> SEQUENCE: 60

Asp Gln Tyr Val Lys Val Tyr Leu Glu Ser Phe Cys Glu Asp Val
1               5                   10                  15

<210> SEQ ID NO 61
<211> LENGTH: 15
<212> TYPE: PRT
<213> ORGANISM: Human cytomegalovirus

<400> SEQUENCE: 61

Lys Val Tyr Leu Glu Ser Phe Cys Glu Asp Val Pro Ser Gly Lys
1               5                   10                  15

<210> SEQ ID NO 62
<211> LENGTH: 15
<212> TYPE: PRT
<213> ORGANISM: Human cytomegalovirus

<400> SEQUENCE: 62

Glu Ser Phe Cys Glu Asp Val Pro Ser Gly Lys Leu Phe Met His
1               5                   10                  15

<210> SEQ ID NO 63
<211> LENGTH: 15
<212> TYPE: PRT
<213> ORGANISM: Human cytomegalovirus

<400> SEQUENCE: 63

Glu Asp Val Pro Ser Gly Lys Leu Phe Met His Val Thr Leu Gly
1               5                   10                  15

<210> SEQ ID NO 64
<211> LENGTH: 15
<212> TYPE: PRT
<213> ORGANISM: Human cytomegalovirus

<400> SEQUENCE: 64

Ser Gly Lys Leu Phe Met His Val Thr Leu Gly Ser Asp Val Glu
1               5                   10                  15

```
<210> SEQ ID NO 65
<211> LENGTH: 15
<212> TYPE: PRT
<213> ORGANISM: Human cytomegalovirus

<400> SEQUENCE: 65

Phe Met His Val Thr Leu Gly Ser Asp Val Glu Glu Asp Leu Thr
1               5                   10                  15

<210> SEQ ID NO 66
<211> LENGTH: 15
<212> TYPE: PRT
<213> ORGANISM: Human cytomegalovirus

<400> SEQUENCE: 66

Thr Leu Gly Ser Asp Val Glu Glu Asp Leu Thr Met Thr Arg Asn
1               5                   10                  15

<210> SEQ ID NO 67
<211> LENGTH: 15
<212> TYPE: PRT
<213> ORGANISM: Human cytomegalovirus

<400> SEQUENCE: 67

Asp Val Glu Glu Asp Leu Thr Met Thr Arg Asn Pro Gln Pro Phe
1               5                   10                  15

<210> SEQ ID NO 68
<211> LENGTH: 15
<212> TYPE: PRT
<213> ORGANISM: Human cytomegalovirus

<400> SEQUENCE: 68

Asp Leu Thr Met Thr Arg Asn Pro Gln Pro Phe Met Arg Pro His
1               5                   10                  15

<210> SEQ ID NO 69
<211> LENGTH: 15
<212> TYPE: PRT
<213> ORGANISM: Human cytomegalovirus

<400> SEQUENCE: 69

Thr Arg Asn Pro Gln Pro Phe Met Arg Pro His Glu Arg Asn Gly
1               5                   10                  15

<210> SEQ ID NO 70
<211> LENGTH: 15
<212> TYPE: PRT
<213> ORGANISM: Human cytomegalovirus

<400> SEQUENCE: 70

Gln Pro Phe Met Arg Pro His Glu Arg Asn Gly Phe Thr Val Leu
1               5                   10                  15

<210> SEQ ID NO 71
<211> LENGTH: 15
<212> TYPE: PRT
<213> ORGANISM: Human cytomegalovirus

<400> SEQUENCE: 71

Arg Pro His Glu Arg Asn Gly Phe Thr Val Leu Cys Pro Lys Asn
1               5                   10                  15

<210> SEQ ID NO 72
<211> LENGTH: 15
```

```
<212> TYPE: PRT
<213> ORGANISM: Human cytomegalovirus

<400> SEQUENCE: 72

Arg Asn Gly Phe Thr Val Leu Cys Pro Lys Asn Met Ile Ile Lys
1               5                   10                  15

<210> SEQ ID NO 73
<211> LENGTH: 15
<212> TYPE: PRT
<213> ORGANISM: Human cytomegalovirus

<400> SEQUENCE: 73

Thr Val Leu Cys Pro Lys Asn Met Ile Ile Lys Pro Gly Lys Ile
1               5                   10                  15

<210> SEQ ID NO 74
<211> LENGTH: 15
<212> TYPE: PRT
<213> ORGANISM: Human cytomegalovirus

<400> SEQUENCE: 74

Pro Lys Asn Met Ile Ile Lys Pro Gly Lys Ile Ser His Ile Met
1               5                   10                  15

<210> SEQ ID NO 75
<211> LENGTH: 15
<212> TYPE: PRT
<213> ORGANISM: Human cytomegalovirus

<400> SEQUENCE: 75

Ile Ile Lys Pro Gly Lys Ile Ser His Ile Met Leu Asp Val Ala
1               5                   10                  15

<210> SEQ ID NO 76
<211> LENGTH: 15
<212> TYPE: PRT
<213> ORGANISM: Human cytomegalovirus

<400> SEQUENCE: 76

Gly Lys Ile Ser His Ile Met Leu Asp Val Ala Phe Thr Ser His
1               5                   10                  15

<210> SEQ ID NO 77
<211> LENGTH: 15
<212> TYPE: PRT
<213> ORGANISM: Human cytomegalovirus

<400> SEQUENCE: 77

His Ile Met Leu Asp Val Ala Phe Thr Ser His Glu His Phe Gly
1               5                   10                  15

<210> SEQ ID NO 78
<211> LENGTH: 15
<212> TYPE: PRT
<213> ORGANISM: Human cytomegalovirus

<400> SEQUENCE: 78

Asp Val Ala Phe Thr Ser His Glu His Phe Gly Leu Leu Cys Pro
1               5                   10                  15

<210> SEQ ID NO 79
<211> LENGTH: 15
<212> TYPE: PRT
<213> ORGANISM: Human cytomegalovirus
```

```
<400> SEQUENCE: 79

Thr Ser His Glu His Phe Gly Leu Leu Cys Pro Lys Ser Ile Pro
1               5                   10                  15

<210> SEQ ID NO 80
<211> LENGTH: 15
<212> TYPE: PRT
<213> ORGANISM: Human cytomegalovirus

<400> SEQUENCE: 80

His Phe Gly Leu Leu Cys Pro Lys Ser Ile Pro Gly Leu Ser Ile
1               5                   10                  15

<210> SEQ ID NO 81
<211> LENGTH: 15
<212> TYPE: PRT
<213> ORGANISM: Human cytomegalovirus

<400> SEQUENCE: 81

Leu Cys Pro Lys Ser Ile Pro Gly Leu Ser Ile Ser Gly Asn Leu
1               5                   10                  15

<210> SEQ ID NO 82
<211> LENGTH: 15
<212> TYPE: PRT
<213> ORGANISM: Human cytomegalovirus

<400> SEQUENCE: 82

Ser Ile Pro Gly Leu Ser Ile Ser Gly Asn Leu Leu Met Asn Gly
1               5                   10                  15

<210> SEQ ID NO 83
<211> LENGTH: 15
<212> TYPE: PRT
<213> ORGANISM: Human cytomegalovirus

<400> SEQUENCE: 83

Leu Ser Ile Ser Gly Asn Leu Leu Met Asn Gly Gln Gln Ile Phe
1               5                   10                  15

<210> SEQ ID NO 84
<211> LENGTH: 15
<212> TYPE: PRT
<213> ORGANISM: Human cytomegalovirus

<400> SEQUENCE: 84

Gly Asn Leu Leu Met Asn Gly Gln Gln Ile Phe Leu Glu Val Gln
1               5                   10                  15

<210> SEQ ID NO 85
<211> LENGTH: 15
<212> TYPE: PRT
<213> ORGANISM: Human cytomegalovirus

<400> SEQUENCE: 85

Met Asn Gly Gln Gln Ile Phe Leu Glu Val Gln Ala Ile Arg Glu
1               5                   10                  15

<210> SEQ ID NO 86
<211> LENGTH: 15
<212> TYPE: PRT
<213> ORGANISM: Human cytomegalovirus

<400> SEQUENCE: 86
```

-continued

```
Gln Ile Phe Leu Glu Val Gln Ala Ile Arg Glu Thr Val Glu Leu
1               5                   10                  15

<210> SEQ ID NO 87
<211> LENGTH: 15
<212> TYPE: PRT
<213> ORGANISM: Human cytomegalovirus

<400> SEQUENCE: 87

Glu Val Gln Ala Ile Arg Glu Thr Val Glu Leu Arg Gln Tyr Asp
1               5                   10                  15

<210> SEQ ID NO 88
<211> LENGTH: 15
<212> TYPE: PRT
<213> ORGANISM: Human cytomegalovirus

<400> SEQUENCE: 88

Ile Arg Glu Thr Val Glu Leu Arg Gln Tyr Asp Pro Val Ala Ala
1               5                   10                  15

<210> SEQ ID NO 89
<211> LENGTH: 15
<212> TYPE: PRT
<213> ORGANISM: Human cytomegalovirus

<400> SEQUENCE: 89

Val Glu Leu Arg Gln Tyr Asp Pro Val Ala Ala Leu Phe Phe Phe
1               5                   10                  15

<210> SEQ ID NO 90
<211> LENGTH: 15
<212> TYPE: PRT
<213> ORGANISM: Human cytomegalovirus

<400> SEQUENCE: 90

Gln Tyr Asp Pro Val Ala Ala Leu Phe Phe Phe Asp Ile Asp Leu
1               5                   10                  15

<210> SEQ ID NO 91
<211> LENGTH: 15
<212> TYPE: PRT
<213> ORGANISM: Human cytomegalovirus

<400> SEQUENCE: 91

Val Ala Ala Leu Phe Phe Phe Asp Ile Asp Leu Leu Leu Gln Arg
1               5                   10                  15

<210> SEQ ID NO 92
<211> LENGTH: 15
<212> TYPE: PRT
<213> ORGANISM: Human cytomegalovirus

<400> SEQUENCE: 92

Phe Phe Phe Asp Ile Asp Leu Leu Leu Gln Arg Gly Pro Gln Tyr
1               5                   10                  15

<210> SEQ ID NO 93
<211> LENGTH: 15
<212> TYPE: PRT
<213> ORGANISM: Human cytomegalovirus

<400> SEQUENCE: 93

Ile Asp Leu Leu Leu Gln Arg Gly Pro Gln Tyr Ser Glu His Pro
```

<210> SEQ ID NO 94
<211> LENGTH: 15
<212> TYPE: PRT
<213> ORGANISM: Human cytomegalovirus

<400> SEQUENCE: 94

Leu Gln Arg Gly Pro Gln Tyr Ser Glu His Pro Thr Phe Thr Ser
1               5                   10                  15

<210> SEQ ID NO 95
<211> LENGTH: 15
<212> TYPE: PRT
<213> ORGANISM: Human cytomegalovirus

<400> SEQUENCE: 95

Pro Gln Tyr Ser Glu His Pro Thr Phe Thr Ser Gln Tyr Arg Ile
1               5                   10                  15

<210> SEQ ID NO 96
<211> LENGTH: 15
<212> TYPE: PRT
<213> ORGANISM: Human cytomegalovirus

<400> SEQUENCE: 96

Glu His Pro Thr Phe Thr Ser Gln Tyr Arg Ile Gln Gly Lys Leu
1               5                   10                  15

<210> SEQ ID NO 97
<211> LENGTH: 15
<212> TYPE: PRT
<213> ORGANISM: Human cytomegalovirus

<400> SEQUENCE: 97

Phe Thr Ser Gln Tyr Arg Ile Gln Gly Lys Leu Glu Tyr Arg His
1               5                   10                  15

<210> SEQ ID NO 98
<211> LENGTH: 15
<212> TYPE: PRT
<213> ORGANISM: Human cytomegalovirus

<400> SEQUENCE: 98

Tyr Arg Ile Gln Gly Lys Leu Glu Tyr Arg His Thr Trp Asp Arg
1               5                   10                  15

<210> SEQ ID NO 99
<211> LENGTH: 15
<212> TYPE: PRT
<213> ORGANISM: Human cytomegalovirus

<400> SEQUENCE: 99

Gly Lys Leu Glu Tyr Arg His Thr Trp Asp Arg His Asp Glu Gly
1               5                   10                  15

<210> SEQ ID NO 100
<211> LENGTH: 15
<212> TYPE: PRT
<213> ORGANISM: Human cytomegalovirus

<400> SEQUENCE: 100

Tyr Arg His Thr Trp Asp Arg His Asp Glu Gly Ala Ala Gln Gly
1               5                   10                  15

-continued

<210> SEQ ID NO 101
<211> LENGTH: 15
<212> TYPE: PRT
<213> ORGANISM: Human cytomegalovirus

<400> SEQUENCE: 101

Trp Asp Arg His Asp Glu Gly Ala Ala Gln Gly Asp Asp Asp Val
1               5                   10                  15

<210> SEQ ID NO 102
<211> LENGTH: 15
<212> TYPE: PRT
<213> ORGANISM: Human cytomegalovirus

<400> SEQUENCE: 102

Asp Glu Gly Ala Ala Gln Gly Asp Asp Asp Val Trp Thr Ser Gly
1               5                   10                  15

<210> SEQ ID NO 103
<211> LENGTH: 15
<212> TYPE: PRT
<213> ORGANISM: Human cytomegalovirus

<400> SEQUENCE: 103

Ala Gln Gly Asp Asp Asp Val Trp Thr Ser Gly Ser Asp Ser Asp
1               5                   10                  15

<210> SEQ ID NO 104
<211> LENGTH: 15
<212> TYPE: PRT
<213> ORGANISM: Human cytomegalovirus

<400> SEQUENCE: 104

Asp Asp Val Trp Thr Ser Gly Ser Asp Ser Asp Glu Glu Leu Val
1               5                   10                  15

<210> SEQ ID NO 105
<211> LENGTH: 15
<212> TYPE: PRT
<213> ORGANISM: Human cytomegalovirus

<400> SEQUENCE: 105

Thr Ser Gly Ser Asp Ser Asp Glu Glu Leu Val Thr Thr Glu Arg
1               5                   10                  15

<210> SEQ ID NO 106
<211> LENGTH: 15
<212> TYPE: PRT
<213> ORGANISM: Human cytomegalovirus

<400> SEQUENCE: 106

Asp Ser Asp Glu Glu Leu Val Thr Thr Glu Arg Lys Thr Pro Arg
1               5                   10                  15

<210> SEQ ID NO 107
<211> LENGTH: 15
<212> TYPE: PRT
<213> ORGANISM: Human cytomegalovirus

<400> SEQUENCE: 107

Glu Leu Val Thr Thr Glu Arg Lys Thr Pro Arg Val Thr Gly Gly
1               5                   10                  15

<210> SEQ ID NO 108

```
<211> LENGTH: 15
<212> TYPE: PRT
<213> ORGANISM: Human cytomegalovirus

<400> SEQUENCE: 108

Thr Glu Arg Lys Thr Pro Arg Val Thr Gly Gly Gly Ala Met Ala
1               5                   10                  15

<210> SEQ ID NO 109
<211> LENGTH: 15
<212> TYPE: PRT
<213> ORGANISM: Human cytomegalovirus

<400> SEQUENCE: 109

Thr Pro Arg Val Thr Gly Gly Gly Ala Met Ala Gly Ala Ser Thr
1               5                   10                  15

<210> SEQ ID NO 110
<211> LENGTH: 15
<212> TYPE: PRT
<213> ORGANISM: Human cytomegalovirus

<400> SEQUENCE: 110

Thr Gly Gly Gly Ala Met Ala Gly Ala Ser Thr Ser Ala Gly Arg
1               5                   10                  15

<210> SEQ ID NO 111
<211> LENGTH: 15
<212> TYPE: PRT
<213> ORGANISM: Human cytomegalovirus

<400> SEQUENCE: 111

Ala Met Ala Gly Ala Ser Thr Ser Ala Gly Arg Lys Arg Lys Ser
1               5                   10                  15

<210> SEQ ID NO 112
<211> LENGTH: 15
<212> TYPE: PRT
<213> ORGANISM: Human cytomegalovirus

<400> SEQUENCE: 112

Ala Ser Thr Ser Ala Gly Arg Lys Arg Lys Ser Ala Ser Ser Ala
1               5                   10                  15

<210> SEQ ID NO 113
<211> LENGTH: 15
<212> TYPE: PRT
<213> ORGANISM: Human cytomegalovirus

<400> SEQUENCE: 113

Ala Gly Arg Lys Arg Lys Ser Ala Ser Ser Ala Thr Ala Cys Thr
1               5                   10                  15

<210> SEQ ID NO 114
<211> LENGTH: 15
<212> TYPE: PRT
<213> ORGANISM: Human cytomegalovirus

<400> SEQUENCE: 114

Arg Lys Ser Ala Ser Ser Ala Thr Ala Cys Thr Ser Gly Val Met
1               5                   10                  15

<210> SEQ ID NO 115
<211> LENGTH: 15
<212> TYPE: PRT
```

<213> ORGANISM: Human cytomegalovirus

<400> SEQUENCE: 115

Ser Ser Ala Thr Ala Cys Thr Ser Gly Val Met Thr Arg Gly Arg
1               5                   10                  15

<210> SEQ ID NO 116
<211> LENGTH: 15
<212> TYPE: PRT
<213> ORGANISM: Human cytomegalovirus

<400> SEQUENCE: 116

Ala Cys Thr Ser Gly Val Met Thr Arg Gly Arg Leu Lys Ala Glu
1               5                   10                  15

<210> SEQ ID NO 117
<211> LENGTH: 15
<212> TYPE: PRT
<213> ORGANISM: Human cytomegalovirus

<400> SEQUENCE: 117

Gly Val Met Thr Arg Gly Arg Leu Lys Ala Glu Ser Thr Val Ala
1               5                   10                  15

<210> SEQ ID NO 118
<211> LENGTH: 15
<212> TYPE: PRT
<213> ORGANISM: Human cytomegalovirus

<400> SEQUENCE: 118

Arg Gly Arg Leu Lys Ala Glu Ser Thr Val Ala Pro Glu Glu Asp
1               5                   10                  15

<210> SEQ ID NO 119
<211> LENGTH: 15
<212> TYPE: PRT
<213> ORGANISM: Human cytomegalovirus

<400> SEQUENCE: 119

Lys Ala Glu Ser Thr Val Ala Pro Glu Glu Asp Thr Asp Glu Asp
1               5                   10                  15

<210> SEQ ID NO 120
<211> LENGTH: 15
<212> TYPE: PRT
<213> ORGANISM: Human cytomegalovirus

<400> SEQUENCE: 120

Thr Val Ala Pro Glu Glu Asp Thr Asp Glu Asp Ser Asp Asn Glu
1               5                   10                  15

<210> SEQ ID NO 121
<211> LENGTH: 15
<212> TYPE: PRT
<213> ORGANISM: Human cytomegalovirus

<400> SEQUENCE: 121

Glu Glu Asp Thr Asp Glu Asp Ser Asp Asn Glu Ile His Asn Pro
1               5                   10                  15

<210> SEQ ID NO 122
<211> LENGTH: 15
<212> TYPE: PRT
<213> ORGANISM: Human cytomegalovirus

<400> SEQUENCE: 122

Asp Glu Asp Ser Asp Asn Glu Ile His Asn Pro Ala Val Phe Thr
1               5                   10                  15

<210> SEQ ID NO 123
<211> LENGTH: 15
<212> TYPE: PRT
<213> ORGANISM: Human cytomegalovirus

<400> SEQUENCE: 123

Asp Asn Glu Ile His Asn Pro Ala Val Phe Thr Trp Pro Pro Trp
1               5                   10                  15

<210> SEQ ID NO 124
<211> LENGTH: 15
<212> TYPE: PRT
<213> ORGANISM: Human cytomegalovirus

<400> SEQUENCE: 124

His Asn Pro Ala Val Phe Thr Trp Pro Pro Trp Gln Ala Gly Ile
1               5                   10                  15

<210> SEQ ID NO 125
<211> LENGTH: 15
<212> TYPE: PRT
<213> ORGANISM: Human cytomegalovirus

<400> SEQUENCE: 125

Val Phe Thr Trp Pro Pro Trp Gln Ala Gly Ile Leu Ala Arg Asn
1               5                   10                  15

<210> SEQ ID NO 126
<211> LENGTH: 15
<212> TYPE: PRT
<213> ORGANISM: Human cytomegalovirus

<400> SEQUENCE: 126

Pro Pro Trp Gln Ala Gly Ile Leu Ala Arg Asn Leu Val Pro Met
1               5                   10                  15

<210> SEQ ID NO 127
<211> LENGTH: 15
<212> TYPE: PRT
<213> ORGANISM: Human cytomegalovirus

<400> SEQUENCE: 127

Ala Gly Ile Leu Ala Arg Asn Leu Val Pro Met Val Ala Thr Val
1               5                   10                  15

<210> SEQ ID NO 128
<211> LENGTH: 15
<212> TYPE: PRT
<213> ORGANISM: Human cytomegalovirus

<400> SEQUENCE: 128

Ala Arg Asn Leu Val Pro Met Val Ala Thr Val Gln Gly Gln Asn
1               5                   10                  15

<210> SEQ ID NO 129
<211> LENGTH: 15
<212> TYPE: PRT
<213> ORGANISM: Human cytomegalovirus

<400> SEQUENCE: 129

```
Val Pro Met Val Ala Thr Val Gln Gly Gln Asn Leu Lys Tyr Gln
1               5                   10                  15
```

<210> SEQ ID NO 130
<211> LENGTH: 15
<212> TYPE: PRT
<213> ORGANISM: Human cytomegalovirus

<400> SEQUENCE: 130

```
Ala Thr Val Gln Gly Gln Asn Leu Lys Tyr Gln Glu Phe Phe Trp
1               5                   10                  15
```

<210> SEQ ID NO 131
<211> LENGTH: 15
<212> TYPE: PRT
<213> ORGANISM: Human cytomegalovirus

<400> SEQUENCE: 131

```
Gly Gln Asn Leu Lys Tyr Gln Glu Phe Phe Trp Asp Ala Asn Asp
1               5                   10                  15
```

<210> SEQ ID NO 132
<211> LENGTH: 15
<212> TYPE: PRT
<213> ORGANISM: Human cytomegalovirus

<400> SEQUENCE: 132

```
Lys Tyr Gln Glu Phe Phe Trp Asp Ala Asn Asp Ile Tyr Arg Ile
1               5                   10                  15
```

<210> SEQ ID NO 133
<211> LENGTH: 15
<212> TYPE: PRT
<213> ORGANISM: Human cytomegalovirus

<400> SEQUENCE: 133

```
Phe Phe Trp Asp Ala Asn Asp Ile Tyr Arg Ile Phe Ala Glu Leu
1               5                   10                  15
```

<210> SEQ ID NO 134
<211> LENGTH: 15
<212> TYPE: PRT
<213> ORGANISM: Human cytomegalovirus

<400> SEQUENCE: 134

```
Ala Asn Asp Ile Tyr Arg Ile Phe Ala Glu Leu Glu Gly Val Trp
1               5                   10                  15
```

<210> SEQ ID NO 135
<211> LENGTH: 15
<212> TYPE: PRT
<213> ORGANISM: Human cytomegalovirus

<400> SEQUENCE: 135

```
Tyr Arg Ile Phe Ala Glu Leu Glu Gly Val Trp Gln Pro Ala Ala
1               5                   10                  15
```

<210> SEQ ID NO 136
<211> LENGTH: 15
<212> TYPE: PRT
<213> ORGANISM: Human cytomegalovirus

<400> SEQUENCE: 136

```
Ala Glu Leu Glu Gly Val Trp Gln Pro Ala Ala Gln Pro Lys Arg
1               5                   10                  15
```

<210> SEQ ID NO 137
<211> LENGTH: 15
<212> TYPE: PRT
<213> ORGANISM: Human cytomegalovirus

<400> SEQUENCE: 137

Gly Val Trp Gln Pro Ala Ala Gln Pro Lys Arg Arg Arg His Arg
1               5                   10                  15

<210> SEQ ID NO 138
<211> LENGTH: 15
<212> TYPE: PRT
<213> ORGANISM: Human cytomegalovirus

<400> SEQUENCE: 138

Pro Ala Ala Gln Pro Lys Arg Arg Arg His Arg Gln Asp Ala Leu
1               5                   10                  15

<210> SEQ ID NO 139
<211> LENGTH: 15
<212> TYPE: PRT
<213> ORGANISM: Human cytomegalovirus

<400> SEQUENCE: 139

Pro Lys Arg Arg Arg His Arg Gln Asp Ala Leu Pro Gly Pro Cys
1               5                   10                  15

<210> SEQ ID NO 140
<211> LENGTH: 15
<212> TYPE: PRT
<213> ORGANISM: Human cytomegalovirus

<400> SEQUENCE: 140

Arg His Arg Gln Asp Ala Leu Pro Gly Pro Cys Ile Ala Ser Thr
1               5                   10                  15

<210> SEQ ID NO 141
<211> LENGTH: 15
<212> TYPE: PRT
<213> ORGANISM: Human cytomegalovirus

<400> SEQUENCE: 141

Asp Ala Leu Pro Gly Pro Cys Ile Ala Ser Thr Pro Lys Lys His
1               5                   10                  15

<210> SEQ ID NO 142
<211> LENGTH: 13
<212> TYPE: PRT
<213> ORGANISM: Human cytomegalovirus

<400> SEQUENCE: 142

Gly Pro Cys Ile Ala Ser Thr Pro Lys Lys His Arg Gly
1               5                   10

<210> SEQ ID NO 143
<211> LENGTH: 15
<212> TYPE: PRT
<213> ORGANISM: Human cytomegalovirus

<400> SEQUENCE: 143

Met Glu Ser Ser Ala Lys Arg Lys Met Asp Pro Asp Asn Pro Asp
1               5                   10                  15

```
<210> SEQ ID NO 144
<211> LENGTH: 15
<212> TYPE: PRT
<213> ORGANISM: Human cytomegalovirus

<400> SEQUENCE: 144

Ala Lys Arg Lys Met Asp Pro Asp Asn Pro Asp Glu Gly Pro Ser
1               5                   10                  15

<210> SEQ ID NO 145
<211> LENGTH: 15
<212> TYPE: PRT
<213> ORGANISM: Human cytomegalovirus

<400> SEQUENCE: 145

Met Asp Pro Asp Asn Pro Asp Glu Gly Pro Ser Ser Lys Val Pro
1               5                   10                  15

<210> SEQ ID NO 146
<211> LENGTH: 15
<212> TYPE: PRT
<213> ORGANISM: Human cytomegalovirus

<400> SEQUENCE: 146

Asn Pro Asp Glu Gly Pro Ser Ser Lys Val Pro Arg Pro Glu Thr
1               5                   10                  15

<210> SEQ ID NO 147
<211> LENGTH: 15
<212> TYPE: PRT
<213> ORGANISM: Human cytomegalovirus

<400> SEQUENCE: 147

Gly Pro Ser Ser Lys Val Pro Arg Pro Glu Thr Pro Val Thr Lys
1               5                   10                  15

<210> SEQ ID NO 148
<211> LENGTH: 15
<212> TYPE: PRT
<213> ORGANISM: Human cytomegalovirus

<400> SEQUENCE: 148

Lys Val Pro Arg Pro Glu Thr Pro Val Thr Lys Ala Thr Thr Phe
1               5                   10                  15

<210> SEQ ID NO 149
<211> LENGTH: 15
<212> TYPE: PRT
<213> ORGANISM: Human cytomegalovirus

<400> SEQUENCE: 149

Pro Glu Thr Pro Val Thr Lys Ala Thr Thr Phe Leu Gln Thr Met
1               5                   10                  15

<210> SEQ ID NO 150
<211> LENGTH: 15
<212> TYPE: PRT
<213> ORGANISM: Human cytomegalovirus

<400> SEQUENCE: 150

Val Thr Lys Ala Thr Thr Phe Leu Gln Thr Met Leu Arg Lys Glu
1               5                   10                  15

<210> SEQ ID NO 151
<211> LENGTH: 15
```

<212> TYPE: PRT
<213> ORGANISM: Human cytomegalovirus

<400> SEQUENCE: 151

Thr Thr Phe Leu Gln Thr Met Leu Arg Lys Glu Val Asn Ser Gln
1               5                   10                  15

<210> SEQ ID NO 152
<211> LENGTH: 15
<212> TYPE: PRT
<213> ORGANISM: Human cytomegalovirus

<400> SEQUENCE: 152

Gln Thr Met Leu Arg Lys Glu Val Asn Ser Gln Leu Ser Leu Gly
1               5                   10                  15

<210> SEQ ID NO 153
<211> LENGTH: 15
<212> TYPE: PRT
<213> ORGANISM: Human cytomegalovirus

<400> SEQUENCE: 153

Arg Lys Glu Val Asn Ser Gln Leu Ser Leu Gly Asp Pro Leu Phe
1               5                   10                  15

<210> SEQ ID NO 154
<211> LENGTH: 15
<212> TYPE: PRT
<213> ORGANISM: Human cytomegalovirus

<400> SEQUENCE: 154

Asn Ser Gln Leu Ser Leu Gly Asp Pro Leu Phe Pro Glu Leu Ala
1               5                   10                  15

<210> SEQ ID NO 155
<211> LENGTH: 15
<212> TYPE: PRT
<213> ORGANISM: Human cytomegalovirus

<400> SEQUENCE: 155

Ser Leu Gly Asp Pro Leu Phe Pro Glu Leu Ala Glu Glu Ser Leu
1               5                   10                  15

<210> SEQ ID NO 156
<211> LENGTH: 15
<212> TYPE: PRT
<213> ORGANISM: Human cytomegalovirus

<400> SEQUENCE: 156

Pro Leu Phe Pro Glu Leu Ala Glu Glu Ser Leu Lys Thr Phe Glu
1               5                   10                  15

<210> SEQ ID NO 157
<211> LENGTH: 15
<212> TYPE: PRT
<213> ORGANISM: Human cytomegalovirus

<400> SEQUENCE: 157

Glu Leu Ala Glu Glu Ser Leu Lys Thr Phe Glu Gln Val Thr Glu
1               5                   10                  15

<210> SEQ ID NO 158
<211> LENGTH: 15
<212> TYPE: PRT
<213> ORGANISM: Human cytomegalovirus

```
<400> SEQUENCE: 158

Glu Ser Leu Lys Thr Phe Glu Gln Val Thr Glu Asp Cys Asn Glu
1               5                   10                  15

<210> SEQ ID NO 159
<211> LENGTH: 15
<212> TYPE: PRT
<213> ORGANISM: Human cytomegalovirus

<400> SEQUENCE: 159

Thr Phe Glu Gln Val Thr Glu Asp Cys Asn Glu Asn Pro Glu Lys
1               5                   10                  15

<210> SEQ ID NO 160
<211> LENGTH: 15
<212> TYPE: PRT
<213> ORGANISM: Human cytomegalovirus

<400> SEQUENCE: 160

Val Thr Glu Asp Cys Asn Glu Asn Pro Glu Lys Asp Val Leu Ala
1               5                   10                  15

<210> SEQ ID NO 161
<211> LENGTH: 15
<212> TYPE: PRT
<213> ORGANISM: Human cytomegalovirus

<400> SEQUENCE: 161

Cys Asn Glu Asn Pro Glu Lys Asp Val Leu Ala Glu Leu Val Lys
1               5                   10                  15

<210> SEQ ID NO 162
<211> LENGTH: 15
<212> TYPE: PRT
<213> ORGANISM: Human cytomegalovirus

<400> SEQUENCE: 162

Pro Glu Lys Asp Val Leu Ala Glu Leu Val Lys Gln Ile Lys Val
1               5                   10                  15

<210> SEQ ID NO 163
<211> LENGTH: 15
<212> TYPE: PRT
<213> ORGANISM: Human cytomegalovirus

<400> SEQUENCE: 163

Val Leu Ala Glu Leu Val Lys Gln Ile Lys Val Arg Val Asp Met
1               5                   10                  15

<210> SEQ ID NO 164
<211> LENGTH: 15
<212> TYPE: PRT
<213> ORGANISM: Human cytomegalovirus

<400> SEQUENCE: 164

Leu Val Lys Gln Ile Lys Val Arg Val Asp Met Val Arg His Arg
1               5                   10                  15

<210> SEQ ID NO 165
<211> LENGTH: 15
<212> TYPE: PRT
<213> ORGANISM: Human cytomegalovirus

<400> SEQUENCE: 165
```

Ile Lys Val Arg Val Asp Met Val Arg His Arg Ile Lys Glu His
1               5                   10                  15

<210> SEQ ID NO 166
<211> LENGTH: 15
<212> TYPE: PRT
<213> ORGANISM: Human cytomegalovirus

<400> SEQUENCE: 166

Val Asp Met Val Arg His Arg Ile Lys Glu His Met Leu Lys Lys
1               5                   10                  15

<210> SEQ ID NO 167
<211> LENGTH: 15
<212> TYPE: PRT
<213> ORGANISM: Human cytomegalovirus

<400> SEQUENCE: 167

Arg His Arg Ile Lys Glu His Met Leu Lys Lys Tyr Thr Gln Thr
1               5                   10                  15

<210> SEQ ID NO 168
<211> LENGTH: 15
<212> TYPE: PRT
<213> ORGANISM: Human cytomegalovirus

<400> SEQUENCE: 168

Lys Glu His Met Leu Lys Lys Tyr Thr Gln Thr Glu Glu Lys Phe
1               5                   10                  15

<210> SEQ ID NO 169
<211> LENGTH: 15
<212> TYPE: PRT
<213> ORGANISM: Human cytomegalovirus

<400> SEQUENCE: 169

Leu Lys Lys Tyr Thr Gln Thr Glu Glu Lys Phe Thr Gly Ala Phe
1               5                   10                  15

<210> SEQ ID NO 170
<211> LENGTH: 15
<212> TYPE: PRT
<213> ORGANISM: Human cytomegalovirus

<400> SEQUENCE: 170

Thr Gln Thr Glu Glu Lys Phe Thr Gly Ala Phe Asn Met Met Gly
1               5                   10                  15

<210> SEQ ID NO 171
<211> LENGTH: 15
<212> TYPE: PRT
<213> ORGANISM: Human cytomegalovirus

<400> SEQUENCE: 171

Glu Lys Phe Thr Gly Ala Phe Asn Met Met Gly Gly Cys Leu Gln
1               5                   10                  15

<210> SEQ ID NO 172
<211> LENGTH: 15
<212> TYPE: PRT
<213> ORGANISM: Human cytomegalovirus

<400> SEQUENCE: 172

Gly Ala Phe Asn Met Met Gly Gly Cys Leu Gln Asn Ala Leu Asp

```
1               5                   10                  15
```

<210> SEQ ID NO 173
<211> LENGTH: 15
<212> TYPE: PRT
<213> ORGANISM: Human cytomegalovirus

<400> SEQUENCE: 173

```
Met Met Gly Gly Cys Leu Gln Asn Ala Leu Asp Ile Leu Asp Lys
1               5                   10                  15
```

<210> SEQ ID NO 174
<211> LENGTH: 15
<212> TYPE: PRT
<213> ORGANISM: Human cytomegalovirus

<400> SEQUENCE: 174

```
Cys Leu Gln Asn Ala Leu Asp Ile Leu Asp Lys Val His Glu Pro
1               5                   10                  15
```

<210> SEQ ID NO 175
<211> LENGTH: 15
<212> TYPE: PRT
<213> ORGANISM: Human cytomegalovirus

<400> SEQUENCE: 175

```
Ala Leu Asp Ile Leu Asp Lys Val His Glu Pro Phe Glu Glu Met
1               5                   10                  15
```

<210> SEQ ID NO 176
<211> LENGTH: 15
<212> TYPE: PRT
<213> ORGANISM: Human cytomegalovirus

<400> SEQUENCE: 176

```
Leu Asp Lys Val His Glu Pro Phe Glu Glu Met Lys Cys Ile Gly
1               5                   10                  15
```

<210> SEQ ID NO 177
<211> LENGTH: 15
<212> TYPE: PRT
<213> ORGANISM: Human cytomegalovirus

<400> SEQUENCE: 177

```
His Glu Pro Phe Glu Glu Met Lys Cys Ile Gly Leu Thr Met Gln
1               5                   10                  15
```

<210> SEQ ID NO 178
<211> LENGTH: 15
<212> TYPE: PRT
<213> ORGANISM: Human cytomegalovirus

<400> SEQUENCE: 178

```
Glu Glu Met Lys Cys Ile Gly Leu Thr Met Gln Ser Met Tyr Glu
1               5                   10                  15
```

<210> SEQ ID NO 179
<211> LENGTH: 15
<212> TYPE: PRT
<213> ORGANISM: Human cytomegalovirus

<400> SEQUENCE: 179

```
Cys Ile Gly Leu Thr Met Gln Ser Met Tyr Glu Asn Tyr Ile Val
1               5                   10                  15
```

```
<210> SEQ ID NO 180
<211> LENGTH: 15
<212> TYPE: PRT
<213> ORGANISM: Human cytomegalovirus

<400> SEQUENCE: 180

Thr Met Gln Ser Met Tyr Glu Asn Tyr Ile Val Pro Glu Asp Lys
1               5                   10                  15

<210> SEQ ID NO 181
<211> LENGTH: 15
<212> TYPE: PRT
<213> ORGANISM: Human cytomegalovirus

<400> SEQUENCE: 181

Met Tyr Glu Asn Tyr Ile Val Pro Glu Asp Lys Arg Glu Met Trp
1               5                   10                  15

<210> SEQ ID NO 182
<211> LENGTH: 15
<212> TYPE: PRT
<213> ORGANISM: Human cytomegalovirus

<400> SEQUENCE: 182

Tyr Ile Val Pro Glu Asp Lys Arg Glu Met Trp Met Ala Cys Ile
1               5                   10                  15

<210> SEQ ID NO 183
<211> LENGTH: 15
<212> TYPE: PRT
<213> ORGANISM: Human cytomegalovirus

<400> SEQUENCE: 183

Glu Asp Lys Arg Glu Met Trp Met Ala Cys Ile Lys Glu Leu His
1               5                   10                  15

<210> SEQ ID NO 184
<211> LENGTH: 15
<212> TYPE: PRT
<213> ORGANISM: Human cytomegalovirus

<400> SEQUENCE: 184

Glu Met Trp Met Ala Cys Ile Lys Glu Leu His Asp Val Ser Lys
1               5                   10                  15

<210> SEQ ID NO 185
<211> LENGTH: 15
<212> TYPE: PRT
<213> ORGANISM: Human cytomegalovirus

<400> SEQUENCE: 185

Ala Cys Ile Lys Glu Leu His Asp Val Ser Lys Gly Ala Ala Asn
1               5                   10                  15

<210> SEQ ID NO 186
<211> LENGTH: 15
<212> TYPE: PRT
<213> ORGANISM: Human cytomegalovirus

<400> SEQUENCE: 186

Glu Leu His Asp Val Ser Lys Gly Ala Ala Asn Lys Leu Gly Gly
1               5                   10                  15

<210> SEQ ID NO 187
```

```
<211> LENGTH: 15
<212> TYPE: PRT
<213> ORGANISM: Human cytomegalovirus

<400> SEQUENCE: 187

Val Ser Lys Gly Ala Ala Asn Lys Leu Gly Gly Ala Leu Gln Ala
1               5                   10                  15

<210> SEQ ID NO 188
<211> LENGTH: 15
<212> TYPE: PRT
<213> ORGANISM: Human cytomegalovirus

<400> SEQUENCE: 188

Ala Ala Asn Lys Leu Gly Gly Ala Leu Gln Ala Lys Ala Arg Ala
1               5                   10                  15

<210> SEQ ID NO 189
<211> LENGTH: 15
<212> TYPE: PRT
<213> ORGANISM: Human cytomegalovirus

<400> SEQUENCE: 189

Leu Gly Gly Ala Leu Gln Ala Lys Ala Arg Ala Lys Lys Asp Glu
1               5                   10                  15

<210> SEQ ID NO 190
<211> LENGTH: 15
<212> TYPE: PRT
<213> ORGANISM: Human cytomegalovirus

<400> SEQUENCE: 190

Leu Gln Ala Lys Ala Arg Ala Lys Lys Asp Glu Leu Arg Arg Lys
1               5                   10                  15

<210> SEQ ID NO 191
<211> LENGTH: 15
<212> TYPE: PRT
<213> ORGANISM: Human cytomegalovirus

<400> SEQUENCE: 191

Ala Arg Ala Lys Lys Asp Glu Leu Arg Arg Lys Met Met Tyr Met
1               5                   10                  15

<210> SEQ ID NO 192
<211> LENGTH: 15
<212> TYPE: PRT
<213> ORGANISM: Human cytomegalovirus

<400> SEQUENCE: 192

Lys Asp Glu Leu Arg Arg Lys Met Met Tyr Met Cys Tyr Arg Asn
1               5                   10                  15

<210> SEQ ID NO 193
<211> LENGTH: 15
<212> TYPE: PRT
<213> ORGANISM: Human cytomegalovirus

<400> SEQUENCE: 193

Arg Arg Lys Met Met Tyr Met Cys Tyr Arg Asn Ile Glu Phe Phe
1               5                   10                  15

<210> SEQ ID NO 194
<211> LENGTH: 15
<212> TYPE: PRT
```

<213> ORGANISM: Human cytomegalovirus

<400> SEQUENCE: 194

Met Tyr Met Cys Tyr Arg Asn Ile Glu Phe Phe Thr Lys Asn Ser
1               5                   10                  15

<210> SEQ ID NO 195
<211> LENGTH: 15
<212> TYPE: PRT
<213> ORGANISM: Human cytomegalovirus

<400> SEQUENCE: 195

Tyr Arg Asn Ile Glu Phe Phe Thr Lys Asn Ser Ala Phe Pro Lys
1               5                   10                  15

<210> SEQ ID NO 196
<211> LENGTH: 15
<212> TYPE: PRT
<213> ORGANISM: Human cytomegalovirus

<400> SEQUENCE: 196

Glu Phe Phe Thr Lys Asn Ser Ala Phe Pro Lys Thr Thr Asn Gly
1               5                   10                  15

<210> SEQ ID NO 197
<211> LENGTH: 15
<212> TYPE: PRT
<213> ORGANISM: Human cytomegalovirus

<400> SEQUENCE: 197

Lys Asn Ser Ala Phe Pro Lys Thr Thr Asn Gly Cys Ser Gln Ala
1               5                   10                  15

<210> SEQ ID NO 198
<211> LENGTH: 15
<212> TYPE: PRT
<213> ORGANISM: Human cytomegalovirus

<400> SEQUENCE: 198

Phe Pro Lys Thr Thr Asn Gly Cys Ser Gln Ala Met Ala Ala Leu
1               5                   10                  15

<210> SEQ ID NO 199
<211> LENGTH: 15
<212> TYPE: PRT
<213> ORGANISM: Human cytomegalovirus

<400> SEQUENCE: 199

Thr Asn Gly Cys Ser Gln Ala Met Ala Ala Leu Gln Asn Leu Pro
1               5                   10                  15

<210> SEQ ID NO 200
<211> LENGTH: 15
<212> TYPE: PRT
<213> ORGANISM: Human cytomegalovirus

<400> SEQUENCE: 200

Ser Gln Ala Met Ala Ala Leu Gln Asn Leu Pro Gln Cys Ser Pro
1               5                   10                  15

<210> SEQ ID NO 201
<211> LENGTH: 15
<212> TYPE: PRT
<213> ORGANISM: Human cytomegalovirus

```
<400> SEQUENCE: 201

Ala Ala Leu Gln Asn Leu Pro Gln Cys Ser Pro Asp Glu Ile Met
1               5                   10                  15

<210> SEQ ID NO 202
<211> LENGTH: 15
<212> TYPE: PRT
<213> ORGANISM: Human cytomegalovirus

<400> SEQUENCE: 202

Asn Leu Pro Gln Cys Ser Pro Asp Glu Ile Met Ala Tyr Ala Gln
1               5                   10                  15

<210> SEQ ID NO 203
<211> LENGTH: 15
<212> TYPE: PRT
<213> ORGANISM: Human cytomegalovirus

<400> SEQUENCE: 203

Cys Ser Pro Asp Glu Ile Met Ala Tyr Ala Gln Lys Ile Phe Lys
1               5                   10                  15

<210> SEQ ID NO 204
<211> LENGTH: 15
<212> TYPE: PRT
<213> ORGANISM: Human cytomegalovirus

<400> SEQUENCE: 204

Glu Ile Met Ala Tyr Ala Gln Lys Ile Phe Lys Ile Leu Asp Glu
1               5                   10                  15

<210> SEQ ID NO 205
<211> LENGTH: 15
<212> TYPE: PRT
<213> ORGANISM: Human cytomegalovirus

<400> SEQUENCE: 205

Tyr Ala Gln Lys Ile Phe Lys Ile Leu Asp Glu Glu Arg Asp Lys
1               5                   10                  15

<210> SEQ ID NO 206
<211> LENGTH: 15
<212> TYPE: PRT
<213> ORGANISM: Human cytomegalovirus

<400> SEQUENCE: 206

Ile Phe Lys Ile Leu Asp Glu Glu Arg Asp Lys Val Leu Thr His
1               5                   10                  15

<210> SEQ ID NO 207
<211> LENGTH: 15
<212> TYPE: PRT
<213> ORGANISM: Human cytomegalovirus

<400> SEQUENCE: 207

Leu Asp Glu Glu Arg Asp Lys Val Leu Thr His Ile Asp His Ile
1               5                   10                  15

<210> SEQ ID NO 208
<211> LENGTH: 15
<212> TYPE: PRT
<213> ORGANISM: Human cytomegalovirus

<400> SEQUENCE: 208
```

```
Arg Asp Lys Val Leu Thr His Ile Asp His Ile Phe Met Asp Ile
1               5                   10                  15
```

<210> SEQ ID NO 209
<211> LENGTH: 15
<212> TYPE: PRT
<213> ORGANISM: Human cytomegalovirus

<400> SEQUENCE: 209

```
Leu Thr His Ile Asp His Ile Phe Met Asp Ile Leu Thr Thr Cys
1               5                   10                  15
```

<210> SEQ ID NO 210
<211> LENGTH: 15
<212> TYPE: PRT
<213> ORGANISM: Human cytomegalovirus

<400> SEQUENCE: 210

```
Asp His Ile Phe Met Asp Ile Leu Thr Thr Cys Val Glu Thr Met
1               5                   10                  15
```

<210> SEQ ID NO 211
<211> LENGTH: 15
<212> TYPE: PRT
<213> ORGANISM: Human cytomegalovirus

<400> SEQUENCE: 211

```
Met Asp Ile Leu Thr Thr Cys Val Glu Thr Met Cys Asn Glu Tyr
1               5                   10                  15
```

<210> SEQ ID NO 212
<211> LENGTH: 15
<212> TYPE: PRT
<213> ORGANISM: Human cytomegalovirus

<400> SEQUENCE: 212

```
Thr Thr Cys Val Glu Thr Met Cys Asn Glu Tyr Lys Val Thr Ser
1               5                   10                  15
```

<210> SEQ ID NO 213
<211> LENGTH: 15
<212> TYPE: PRT
<213> ORGANISM: Human cytomegalovirus

<400> SEQUENCE: 213

```
Glu Thr Met Cys Asn Glu Tyr Lys Val Thr Ser Asp Ala Cys Met
1               5                   10                  15
```

<210> SEQ ID NO 214
<211> LENGTH: 15
<212> TYPE: PRT
<213> ORGANISM: Human cytomegalovirus

<400> SEQUENCE: 214

```
Asn Glu Tyr Lys Val Thr Ser Asp Ala Cys Met Met Thr Met Tyr
1               5                   10                  15
```

<210> SEQ ID NO 215
<211> LENGTH: 15
<212> TYPE: PRT
<213> ORGANISM: Human cytomegalovirus

<400> SEQUENCE: 215

```
Val Thr Ser Asp Ala Cys Met Met Thr Met Tyr Gly Gly Ile Ser
1               5                   10                  15
```

<210> SEQ ID NO 216
<211> LENGTH: 15
<212> TYPE: PRT
<213> ORGANISM: Human cytomegalovirus

<400> SEQUENCE: 216

Ala Cys Met Met Thr Met Tyr Gly Gly Ile Ser Leu Leu Ser Glu
1               5                   10                  15

<210> SEQ ID NO 217
<211> LENGTH: 15
<212> TYPE: PRT
<213> ORGANISM: Human cytomegalovirus

<400> SEQUENCE: 217

Thr Met Tyr Gly Gly Ile Ser Leu Leu Ser Glu Phe Cys Arg Val
1               5                   10                  15

<210> SEQ ID NO 218
<211> LENGTH: 15
<212> TYPE: PRT
<213> ORGANISM: Human cytomegalovirus

<400> SEQUENCE: 218

Gly Ile Ser Leu Leu Ser Glu Phe Cys Arg Val Leu Cys Cys Tyr
1               5                   10                  15

<210> SEQ ID NO 219
<211> LENGTH: 15
<212> TYPE: PRT
<213> ORGANISM: Human cytomegalovirus

<400> SEQUENCE: 219

Leu Ser Glu Phe Cys Arg Val Leu Cys Cys Tyr Val Leu Glu Glu
1               5                   10                  15

<210> SEQ ID NO 220
<211> LENGTH: 15
<212> TYPE: PRT
<213> ORGANISM: Human cytomegalovirus

<400> SEQUENCE: 220

Cys Arg Val Leu Cys Cys Tyr Val Leu Glu Glu Thr Ser Val Met
1               5                   10                  15

<210> SEQ ID NO 221
<211> LENGTH: 15
<212> TYPE: PRT
<213> ORGANISM: Human cytomegalovirus

<400> SEQUENCE: 221

Cys Cys Tyr Val Leu Glu Glu Thr Ser Val Met Leu Ala Lys Arg
1               5                   10                  15

<210> SEQ ID NO 222
<211> LENGTH: 15
<212> TYPE: PRT
<213> ORGANISM: Human cytomegalovirus

<400> SEQUENCE: 222

Leu Glu Glu Thr Ser Val Met Leu Ala Lys Arg Pro Leu Ile Thr
1               5                   10                  15

```
<210> SEQ ID NO 223
<211> LENGTH: 15
<212> TYPE: PRT
<213> ORGANISM: Human cytomegalovirus

<400> SEQUENCE: 223

Ser Val Met Leu Ala Lys Arg Pro Leu Ile Thr Lys Pro Glu Val
1               5                   10                  15

<210> SEQ ID NO 224
<211> LENGTH: 15
<212> TYPE: PRT
<213> ORGANISM: Human cytomegalovirus

<400> SEQUENCE: 224

Ala Lys Arg Pro Leu Ile Thr Lys Pro Glu Val Ile Ser Val Met
1               5                   10                  15

<210> SEQ ID NO 225
<211> LENGTH: 15
<212> TYPE: PRT
<213> ORGANISM: Human cytomegalovirus

<400> SEQUENCE: 225

Leu Ile Thr Lys Pro Glu Val Ile Ser Val Met Lys Arg Arg Ile
1               5                   10                  15

<210> SEQ ID NO 226
<211> LENGTH: 15
<212> TYPE: PRT
<213> ORGANISM: Human cytomegalovirus

<400> SEQUENCE: 226

Pro Glu Val Ile Ser Val Met Lys Arg Arg Ile Glu Glu Ile Cys
1               5                   10                  15

<210> SEQ ID NO 227
<211> LENGTH: 15
<212> TYPE: PRT
<213> ORGANISM: Human cytomegalovirus

<400> SEQUENCE: 227

Ser Val Met Lys Arg Arg Ile Glu Glu Ile Cys Met Lys Val Phe
1               5                   10                  15

<210> SEQ ID NO 228
<211> LENGTH: 15
<212> TYPE: PRT
<213> ORGANISM: Human cytomegalovirus

<400> SEQUENCE: 228

Arg Arg Ile Glu Glu Ile Cys Met Lys Val Phe Ala Gln Tyr Ile
1               5                   10                  15

<210> SEQ ID NO 229
<211> LENGTH: 15
<212> TYPE: PRT
<213> ORGANISM: Human cytomegalovirus

<400> SEQUENCE: 229

Glu Ile Cys Met Lys Val Phe Ala Gln Tyr Ile Leu Gly Ala Asp
1               5                   10                  15

<210> SEQ ID NO 230
<211> LENGTH: 15
```

```
<212> TYPE: PRT
<213> ORGANISM: Human cytomegalovirus

<400> SEQUENCE: 230

Lys Val Phe Ala Gln Tyr Ile Leu Gly Ala Asp Pro Leu Arg Val
1               5                   10                  15

<210> SEQ ID NO 231
<211> LENGTH: 15
<212> TYPE: PRT
<213> ORGANISM: Human cytomegalovirus

<400> SEQUENCE: 231

Gln Tyr Ile Leu Gly Ala Asp Pro Leu Arg Val Cys Ser Pro Ser
1               5                   10                  15

<210> SEQ ID NO 232
<211> LENGTH: 15
<212> TYPE: PRT
<213> ORGANISM: Human cytomegalovirus

<400> SEQUENCE: 232

Gly Ala Asp Pro Leu Arg Val Cys Ser Pro Ser Val Asp Asp Leu
1               5                   10                  15

<210> SEQ ID NO 233
<211> LENGTH: 15
<212> TYPE: PRT
<213> ORGANISM: Human cytomegalovirus

<400> SEQUENCE: 233

Leu Arg Val Cys Ser Pro Ser Val Asp Asp Leu Arg Ala Ile Ala
1               5                   10                  15

<210> SEQ ID NO 234
<211> LENGTH: 15
<212> TYPE: PRT
<213> ORGANISM: Human cytomegalovirus

<400> SEQUENCE: 234

Ser Pro Ser Val Asp Asp Leu Arg Ala Ile Ala Glu Glu Ser Asp
1               5                   10                  15

<210> SEQ ID NO 235
<211> LENGTH: 15
<212> TYPE: PRT
<213> ORGANISM: Human cytomegalovirus

<400> SEQUENCE: 235

Asp Asp Leu Arg Ala Ile Ala Glu Glu Ser Asp Glu Glu Glu Ala
1               5                   10                  15

<210> SEQ ID NO 236
<211> LENGTH: 15
<212> TYPE: PRT
<213> ORGANISM: Human cytomegalovirus

<400> SEQUENCE: 236

Ala Ile Ala Glu Glu Ser Asp Glu Glu Glu Ala Ile Val Ala Tyr
1               5                   10                  15

<210> SEQ ID NO 237
<211> LENGTH: 15
<212> TYPE: PRT
<213> ORGANISM: Human cytomegalovirus
```

-continued

<400> SEQUENCE: 237

Glu Ser Asp Glu Glu Ala Ile Val Ala Tyr Thr Leu Ala Thr
1               5                   10                  15

<210> SEQ ID NO 238
<211> LENGTH: 15
<212> TYPE: PRT
<213> ORGANISM: Human cytomegalovirus

<400> SEQUENCE: 238

Glu Glu Ala Ile Val Ala Tyr Thr Leu Ala Thr Ala Gly Val Ser
1               5                   10                  15

<210> SEQ ID NO 239
<211> LENGTH: 15
<212> TYPE: PRT
<213> ORGANISM: Human cytomegalovirus

<400> SEQUENCE: 239

Val Ala Tyr Thr Leu Ala Thr Ala Gly Val Ser Ser Ser Asp Ser
1               5                   10                  15

<210> SEQ ID NO 240
<211> LENGTH: 15
<212> TYPE: PRT
<213> ORGANISM: Human cytomegalovirus

<400> SEQUENCE: 240

Leu Ala Thr Ala Gly Val Ser Ser Ser Asp Ser Leu Val Ser Pro
1               5                   10                  15

<210> SEQ ID NO 241
<211> LENGTH: 15
<212> TYPE: PRT
<213> ORGANISM: Human cytomegalovirus

<400> SEQUENCE: 241

Gly Val Ser Ser Ser Asp Ser Leu Val Ser Pro Pro Glu Ser Pro
1               5                   10                  15

<210> SEQ ID NO 242
<211> LENGTH: 15
<212> TYPE: PRT
<213> ORGANISM: Human cytomegalovirus

<400> SEQUENCE: 242

Ser Asp Ser Leu Val Ser Pro Pro Glu Ser Pro Val Pro Ala Thr
1               5                   10                  15

<210> SEQ ID NO 243
<211> LENGTH: 15
<212> TYPE: PRT
<213> ORGANISM: Human cytomegalovirus

<400> SEQUENCE: 243

Val Ser Pro Pro Glu Ser Pro Val Pro Ala Thr Ile Pro Leu Ser
1               5                   10                  15

<210> SEQ ID NO 244
<211> LENGTH: 15
<212> TYPE: PRT
<213> ORGANISM: Human cytomegalovirus

<400> SEQUENCE: 244

```
Glu Ser Pro Val Pro Ala Thr Ile Pro Leu Ser Ser Val Ile Val
 1               5                  10                  15

<210> SEQ ID NO 245
<211> LENGTH: 15
<212> TYPE: PRT
<213> ORGANISM: Human cytomegalovirus

<400> SEQUENCE: 245

Pro Ala Thr Ile Pro Leu Ser Ser Val Ile Val Ala Glu Asn Ser
 1               5                  10                  15

<210> SEQ ID NO 246
<211> LENGTH: 15
<212> TYPE: PRT
<213> ORGANISM: Human cytomegalovirus

<400> SEQUENCE: 246

Pro Leu Ser Ser Val Ile Val Ala Glu Asn Ser Asp Gln Glu Glu
 1               5                  10                  15

<210> SEQ ID NO 247
<211> LENGTH: 15
<212> TYPE: PRT
<213> ORGANISM: Human cytomegalovirus

<400> SEQUENCE: 247

Val Ile Val Ala Glu Asn Ser Asp Gln Glu Glu Ser Glu Gln Ser
 1               5                  10                  15

<210> SEQ ID NO 248
<211> LENGTH: 15
<212> TYPE: PRT
<213> ORGANISM: Human cytomegalovirus

<400> SEQUENCE: 248

Glu Asn Ser Asp Gln Glu Glu Ser Glu Gln Ser Asp Glu Glu Glu
 1               5                  10                  15

<210> SEQ ID NO 249
<211> LENGTH: 15
<212> TYPE: PRT
<213> ORGANISM: Human cytomegalovirus

<400> SEQUENCE: 249

Gln Glu Glu Ser Glu Gln Ser Asp Glu Glu Glu Glu Glu Gly Ala
 1               5                  10                  15

<210> SEQ ID NO 250
<211> LENGTH: 15
<212> TYPE: PRT
<213> ORGANISM: Human cytomegalovirus

<400> SEQUENCE: 250

Glu Gln Ser Asp Glu Glu Glu Glu Gly Ala Gln Glu Glu Arg
 1               5                  10                  15

<210> SEQ ID NO 251
<211> LENGTH: 15
<212> TYPE: PRT
<213> ORGANISM: Human cytomegalovirus

<400> SEQUENCE: 251

Glu Glu Glu Glu Glu Gly Ala Gln Glu Glu Arg Glu Asp Thr Val
```

```
1               5                  10                  15
```

<210> SEQ ID NO 252
<211> LENGTH: 15
<212> TYPE: PRT
<213> ORGANISM: Human cytomegalovirus

<400> SEQUENCE: 252

```
Glu Gly Ala Gln Glu Glu Arg Glu Asp Thr Val Ser Val Lys Ser
1               5                  10                  15
```

<210> SEQ ID NO 253
<211> LENGTH: 15
<212> TYPE: PRT
<213> ORGANISM: Human cytomegalovirus

<400> SEQUENCE: 253

```
Glu Glu Arg Glu Asp Thr Val Ser Val Lys Ser Glu Pro Val Ser
1               5                  10                  15
```

<210> SEQ ID NO 254
<211> LENGTH: 15
<212> TYPE: PRT
<213> ORGANISM: Human cytomegalovirus

<400> SEQUENCE: 254

```
Asp Thr Val Ser Val Lys Ser Glu Pro Val Ser Glu Ile Glu Glu
1               5                  10                  15
```

<210> SEQ ID NO 255
<211> LENGTH: 15
<212> TYPE: PRT
<213> ORGANISM: Human cytomegalovirus

<400> SEQUENCE: 255

```
Val Lys Ser Glu Pro Val Ser Glu Ile Glu Glu Val Ala Pro Glu
1               5                  10                  15
```

<210> SEQ ID NO 256
<211> LENGTH: 15
<212> TYPE: PRT
<213> ORGANISM: Human cytomegalovirus

<400> SEQUENCE: 256

```
Pro Val Ser Glu Ile Glu Glu Val Ala Pro Glu Glu Glu Glu Asp
1               5                  10                  15
```

<210> SEQ ID NO 257
<211> LENGTH: 15
<212> TYPE: PRT
<213> ORGANISM: Human cytomegalovirus

<400> SEQUENCE: 257

```
Ile Glu Glu Val Ala Pro Glu Glu Glu Asp Gly Ala Glu Glu
1               5                  10                  15
```

<210> SEQ ID NO 258
<211> LENGTH: 15
<212> TYPE: PRT
<213> ORGANISM: Human cytomegalovirus

<400> SEQUENCE: 258

```
Ala Pro Glu Glu Glu Glu Asp Gly Ala Glu Glu Pro Thr Ala Ser
1               5                  10                  15
```

-continued

```
<210> SEQ ID NO 259
<211> LENGTH: 15
<212> TYPE: PRT
<213> ORGANISM: Human cytomegalovirus

<400> SEQUENCE: 259

Glu Glu Asp Gly Ala Glu Glu Pro Thr Ala Ser Gly Gly Lys Ser
1               5                   10                  15

<210> SEQ ID NO 260
<211> LENGTH: 15
<212> TYPE: PRT
<213> ORGANISM: Human cytomegalovirus

<400> SEQUENCE: 260

Ala Glu Glu Pro Thr Ala Ser Gly Gly Lys Ser Thr His Pro Met
1               5                   10                  15

<210> SEQ ID NO 261
<211> LENGTH: 15
<212> TYPE: PRT
<213> ORGANISM: Human cytomegalovirus

<400> SEQUENCE: 261

Thr Ala Ser Gly Gly Lys Ser Thr His Pro Met Val Thr Arg Ser
1               5                   10                  15

<210> SEQ ID NO 262
<211> LENGTH: 15
<212> TYPE: PRT
<213> ORGANISM: Human cytomegalovirus

<400> SEQUENCE: 262

Gly Lys Ser Thr His Pro Met Val Thr Arg Ser Lys Ala Asp Gln
1               5                   10                  15
```